US010725020B2

(12) United States Patent
Cheng et al.

(10) Patent No.: US 10,725,020 B2
(45) Date of Patent: Jul. 28, 2020

(54) HIGH THROUGHPUT MINIATURIZED ASSAY SYSTEM AND METHODS

(71) Applicant: Curiox Biosystems Pte Ltd., Singapore (SG)

(72) Inventors: Kong Leong Cheng, Singapore (SG); Siah Chong Cheong, Singapore (SG); Namyong Kim, Allston, MA (US); Eng Seng Lim, Singapore (SG); Hanwen Melvin Lye, Singapore (SG); Zhong Wang, Singapore (SG); Wan Yee Leong, Boston, MA (US); Mark S. Phong, Singapore (SG)

(73) Assignee: Curiox Biosystems Pte Ltd., Singapore (SG)

( * ) Notice: Subject to any disclaimer, the term of this patent is extended or adjusted under 35 U.S.C. 154(b) by 0 days.

(21) Appl. No.: 14/050,321

(22) Filed: Oct. 9, 2013

(65) Prior Publication Data
US 2014/0235468 A1 Aug. 21, 2014

Related U.S. Application Data

(63) Continuation-in-part of application No. PCT/IB2013/000623, filed on Feb. 5, 2013, and a continuation-in-part of application No. 13/811,638, filed on Jan. 22, 2013, now Pat. No. 9,878,328, and a continuation-in-part of application No. 13/607,643, filed on Sep. 7, 2012, now abandoned, and a continuation-in-part of application No. 13/264,913, filed on Oct. 17, 2011, now Pat. No. 8,784,752, and a continuation-in-part of application No. 11/984,197, filed on Nov. 14, 2007, now Pat. No. 8,691,147.

(60) Provisional application No. 61/711,725.

(51) Int. Cl.
*G01N 33/50* (2006.01)
*C12N 15/10* (2006.01)
*B01L 3/00* (2006.01)
*G01N 33/543* (2006.01)
*G01N 35/10* (2006.01)

(52) U.S. Cl.
CPC ........ *G01N 33/5008* (2013.01); *B01L 3/5088* (2013.01); *C12N 15/1082* (2013.01); *G01N 33/54373* (2013.01); *B01L 3/5085* (2013.01); *B01L 13/02* (2019.08); *B01L 2300/0609* (2013.01); *B01L 2300/089* (2013.01); *B01L 2300/0829* (2013.01); *B01L 2300/161* (2013.01); *B01L 2400/0415* (2013.01); *G01N 2035/1037* (2013.01)

(58) Field of Classification Search
CPC .................................. G01N 33/5008
USPC ........................................... 506/9
See application file for complete search history.

(56) References Cited

U.S. PATENT DOCUMENTS

| | | |
|---|---|---|
| 3,426,108 A | 2/1969 | Britten |
| 3,754,872 A | 8/1973 | Zauft |
| 5,041,266 A | 8/1991 | Fox |
| 5,219,528 A | 6/1993 | Clark |
| 5,229,163 A | 7/1993 | Fox |
| 5,506,121 A | 4/1996 | Skerra et al. |
| 5,560,811 A | 10/1996 | Briggs et al. |
| 5,691,147 A | 11/1997 | Draetta |
| RE35,894 E | 9/1998 | Ellison et al. |
| 5,817,510 A | 10/1998 | Pandey et al. |
| 6,048,908 A | 4/2000 | Kitagawa |
| 6,086,825 A | 7/2000 | Sundberg et al. |
| 6,103,493 A | 8/2000 | Skerra et al. |
| 6,130,098 A | 10/2000 | Handique et al. |
| 6,238,626 B1 | 5/2001 | Higuchi et al. |
| 6,331,441 B1 | 12/2001 | Balch et al. |
| 6,534,014 B1 | 3/2003 | Mainquist et al. |
| 6,565,813 B1 * | 5/2003 | Garyantes ........... B01F 13/0071 422/553 |
| 6,578,952 B1 | 6/2003 | Sugiyama et al. |
| 6,664,044 B1 | 12/2003 | Sato |
| 6,699,437 B1 | 3/2004 | Astle |
| 6,716,629 B2 | 4/2004 | Hess et al. |

(Continued)

FOREIGN PATENT DOCUMENTS

| | | |
|---|---|---|
| CN | 1460723 | 12/2003 |
| CN | 1858593 | 11/2006 |

(Continued)

OTHER PUBLICATIONS

Erfle eta l., Nature Protocols, Mar. 1, 2007, 2(2), pp. 392-399.*
Takahashi et al., Cell, Aug. 25, 2006, 126, pp. 663-676.*
Lowe et al., Tibtech, Jun. 1998, vol. 16, pp. 272-277.*
Vancha et al. (BMC Biotechnology, Oct. 15, 2004, pp. 1-12).*
Kim, Office Action, U.S. Appl. No. 14/326,780, dated Oct. 28, 2015, 13 pgs.
Kim, Office Action, U.S. Appl. No. 14/452,172, dated Oct. 23, 2015, 16 pgs.
Kim, Office Action, U.S. Appl. No. 14/338,168, dated Nov. 6, 2015, 8 pgs.

(Continued)

*Primary Examiner* — Karla A Dines
(74) *Attorney, Agent, or Firm* — Morgan, Lewis & Bockius LLP

(57) ABSTRACT

The present invention provides an apparatus for conducting biological assays which employs "virtual wells" in lieu of the physical wells of conventional array plates. Also provided are methods of processing a sample and/or culturing cells using the apparatus and systems described herein. In some embodiments, the apparatus includes a first structure having a sheet layer with a plurality of discrete through holes; and a second structure coupled to the first structure, the second structure including a base layer. At least a portion of a first surface of the sheet layer of the first structure is exposed from the second structure, and a second surface of the sheet layer, opposite to the first surface of the sheet layer, is embedded in the base layer of the second structure adjacent the first surface of the base layer.

20 Claims, 65 Drawing Sheets

(56) References Cited

U.S. PATENT DOCUMENTS

| | | | |
|---|---|---|---|
| 6,767,733 B1 | 7/2004 | Green | |
| 6,902,705 B1 | 6/2005 | Caillat et al. | |
| 7,163,823 B2 | 1/2007 | Patno et al. | |
| 7,344,877 B1 | 3/2008 | Camacho et al. | |
| 7,439,056 B2 | 10/2008 | Duffy et al. | |
| 7,666,362 B2 | 2/2010 | Shanler | |
| 7,794,799 B1 | 9/2010 | Kim et al. | |
| 7,854,343 B2 | 12/2010 | Ellson et al. | |
| 7,858,044 B2 | 12/2010 | Coassin et al. | |
| 8,221,697 B2 | 7/2012 | Nichols et al. | |
| 8,337,778 B2 | 12/2012 | Duffy et al. | |
| 8,987,174 B2 | 3/2015 | Routenberg | |
| 2002/0016009 A1 | 2/2002 | Ogura | |
| 2002/0064482 A1* | 5/2002 | Tisone | B01J 19/0046 422/400 |
| 2002/0094533 A1 | 7/2002 | Hess et al. | |
| 2003/0032046 A1 | 2/2003 | Duffy et al. | |
| 2003/0083474 A1 | 5/2003 | Schmidt | |
| 2003/0113813 A1 | 6/2003 | Heidaran et al. | |
| 2003/0124599 A1 | 7/2003 | Chen et al. | |
| 2003/0148401 A1 | 8/2003 | Agrawal et al. | |
| 2003/0209560 A1 | 11/2003 | Hui et al. | |
| 2004/0106156 A1 | 6/2004 | Perez et al. | |
| 2004/0106191 A1 | 6/2004 | Muser | |
| 2004/0136876 A1 | 7/2004 | Fouillet et al. | |
| 2004/0142460 A1 | 7/2004 | Cima et al. | |
| 2004/0208792 A1 | 10/2004 | Linton et al. | |
| 2004/0234966 A1 | 11/2004 | Bryning et al. | |
| 2005/0045539 A1 | 3/2005 | Yu et al. | |
| 2005/0058577 A1 | 3/2005 | Micklash, II et al. | |
| 2005/0079105 A1 | 4/2005 | Hunter et al. | |
| 2005/0084423 A1 | 4/2005 | Zarowitz et al. | |
| 2005/0186579 A1 | 8/2005 | Dellinger et al. | |
| 2006/0013031 A1 | 1/2006 | Ravkin et al. | |
| 2006/0051249 A1 | 3/2006 | Knebel et al. | |
| 2006/0078893 A1* | 4/2006 | Griffiths | B01F 5/0646 435/6.16 |
| 2006/0105453 A1 | 5/2006 | Brenan et al. | |
| 2006/0105462 A1 | 5/2006 | Sellek-Prince | |
| 2006/0142468 A1 | 6/2006 | Downing, Jr. et al. | |
| 2007/0003448 A1 | 1/2007 | Kanigan et al. | |
| 2007/0005169 A1 | 1/2007 | Rohnert et al. | |
| 2007/0077651 A1* | 4/2007 | Guarino | C07K 5/0806 435/325 |
| 2007/0099208 A1 | 5/2007 | Drmanac | |
| 2007/0117765 A1* | 5/2007 | Sauve | C07H 19/048 514/43 |
| 2008/0003671 A1 | 1/2008 | Martin | |
| 2008/0173544 A1 | 7/2008 | Seul et al. | |
| 2009/0032064 A1 | 2/2009 | Gifford et al. | |
| 2009/0142564 A1 | 6/2009 | Plissonnier et al. | |
| 2009/0148348 A1 | 6/2009 | Pettigrew et al. | |
| 2009/0227474 A1 | 9/2009 | Gordon et al. | |
| 2009/0286317 A1 | 11/2009 | Demmler et al. | |
| 2010/0000304 A1 | 1/2010 | Kim et al. | |
| 2010/0167950 A1 | 7/2010 | Juang et al. | |
| 2010/0297767 A1 | 11/2010 | Hattori et al. | |
| 2012/0198928 A1 | 8/2012 | Streit et al. | |
| 2012/0220497 A1 | 8/2012 | Jacobson et al. | |
| 2015/0018248 A1 | 1/2015 | Kim | |
| 2016/0169867 A1 | 6/2016 | Khine et al. | |
| 2016/0332155 A1 | 11/2016 | Schoeneck et al. | |

FOREIGN PATENT DOCUMENTS

| | | |
|---|---|---|
| CN | 101031363 | 9/2007 |
| DE | 10043042 C2 | 6/2002 |
| EP | 0812693 A1 | 12/1997 |
| EP | 1348533 B1 | 7/2002 |
| EP | 1358939 A2 | 4/2003 |
| EP | 1316360 B1 | 6/2003 |
| EP | 1386657 A1 | 7/2003 |
| EP | 1473079 A1 | 2/2004 |
| EP | 1399263 B1 | 3/2004 |
| EP | 1788047 A1 | 8/2005 |
| EP | 1683571 A1 | 1/2006 |
| GB | 1291610 | 10/1972 |
| GB | 2332273 A | 6/1999 |
| GB | 2334954 A | 6/1999 |
| JP | 3120453 B2 | 12/2000 |
| JP | 2002-502955 A | 1/2002 |
| JP | 2003-033177 A | 9/2003 |
| JP | 2004-020280 A | 1/2004 |
| JP | 2004-077476 A | 3/2004 |
| JP | 2004-535176 A | 11/2004 |
| JP | 2005-003803 A | 1/2005 |
| JP | 2005-099004 A | 4/2005 |
| WO | WO 1996-23879 | 8/1996 |
| WO | WO 1998-055852 | 12/1998 |
| WO | WO 99/39829 A1 | 8/1999 |
| WO | WO 99/55826 | 11/1999 |
| WO | WO 2000-014311 | 3/2000 |
| WO | WO 00-58735 | 10/2000 |
| WO | WO 2001-004144 A2 | 1/2001 |
| WO | WO 2003-029462 A1 | 4/2003 |
| WO | WO 2004-030820 A2 | 4/2004 |
| WO | WO 2004-111610 A2 | 12/2004 |
| WO | WO 2005/019254 A1 | 3/2005 |
| WO | WO 2005/019255 A1 | 3/2005 |
| WO | WO 2005/019256 A2 | 3/2005 |
| WO | WO 2006/004739 A2 | 1/2006 |
| WO | WO 2006/046699 A1 | 5/2006 |
| WO | WO 2007/102785 A1 | 9/2007 |
| WO | WO 2008/063136 A1 | 5/2008 |
| WO | WO 98/47003 | 10/2008 |
| WO | WO 2010/120249 A1 | 10/2010 |
| WO | WO 2012/011877 A2 | 1/2012 |

OTHER PUBLICATIONS

Agency for Science, Technology and Research, International Preliminary Report on Patentability, PCT/SG2007/000393, dated May 26, 2009, 4 pgs.

Agency for Science, Technology and Research, International Search Report and Written Opinion of the ISA, PCT/SG2007/000393, dated Feb. 20, 2008, 7 pgs.

Agency for Science, Technology and Research, Notification of Reasons for Refusal, JP 2009-538373, dated Nov. 10, 2011, 7 pgs.

Agency for Science, Technology and Research, Notification of Reasons for Refusal, JP 2012-196318, dated Dec. 10, 2013, 3 pgs.

Agency for Science, Technology and Research, Notification of the First Office Action, CN 200780048922.8, dated Nov. 12, 2010, 4 pgs (available in Chinese only).

Agency for Science, Technology and Research, Notification of the Second Office Action, CN 200780048922.8, dated May 17, 2011, 4 pgs.

Agency for Science, Technology and Research, Notification on the Grant of Patent Right for Invention, CN 200780048922.8, Sep. 22, 2011, 1 pg.

Agency for Science, Technology and Research, Supplementary Search Report, EP 07835548.4, dated Jun. 30, 2015, 5 pgs.

Asberg, Surgace Energy Modified Chips for Detection of Conformational States and Enzymatic Activity in Biomolecules, Langmuir, 2006, pp. 2205-2211.

Beck, Improving Stamps for 10 nm Level Wafer Scale Nanoimprint Lithography, Microelectron. Eng., 2002, pp. 61-62 and 441.

Benor, Microstructuring by Microcontact Printing and Selective Surface Dewetting, J. of Vacuum Science & Technology B, 2007, pp. 1321-1326.

Beste, Small Antibody-like Proteins with Prescrived Ligand Specificities Derived from the Lipocalin Fold, Proc. Natl. Acad. Sci, USA, 1999, pp. 1898-1903.

Biffinger, The Polar Hydrophobicity of Cluorinated Compounds, ChemBioChem, 2004, pp. 622-627.

Burbulis, Quantifying Small Numbers of Antibodies with a 'Near-Universal' Protein-DNA Chimera, Nature Methods, 2007.

Chiriac, Magnetic GMI Sensor for Detection of Biomolecules, J. Magnetism and Magnetic Materials, 2005, pp. 671-676.

(56) References Cited

OTHER PUBLICATIONS

Churaev, Wetting of Low-Energy Surgfaces, Advances in Colloid and Interface Science, 2007, pp. 134-135, 15-23.
Curiox Biosystems Pte Ltd, International Preliminary Report on Patentability, PCT/SG2010/000153, dated Oct. 18, 2011, 15 pgs.
Curiox Biosystems Pte Ltd, International Preliminary Report on Patentability, PCT/SG2011/000263, dated Dec. 21, 2012, 5 pgs.
Curiox Biosystems Pte Ltd, International Search Report and Written Opinion, PCT/IB2013/000623, dated Jul. 10, 2013, 7 pgs.
Curiox Biosystems Pte Ltd, International Search Report and Written Opinion, PCT/SG2006/000050, dated May 8, 2006, 21 pgs.
Curiox Biosystems Pte Ltd, International Search Report and Written Opinion, PCT/SG2010/000153, dated Sep. 17, 2010, 20 pgs.
Curiox Biosystems Pte Ltd, International Search Report and Written Opinion, PCT/SG2011/000263, dated Feb. 29, 2012, 20 pgs.
Daniel, Vibration-Actuated Drop Motion on Surfaces bor Batch Microfluidic Processes, Langmuir, 2005, pp. 4220-4228.
Dill, Modeling Water, The Hydrophobic Effect and Ion Solvation, Annu. Rev. Biophys. Biomol. Struc, 2005, pp. 173-199.
Gao, A Commercially Available Perfectly Hydrophobic Material, Langmuir, 2007, pp. 9125-9127.
Gascoyne, Dielectrophoresis-based Programmable Fluidic Processors, Lab-on-a-Chip, 2004, pp. 299-309.
Genua, Functional Patterns Obtained by Nanoimprinting Lithography and Subsequent Growth of Polymer Brushes, Nanotechnology, 2007, 215301, 7 pgs.
Gill, Pharmaceutical Drug Discovery Using Novel Protein Scaffolds, Current Opinion in Biotechnology, 2006, 653-658.
Giovambattista, Effect of Surface Polarity on Water Contact Angle and Interfacial Hydration Structure, J. Phys. Chem., 2007, pp. 9581-9587.
Goddard, Polymer Surface Modification for the Attachment of Bioactive Compounds, Progress in Polymer Science, 2007, pp. 698-725.
Griffiths, Miniaturising the Laboratory in Emulsion Droplets, Trends in Biotechnology, 2006, pp. 395-402.
Herrmann, Enxymatically-Generated Fluorescent Detection in Micro-Channels with Internal Magnetic Mixing for the Development of Parallel Miicrofluidic ELISA, Lab-on-a-Chip, 2006, pp. 555-560.
Holt, Domain Antibodies: Proteins for Therapy, Trends Biotechnol, 2003, pp. 484-490.
Hutten, New Magnetic Nanoparticles for Biotechnology, J. Biotech., 2004, pp. 47-63.
Iliades, Triabodies: Single Chain Fv Fragments without a Linker Form Trivalent Trimers, FEBS Lett, 1997, pp. 437-441.
Jakobs, Micrometer Scale Gel Patterns, Colloids & Surfaces A: PhysioChem. Eng. Aspects, 2006, pp. 33-40.
Jung, Wetting Transition of Water Droplets on Superhydrophobic Patterned Surfaces, Scripta Materialia, 2007, pp. 1057-1060.
Kanta, Preparation of Silica-on-Titania Patterns with a Wettability Contrast, Langmuir, 2005, 5790-5794.
Kim, Final Office Action, U.S. Appl. No. 13/264,913, dated Jun. 21, 2013, 11 pgs.
Kim, Notice of Allowance, U.S. Appl. No. 12/282,162, dated May 14, 2012, 7 pgs.
Kim, Office Action, U.S. Appl. No. 12/282,162, dated Jun. 27, 2011, 8 pgs.
Kim, Office Action, U.S. Appl. No. 13/264,913, dated Nov. 7, 2012, 9 pgs.
Kim, Office Action, U.S. Appl. No. 13/264,913, dated Sep. 26, 2013, 10 pgs.
Kusumaatmaja, Controlling Drop Size and Polydispersity Using Chemically Patterned Surfaces, Langmuir, 2007, pp. 956-959.
Kwon, Quantitative Evaluation of the Relative Cell Permeability of Peptoids and Peptides, J. AM. Chem. Soc., 2007, pp. 1508-1509.
Leck, Final Office Action, U.S. Appl. No. 11/984,197, dated May 8, 2012, 10 pgs.
Leck, Office Action, U.S. Appl. No. 11/984,197, dated Mar. 14, 2013, 11 pgs.
Leck, Office Action, U.S. Appl. No. 11/984,197, dated May 26, 2011, 11 pgs.
Leck, Office Action, U.S. Appl. No. 11/984,197, dated Jul. 31, 2013, 12 pgs.
Li, What Do We Need for a Superhydrophobic surface? A review on the recent progress in the preparation of superhydrophobic surfaces, Chem. Soc. Rev, 2007, pp. 1350-1368.
Luca, Preparation of TIOx Thin Films by Reactive Pulsed-Laser Ablation, J. Optoelectronics and Adv. Materials, Apr. 2005, pp. 625-630.
Lundgren, Modeling of Wetting: A Study of Nanowetting at Rough and Heterogeneous Surfaces, Langmuir, 2007, pp. 1187-1194.
Ma, Superhydrophobic Surfaces, Current Opinion in Colloid & Interface Science, 2006, pp. 193-202.
Mardare, Microelectrochemical Lithography: A method for Direct Writing of Surface Oxides, Electrochimica Acta, 2007, pp. 7865-7869.
Matsuda, Phosphorylcholine-Endcapped Oligomer and Block Co-Oligomer and Surface Biological Reactivity, Biomaterials, 2003, pp. 4517-4527.
Meyer, Recent Progress in Understanding Hydrophobic Interactions, Proc. Netl. Acad. Sci USA, 2006, pp. 15739-15746.
Mosavi, The Ankyrin Repeat as Molecular Architecture for Protein Recognition, Protein Science, 2004, pp. 1435-1448.
Opdahl, Polymer Surface Science, The Chemical Record, 2001, pp. 101-122.
Perfulorodecalin-FluoroMed, http://fluoromed.com/products/perfluorodecalin.html (no date).
Pollack, Electrowetting-based Actuation of Liquid Droplets for Microfluidic Applications, Appl. Phys. Lett., 2000, pp. 1725-1726.
Popp, Sortagging: A versatile Method for Protein Labeling, Nature Chemical Biology, 2007, pp. 707-708.
Rastogi, Development and Evaluation of Realistic Microbioassys in Freely Suspended Droplets on a Chip, Biomicrofludics, 2007, 014107-1-014107-17.
Roach, Controllling Nonspecific Protein Adsorption in a Plug-Based Microfluidic System by Controlling Interfacial Chemistry Using Fluorous-Phase Surfactants, Analytical Chemistry, vol. 77, No. 3, Feb. 1, 2005, pp. 785-796.
Ronaghi, Pyrosequestering Sheds Light on DNA Sequestering, Genome Research, 2001, pp. 3-11.
Rose, Microdispensing Technologies in Drug Discovery, Drug Discovery Today, 1999, pp. 411-419.
Satriano, Bacterial Adhesion Onto Nanopatterned Polymer Surfaces, Materials Science & Engineering C, 2006, pp. 942-946.
Silverman, Multivalent Avimer Proteins Evolved by Exon Shuffling of a Family of Human Receptor Domains, Nature Biotechnology, 2005, pp. 1556-1561.
Skerra, Engineered Protein Scaffolds for Molecular Recognition, J. Mol. Recognit., 2000, pp. 167-187.
Song, Miniature Biochip System for Detection of *Sscherichi coli* O157:H7 Based on Antibody-Immobilized Capillary Reactors and Enzyme-linked Immunosorbent Assay, Analytica Chimica Acta, 2004, pp. 115-121.
Stephenson, Quantifying the Hydrophobic Effect: A Computer Simulation-Molecular-Thermodynamic Model for the Self-Assembly of Hydrophibic and Amphiphilic Solutes in Aqueous Solution, Jp. Phys. Chem. B, 2007, 1025-1044.
Stone, The Assembly of Single Domain Antibodies into Bispecific Decavalent Molecules, J. Immunological Methods, 2007, pp. 88-94.
Sundberg, Contact Angle Measurements by Confocal Microscopy for Non-Destructive Microscale Surface Characterization, J. Colloid and Interface Science, 2007, pp. 454-460.
Van Oss, Long-Rage and Short-Range Mechanisms of Hydrophobic Attraction and Hydrophilic Repulsion in Specific and Aspecific Interactions, J. Mol. Recognit., 2003, pp. 177-190.
Wang, Flow-Focusing Generation of Monodisperse Water Droplets Wrapped by Ionic Liquid on Microfluidic Chips: From Plug to Sphere, langmuir, 2007, pp. 11924-11931.
Wang, In-Situ Wilhelmy Balance Surface Energy Determination of Poly(3-hexylthiophere) and Poly(3,4-ethylenedioxythiophere) during Electrochemical Doping-Dedoping, Langmuir, 2006, pp. 9287-9294.

(56) References Cited

OTHER PUBLICATIONS

Washizu, Elecrostatic Actuation of Liquid Droplets for Microreactor Applications, IEEE Transactions on Industry Applications, vol. 34, No. 4, Jul.-Aug. 1998.
West, Microplasma Writing for Surface-Directed Millifludics, Lab-on-a-Chip, 2007, pp. 981-983.
Widom, The Hydrophobic Effect, Phys. Chem. Chem, Phys., 2003, pp. 3085-3093.
Wixforth, Flatland Fluidics, mstnews, 2002, pp. 42-43.
Agency for Science, Technology and Research, Decision to Grant, JP2012-196318, dated Sep. 12, 2014, 3 pgs.
Curiox Biosystems Pte Ltd, International Preliminary Report on Patentablity, PCT/IB2013/000623, dated Aug. 5, 2014, 7 pgs.
Agency for Science, Technology and Research, Notification of First Office Action, CN 201110401674.9, dated Dec. 30, 2013, 9 pgs.
Curiox Biosystems PTE Ltd., International Search Report and Written Opinion, PCT/US2015/019760, dated Jun. 2, 2015, 12 pgs.
Agency for Science, Technology and Research, Communication Pursuant to Article 94, EP07835548-4, dated Jul. 17, 2015, 3 pgs.
Decision to Grant, Application No. CN201110401674.9, dated Aug. 7, 2014, 2 pgs.
Kim, Office Action, U.S. Appl. No. 13/811,638, dated Sep. 11, 2015, 29 pgs.
Kim, Final Office Action, U.S. Appl. No. 13/811,638, dated Apr. 21, 2016, 24 pgs.
Kim, Final Office Action, U.S. Appl. No. 14/326,780, dated May 10, 2016, 11 pgs.
Kim, Final Office Action, U.S. Appl. No. 14/452,172, dated Jun. 3, 2016, 17 pgs.
Kim, Office Action, U.S. Appl. No. 14/338,168, dated Jun. 22, 2016, 9 pgs.
Agency for Science, Technology and Research, First Examination Report, IN3674/CHEN/P2009, dated Oct. 7, 2016, 9 pgs.
Kim, Notice of Allowance, U.S. Appl. No. 14/326,780, dated Sep. 22, 2016, 7 pgs.
Leck, Notice of Allowance, U.S. Appl. No. 14/246,004, dated Sep. 15, 2016, 8 pgs.
Kim, Final Office Action, U.S. Appl. No. 13/811,638, dated Feb. 9, 2017, 29 pgs.
Kim, Notice of Allowance, U.S. Appl. No. 14/452,172, dated Dec. 12, 2017, 9 pgs.
Kim, Notice of Allowance, U.S. Appl. No. 14/338,168, dated Sep. 13, 2017, 8 pgs.
Leck, Office Action, U.S. Appl. No. 15/424,604, dated Aug. 11, 2017, 7 pgs.
Agency for Science, Technology and Research, Communication Pursuant to Article 94, EP07835548-4, dated Oct. 2, 2018, 3 pgs.
Curiox, International Preliminary Report on Patentability, PCT/IB2018/000436, dated Oct. 8, 2019, 11 pgs.
Curiox, International Search Report/Written Opinion, PCT/IB2018/000436, dated Sep. 7, 2018, 14 pgs.

* cited by examiner

FIG. 4
BEFORE COMPOUND TREATMENT	AFTER COMPOUND TREATMENT
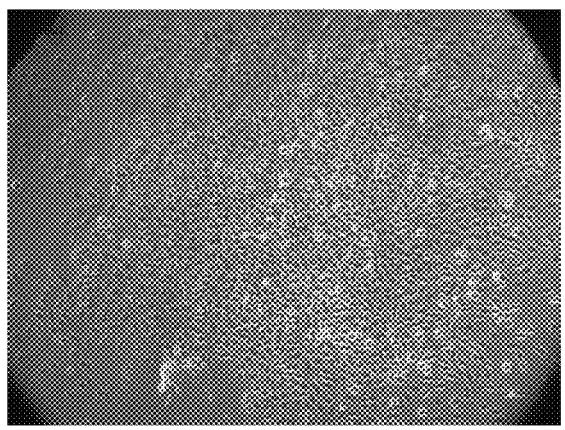
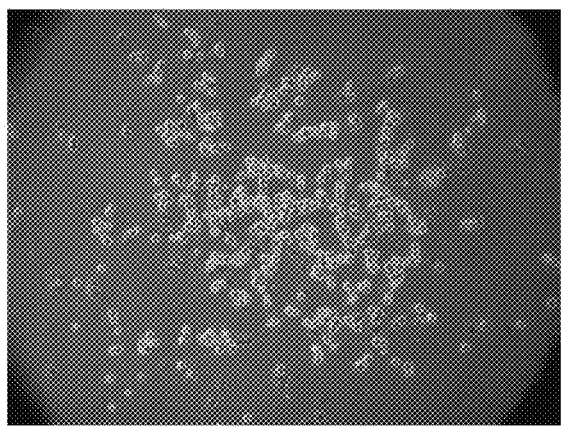
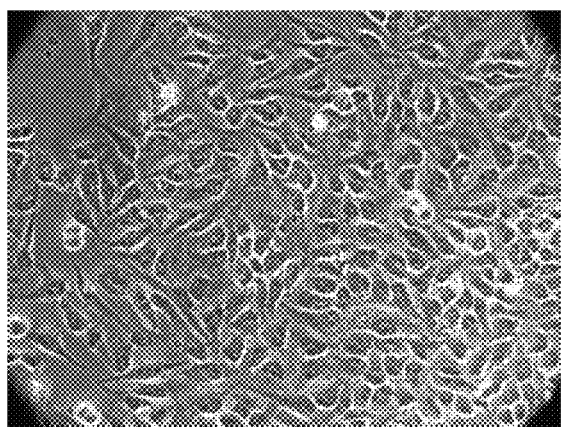
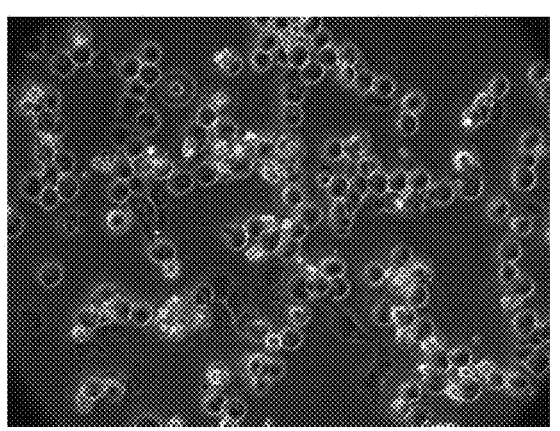

1. Prepare DNA-gelatin to desired DNA concentration to make final 0.17% Gelatin. Add at 2ul on DropArray™ 5384 plate.

2. Allow drying of DNA-gelatin (e.g., RT, overnight).

3. Add half-volume of transfection mix

4. Add equal volume of cells in transfection reagent drop. Incubate DropArray™ 5384 plate for approximately 40 hours in a 37° C, 5% $CO_2$ humidified incubator

A.            B.            C.

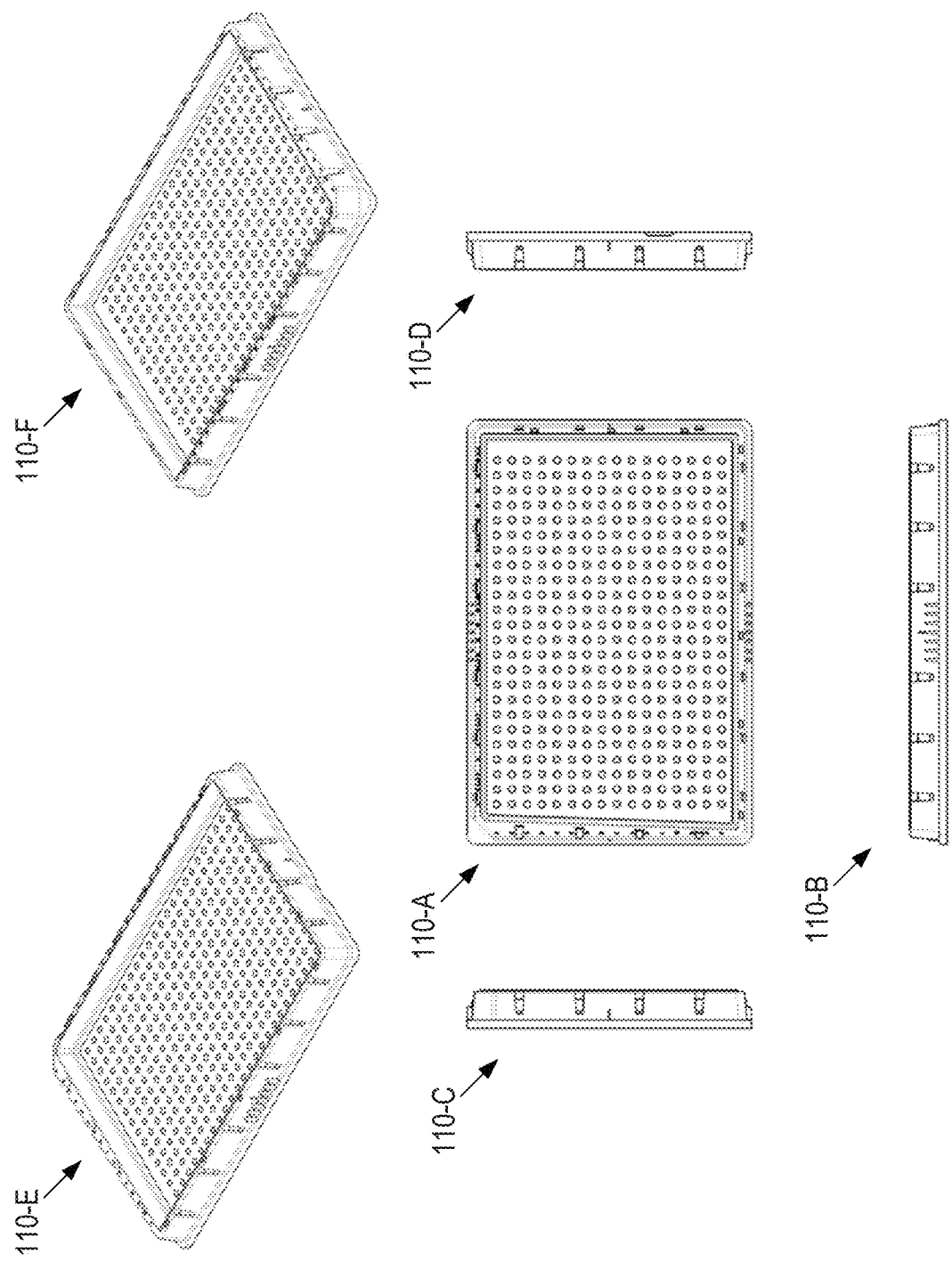

620 Cool the plastic material to form a second structure so that the first structure and the second structure are coupled, the second structure including a base layer and one or more vertical structures along a periphery of the base layer, adjacent a first surface of the base layer. At least a portion of a first surface of the sheet layer of the first structure is exposed from the second structure, and a second surface of the sheet layer, opposite to the first surface of the sheet layer, is embedded in the base layer of the second structure adjacent the first surface of the base layer.

622 The plastic material of the second structure is optically transparent

624 Couple a third structure with at least the second structure over at least a portion of the one or more vertical structures, the third structure including one or more side walls 626 The one or more vertical structures of the second structure include a plurality of pins vertically protruding from the rest of the one or more vertical structures 628 Mold the third structure over at least a portion of the one or more vertical structures with a second mold so as to couple the second structure and the third structure, and remove a combination of the second structure and the third structure from the second mold by pushing respective locations on the third structure that correspond to the plurality of pins of the second structure.

630 The one or more side walls are made of a plastic material that has a glass transition temperature lower than the glass transition temperature of the second structure 632 The one or more vertical structures include one or more side walls

Figure 16B

634 The one or more side walls are made of a material that has Shore A hardness of 85 or less 636 The one or more side walls each have an inner surface, an outer surface, a bottom adjacent the sheet layer of the first structure, and a top surface opposite the bottom, and a respective side wall of the one or more side walls includes one or more lips on the top surface, at least one of the one or more lips aligned with the inner surface of the respective side wall 638 The one or more side walls each have an inner surface, an outer surface, a bottom adjacent the sheet layer of the first structure, and a top surface opposite the bottom, and a respective side wall of the one or more side walls includes one or more vertical indentations along the outer surface of the respective side wall 640 The one or more side walls are made of a hydrophobic material of a surface tension lower than 35 dynes/cm 642 The one or more side walls each have an inner surface, an outer surface, a bottom adjacent the sheet layer of the first structure, and a top surface opposite the bottom, and the inner surface of a respective side wall of the one or more side walls is coated to expose a hydrophobic surface of a surface tension lower than 35 dynes/cm 644 The second structure includes a plurality of holding locations, the method comprising aligning the first structure and the second structure so that the plurality of discrete through holes defined in the sheet layer of the first structure is offset from the plurality of holding locations in the second structure

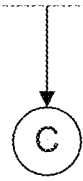

Figure 16C

646 The mold is configured so that a top surface of the sheet layer of the first structure is aligned with a top surface of the base layer of the second structure 648 The mold is configured so that a top surface of the sheet layer of the first structure is above a top surface of the base layer of the second structure 650 The mold is configured so that a top surface of the sheet layer of the first structure is below a top surface of the base layer of the second structure 652 The first surface of the mold has one or more of: a plurality of indentations and a plurality of protrusions corresponding to the plurality of discrete through holes defined in the sheet layer 652 At least one of the side walls include one or more handles, each handle comprising a plurality of parallel fins

Figure 16D

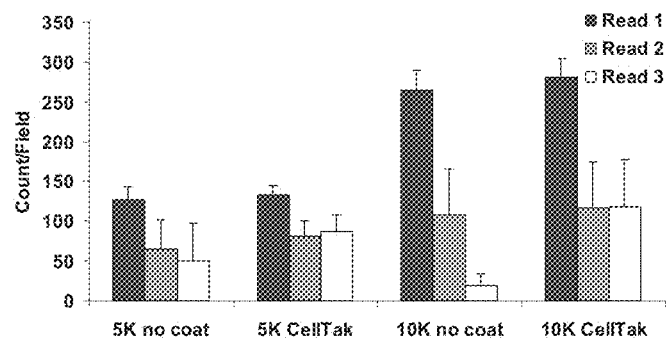
FIG. 17A
Cell Count
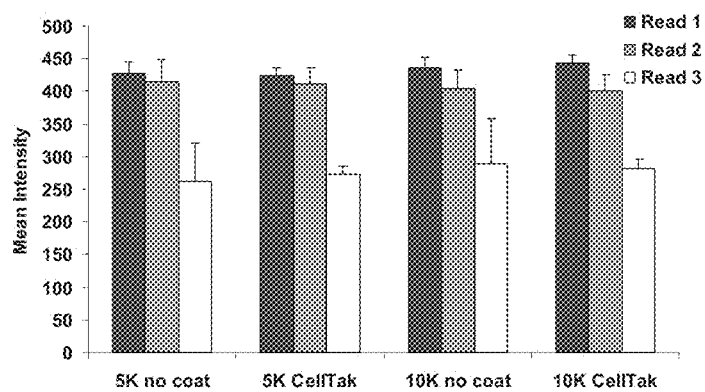
FIG. 17B
MitoTacker Signal
FIG. 17C
Sample images from 5K/well w/ CellTak
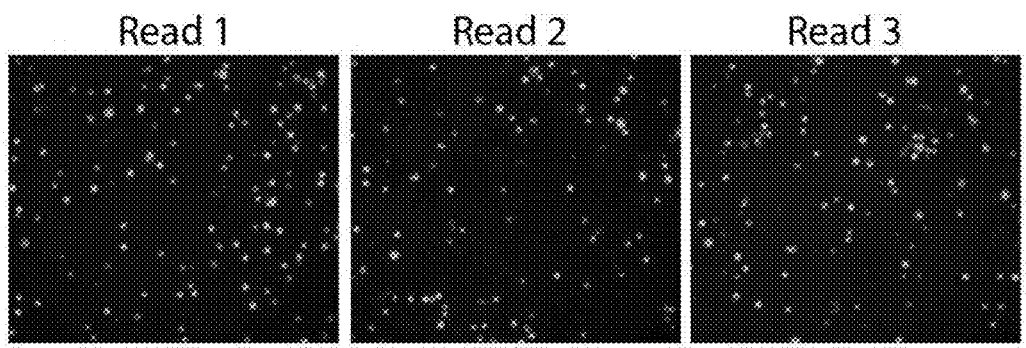

Superimposed Images

Cell images from the same field in the same well at different readings.
Blue: DAPI
Green: Mitotracker
Superimpose DAPI images
Conclusion: PBMCs are still moving (more specifically, sliding on a surface) but loss is minimal during extensive washes.
Read 1
No Wash
Read 2
3 times wash
Read 3
6 times wash
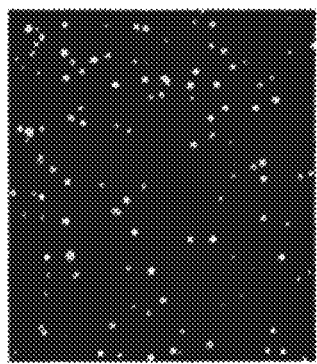 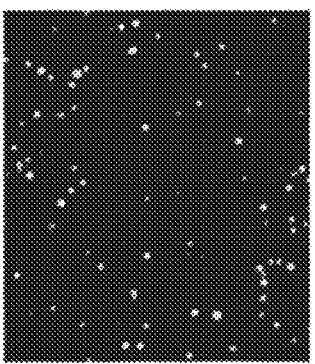 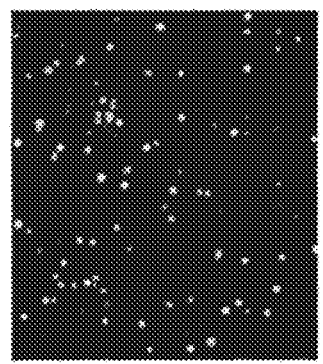
FIG. 21

Post 6-day Primary Hu Bone Marrow cells stained with: Hoechst, CD11B (suspension erythrocyte-like cells)

*20X Objective lens, Cellomics ArrayScan VTi*

Seed Primary Mu/Hu Bone Marrow cells 2000 - 8000 cells/10ul → Culture for 3* days (For Hu cells, continue culture up to 7 days) → Fix, Perm and stain with CD11B and CD71 biomarkers → (Up to 3x washes) → Imaging or Flow Cytometry Post 6-day Primary Hu Bone Marrow cells stained with:
Hoechst, CD71 (myeloid cells)
*20X Objective lens, Cellomics ArrayScan VTi*

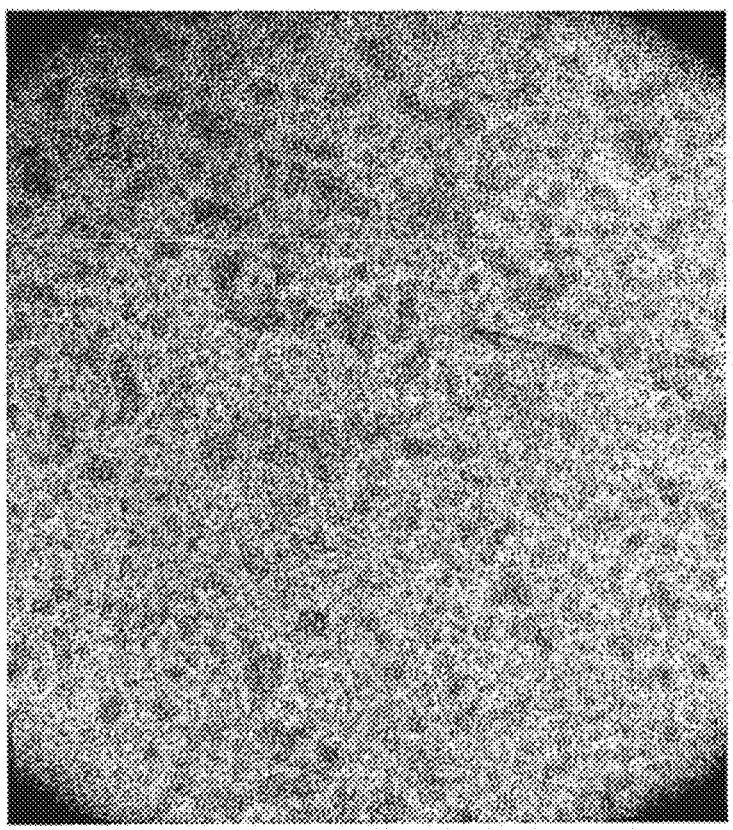
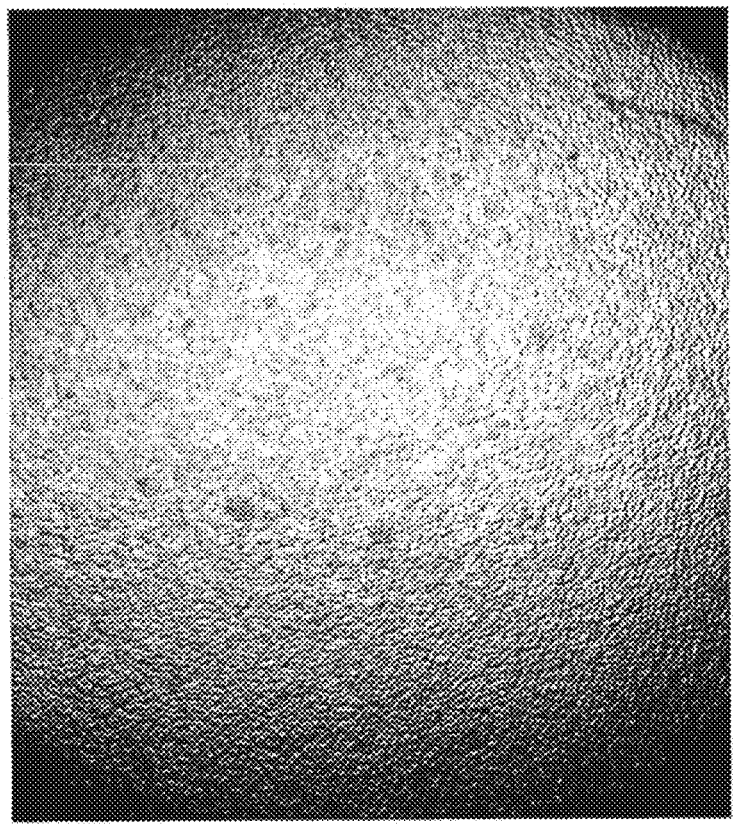
FIG. 33

HIGH THROUGHPUT MINIATURIZED ASSAY SYSTEM AND METHODS

BACKGROUND OF THE INVENTION

The present invention generally relates to the fields of biology, chemistry, and biochemistry and, more particularly, to apparatuses and methods for performing biological, biochemical, and chemical assays in small volumes. In the fields of biology, chemistry, and biochemistry, subtle changes to a molecule or cell in a reaction can often impact the results of reactions or assays. For example, changing a single amino acid (e.g., an alanine to a serine) in a polypeptide molecule or changing the growth conditions of a cell (e.g., growth in the presence of 10% fetal bovine serum versus 5% fetal bovine serum) can affect how the polypeptide or cell responds in a given reaction (e.g., whether or not the polypeptide binds to a specific binding agent or whether the cell responds to a growth factor).

Microtiter plates have been used for decades to enable the multiple reactions in small volume for applications including high-throughput screening. For example, one commonly used immunological assay, the Enzyme-linked immunosorbent assay or "ELISA" can be used to determine if a member of a binding agent/ligand pair is present in a sample, and, if present, how much is present. For example, one member of the binding agent/ligand pair (e.g., an antibody) can be immobilized to the bottom of the multiple wells on a microtiter plate (e.g., through non-specific adsorption of the antibody into the wells of the plate), and then multiple samples can be assessed as to the presence and/or concentration of the antibody's specific ligand by adding each different sample to one of the wells of the microtiter plate and then detecting binding of the sample to the well (e.g., using a detectably labeled antibody specific for the ligand).

Standard microtiter plates are commercially available from numerous manufacturers (e.g., Thermo Fisher Scientific, Waltham, Mass.) and can be made from numerous different materials (see, e.g., Bouche, F B et al., Clinical Chemistry 48: 378, 380, 2002). However, standard microtiter plates have several limitations. Most relevantly, they are limited by the number of wells on the plate. To increase the number of reactions that can be run (e.g., increase the number of samples that can be tested at the same time), the number of wells on a single plate can vary from 96 wells to 1536 wells per plate.

Recently, in the field of biology and biochemistry, DNA microarrays and protein microarrays have been employed to increase still further the number of different reactions that can be performed simultaneously. DNA microarrays are made by adhering DNA probes (e.g., single-stranded probes) to the surface of a chip or slide (e.g., made of glass or silicon) in an array of dots or spots. Different samples of DNA are then added to each of the spots and screened for the ability to bind the spots (e.g., through hybridization of a nucleic acid in the sample to the surface-bound probe). Detection of binding can then be made, for example, by fluorescent or chemical means (which, in some cases, is preceded by amplification of the bound nucleic acid molecules to enhance detection). DNA microarray technology is well known (see, e.g., U.S. Pat. Nos. 5,700,637; 7,323,555; 6,862,363; 7,414,117; and 7,359,537).

As those of skill in the art would appreciate, there are fundamental differences between microarrays and microtiter plates. In microtiter plates, a reaction in an individual well can be carried out independently regardless of a reaction in the neighboring wells. In contrast, the active spots (similar to 'wells' of a microtiter plate) in microarrays are usually exposed to a common solution. Unlike microtiter plates, microarrays do not offer any capability by which an individual spot can be exposed to a different solution during a repeated process of addition, incubation, and washing.

Protein arrays on glass slides have also been described (see Arenkov et al., Anal. Biochem 278: 123-131, 2000; Guschin et al., Anal. Biochem. 250: 202-211, 1997; MacBeath and Schreiber, Science 289: 1760-1763, 2000) as well as protein arrays on microwell or nanowell chips (see Zhu and Snyder, Curr. Opin. Chem. Biol. 5(1):40-45, 2001). However, in addition to having the same limitations as DNA microarrays, protein arrays have additional challenges. For example, complex chemicals, such as proteins and other non-nucleic acid biological molecules (e.g., fatty acids and carbohydrates), are more difficult to use in microarrays for multiple reactions. This is due to a variety of factors including, for example, the storage and binding requirements of the molecules (e.g., storage may be preferable at $-20°$ C. while binding may be preferable at $37°$ C. For these reasons, protein microarrays are generally less specific than assays such as ELISAs that use microtiter plates.

Accordingly, there is a need for a solution to running multiple reactions that can combine the specificity of microtiter plate assays with the microarray's high throughput capabilities.

SUMMARY OF THE INVENTION

Method for Manufacturing an Array Plate

In one aspect, the invention provides a method for manufacturing an array plate, the method comprising: providing a first structure, the first structure including a sheet layer with a plurality of discrete through holes; pressing the first structure against a first surface of a mold; providing a heated plastic material into the mold; and cooling the plastic material to form a second structure so that the first structure and the second structure are coupled, the second structure including a base layer and one or more vertical structures along a periphery of the base layer, adjacent a first surface of the base layer, wherein at least a portion of a first surface of the sheet layer of the first structure is exposed from the second structure, and a second surface of the sheet layer, opposite to the first surface of the sheet layer, is embedded in the base layer of the second structure adjacent the first surface of the base layer.

In some embodiments, the sheet layer includes at least 50% of fluorocarbon by weight. In some embodiments, the sheet layer includes at least 90% of fluorocarbon by weight.

In some embodiments, the plastic material includes polycarbonates. In some embodiments, the plastic material includes cyclic olefin polymer or copolymer. In some embodiments, the plastic material of the second structure is optically transparent.

In some embodiments, pressing the first structure against the first surface of the mold includes pressing the first surface of the sheet layer against the first surface of the mold with a plurality of pins at least on the second surface of the sheet layer.

In some embodiments, the method further comprises providing vacuum suction on the first surface of the sheet layer.

In some embodiments, the method further comprises coupling a third structure with at least the second structure over at least a portion of the one or more vertical structures, the third structure including one or more side walls.

In some embodiments, the one or more vertical structures of the second structure include a plurality of pins vertically protruding from the rest of the one or more vertical structures.

In some embodiments, the method includes: molding the third structure over at least a portion of the one or more vertical structures with a second mold so as to couple the second structure and the third structure; and removing a combination of the second structure and the third structure from the second mold by pushing respective locations on the third structure that correspond to the plurality of pins of the second structure.

In some embodiments, the one or more side walls are made of a plastic material that has a glass transition temperature lower than the glass transition temperature of the second structure.

In some embodiments, the one or more vertical structures include one or more side walls.

In some embodiments, the one or more side walls are made of a material that has Shore A hardness of 85 or less. In some embodiments, the one or more side walls each have an inner surface, an outer surface, a bottom adjacent the sheet layer of the first structure, and a top surface opposite the bottom, and a respective side wall of the one or more side walls includes one or more lips on the top surface, at least one of the one or more lips aligned with the inner surface of the respective side wall. In some embodiments, the one or more side walls each have an inner surface, an outer surface, a bottom adjacent the sheet layer of the first structure, and a top surface opposite the bottom, and a respective side wall of the one or more side walls includes one or more vertical indentations along the outer surface of the respective side wall. In some embodiments, the one or more side walls are made of a hydrophobic material of a surface tension lower than 35 dynes/cm. In some embodiments, the one or more side walls each have an inner surface, an outer surface, a bottom adjacent the sheet layer of the first structure, and a top surface opposite the bottom, and the inner surface of a respective side wall of the one or more side walls is coated to expose a hydrophobic surface of a surface tension lower than 35 dynes/cm.

In some embodiments, the second structure includes a plurality of holding locations, and the method comprises aligning the first structure and the second structure so that the plurality of discrete through holes defined in the sheet layer of the first structure is offset from the plurality of holding locations in the second structure.

In some embodiments, the mold is configured so that a top surface of the sheet layer of the first structure is aligned with a top surface of the base layer of the second structure. In some embodiments, the mold is configured so that a top surface of the sheet layer of the first structure is above a top surface of the base layer of the second structure. In some embodiments, the mold is configured so that a top surface of the sheet layer of the first structure is below a top surface of the base layer of the second structure.

In some embodiments, the first surface of the mold has one or more of: a plurality of indentations and a plurality of protrusions corresponding to the plurality of discrete through holes defined in the sheet layer.

In some embodiments, at least one of the side walls include one or more handles, each handle comprising a plurality of parallel fins.

In some embodiments, the method further comprises coating a portion of the second structure with oil. In some embodiments, the method further comprises coating a portion of the first surface of the sheet layer of the first structure with oil. In some embodiments, the oil is selected from the group consisting of a mineral oil, a silicone oil, a hydrocarbon compound, a hydroperfluoro carbon compound and a perfluorocarbon compound.

Apparatus

In one aspect, the invention provides an apparatus comprising an array plate manufactured by a method disclosed herein.

In one aspect, the invention provides an apparatus, comprising: a first structure, the first structure including a sheet layer with a plurality of discrete through holes; a second structure coupled to the first structure, the second structure including a base layer and one or more vertical structures along a periphery of the base layer, adjacent a first surface of the base layer, wherein at least a portion of a first surface of the sheet layer of the first structure is exposed from the second structure, and a second surface of the sheet layer, opposite to the first surface of the sheet layer, is embedded in the base layer of the second structure adjacent the first surface of the base layer.

In some embodiments, the sheet layer is formed by deposition of perfluorocarbon. In some embodiments, the sheet layer includes at least 96 discrete through holes. In some embodiments, the sheet layer includes at least 384 discrete through holes. In some embodiments, the sheet layer includes at least 50% of fluorocarbon by weight. In some embodiments, the sheet layer includes at least 90% of fluorocarbon by weight.

In some embodiments, the second structure includes polycarbonates. In some embodiments, the second structure includes cyclic olefin polymer or copolymer. In some embodiments, the second structure is made of an optically transparent plastic material.

In some embodiments, the second structure is coupled to the first surface by molding the second structure over the first structure.

In some embodiments, the sheet layer includes one or more indentations formed by vacuum suction.

In some embodiments, the apparatus further comprises a third structure coupled with at least the second structure over at least a portion of the one or more vertical structures, the third structure including one or more side walls. In some embodiments, the one or more vertical structures of the second structure include a plurality of pins vertically protruding from the rest of the one or more vertical structures. In some embodiments, the plurality of pins has an elastic modulus higher than an elastic modulus of the one of more side walls of the third structure.

In some embodiments, the one or more vertical structures include one or more side walls.

In some embodiments, the one or more side walls are made of a material that has Shore A hardness of 85 or less. In some embodiments, the one or more side walls each have an inner surface, an outer surface, a bottom adjacent the sheet layer of the first structure, and a top surface opposite the bottom, and a respective side wall of the one or more side walls includes one or more lips on the top surface, at least one of the one or more lips aligned with the inner surface of the respective side wall. In some embodiments, the one or more side walls each have an inner surface, an outer surface, a bottom adjacent the sheet layer of the first structure, and a top surface opposite the bottom, and a respective side wall of the one or more side walls includes one or more vertical indentations along the outer surface of the respective side wall. In some embodiments, the one or more side walls are made of a hydrophobic material of a surface tension lower than 35 dynes/cm. In some embodiments, the one or more side walls each have an inner surface, an outer surface, a bottom adjacent the sheet layer of the first structure, and a top surface opposite the bottom, and the inner surface of a respective side wall of the one or more side walls is coated to expose a hydrophobic surface of a surface tension lower than 35 dynes/cm. In some embodiments, the one or more side walls are made of a plastic material that has a glass transition temperature lower than the glass transition temperature of material for the second structure.

In some embodiments, the second structure includes a plurality of holding locations, and the first structure and the second layer are aligned so that the plurality of discrete through holes defined in the sheet layer of the first structure is offset from the plurality of holding locations in the second structure.

In some embodiments, the mold is configured so that a top surface of the sheet layer of the first structure is aligned with a top surface of the base layer of the second structure. In some embodiments, the mold is configured so that a top surface of the sheet layer of the first structure is above a top surface of the base layer of the second structure. In some embodiments, the mold is configured so that a top surface of the sheet layer of the first structure is below a top surface of the base layer of the second structure.

In some embodiments, the first surface of the mold has one or more of: a plurality of indentations and a plurality of protrusions corresponding to the plurality of discrete through holes defined in the sheet layer.

In some embodiments, at least one of the side walls includes one or more handles, each handle comprising a plurality of parallel fins.

In some embodiments, the apparatus further comprises a layer of oil coating a portion of the second structure. In some embodiments, the apparatus further comprises a layer of oil coating a portion of the first surface of the sheet layer of the first structure. In some embodiments, the oil is selected from the group consisting of a mineral oil, a silicone oil, a hydrocarbon compound, a hydroperfluorocarbon compound and a perfluorocarbon compound.

In some embodiments, the apparatus further comprises a grid. In some embodiments, the grid includes a plurality of through holes aligned with at least some of the plurality of discrete through holes in the sheet layer of the first structure.

In one aspect, the invention provides an apparatus, comprising a base layer and one or more vertical structures along a periphery of the base layer, adjacent a first surface of the base layer.

In some embodiments, the first surface includes a plurality of immobilization areas of a first set of surface properties and the remaining area of a second set of surface properties, the second set of surface properties distinct from the first set of surface properties. In some embodiments, the first surface includes at least 96 immobilization areas. In some embodiments, the first surface includes at least 384 immobilization areas. In some embodiments, the plurality of immobilization areas has a first surface energy and the remaining area has a second surface energy distinct from the first surface energy. In some embodiments, the plurality of immobilization areas includes a hydrophillic surface and the remaining area includes a hydrophobic surface.

In some embodiments, the apparatus further comprises a layer of oil coating a portion of the first surface. In some embodiments, the apparatus further comprises a layer of oil coating a portion of the remaining area. In some embodiments, the apparatus further comprises a layer of oil coating a portion of the plurality of immobilization areas. In some embodiments, the oil is selected from the group consisting of a mineral oil, a silicone oil, a hydrocarbon compound, a hydroperfluorocarbon compound and a perfluorocarbon compound.

In some embodiments, the apparatus further comprises a grid. In some embodiments, the grid includes a plurality of through holes aligned with at least some of the plurality of immobilization areas. In some embodiments, the grid is configured to contact the base layer. In some embodiments, the grid is configured not to contact the base layer. In some embodiments, the grid is removable from the apparatus.

In some embodiments, at least one of the one or more vertical structures includes an inner wall and an outer wall, and the inner wall and the outer wall are parallel to each other.

In some embodiments, the apparatus further comprises one or more alignment indentations.

In some embodiments, the apparatus further comprises one or more handles.

In some embodiments, the apparatus further comprises a lid.

In some embodiments, the base layer has a flatness of at most 400 µm. In some embodiments, the base layer is optically transparent for a wavelength range selected from the group consisting of: 250-900 nm, 35-850 nm, 400-800 nm, 450-800 nm, and 500-800 nm. In some embodiments, the base layer is optically opaque for a wavelength range selected from the group consisting of: 250-900 nm, 350-850 nm, 400-800 nm, 450-800 nm, and 500-800 nm. In some embodiments, the base layer includes one or more feet.

In some embodiments, the apparatus further comprises an orientation reference. In some embodiments, a portion of the one or more vertical structures and/or the base layer is removed to indicate an orientation of the apparatus.

In some embodiments, the apparatus further comprises a plate identification feature. In some embodiments, one or more portions of the base layer or the second structure are removed for identifying the apparatus.

Grid

In one aspect, the invention provides a grid for use with an apparatus disclosed herein.

Lid

In one aspect, the invention provides a lid for use with an apparatus disclosed herein.

Device for Washing an Apparatus

In one aspect, the invention provides a device for washing an apparatus disclosed herein, wherein the apparatus has an array of liquid droplets and an immiscible liquid on the base layer, the device comprising: a plate holder for holding the apparatus, wherein the plate holder is configured to hold and rotate the apparatus at a plurality of angles.

In some embodiments, the device further comprises a shaker coupled with the plate holder, wherein the shaker is configured to shake the apparatus held in the plate holder. In some embodiments, the shaker is configured to shake the apparatus at a frequency selected from the group consisting of 1-1000 rpm, 5-500 rpm, 10-100 rpm, 10-50 rpm, 15-40 rpm, and 18-40 rpm. In some embodiments, shaking the apparatus includes rotating the apparatus along a circular path having a radius selected from the group consisting of: 1-200 mm, 1-100 mm, 2-80 mm, 3-50 mm, 5-40 mm, and 10-35 mm. In some embodiments, shaking the apparatus includes moving the apparatus along a linear path having a distance selected from the group consisting of: 1-200 mm, 1-100 mm, 2-80 mm, 3-50 mm, 5-40 mm, and 10-35 mm.

In some embodiments, the device further comprises: a cover placing mechanism for placing a cover over the apparatus held in the plate holder. In some embodiments, the cover includes one or more holes for draining a substantial portion of the immiscible liquid.

In some embodiments, the plate holder is configured to receive the apparatus at a first angle and rotate the apparatus to a second angle for draining a substantial portion of the immiscible liquid, the second angle being distinct from the first angle. In some embodiments, the difference between the first angle and the second angle is selected from the group consisting of: 30 degrees, 60 degrees, 90 degrees, and 120 degrees.

In some embodiments, the plate holder is configured to receive the apparatus at a first angle and rotate the apparatus to a third angle for providing a wash fluid into a cavity formed by the apparatus and the cover. In some embodiments, the difference between the first angle and the third angle is selected from the group consisting of: 30 degrees, 60 degrees, 90 degrees, and 120 degrees.

In some embodiments, the device further comprises a wash fluid dispenser configured to provide a wash fluid into a cavity formed by the apparatus and the cover.

In some embodiments, the plate holder is configured to receive the apparatus at a first angle and rotate the apparatus to a fourth angle for draining a substantial portion of the wash fluid, the fourth angle being distinct from the first angle. In some embodiments, the plate holder is configured to rotate the apparatus to the fourth angle while draining the substantial portion of the wash fluid. In some embodiments, the difference between the first angle and the fourth angle is selected from the group consisting of: 30 degrees, 60 degrees, 90 degrees, and 120 degrees.

In some embodiments, the device further comprises an immiscible liquid dispenser configured to provide an immiscible liquid onto the apparatus.

In some embodiments, the device further comprises an apparatus identifier component.

In some embodiments, the device further comprises a plate scanner. In some embodiments, the plate scanner includes an optical scanner.

In some embodiments, the device further comprises an incubator.

Device for Providing Reagents to an Apparatus

In one aspect, the invention provides a device for providing reagents to an apparatus disclosed herein, the device comprising: a plate holder for holding the apparatus; and a reagent dispenser coupled to provide one or more reagents to one or more liquid droplets of the array of liquid droplets on the apparatus.

In some embodiments, the device further comprises a shaker coupled with the plate holder for shaking the apparatus.

In some embodiments, the device (for providing reagents to an apparatus) further comprises the device for washing the apparatus described herein.

In some embodiments, the shaker is configured to shake the apparatus at a rotational speed selected from the group consisting of 1-10,000 rpm, 10-5000 rpm, 100-3000 rpm, 500-2000 rpm, 750-1500 rpm, and 800-1200 rpm. In some embodiments, shaking the apparatus includes rotating the apparatus along a circular path having a radius selected from the group consisting of: 1-200 mm, 1-100 mm, 2-80 mm, 3-50 mm, 5-40 mm, and 10-35 mm.

Method of Using a Device (for Washing an Apparatus)

In one aspect, the invention provides a method of using a device (for washing an apparatus) disclosed herein, comprising: providing an apparatus disclosed herein on the plate holder of the device; and initiating the device.

In some embodiments, the method further comprises removing the apparatus from the plate holder of the device.

Method of Washing an Apparatus

In one aspect, the invention provides a method of washing an apparatus disclosed herein, wherein the apparatus has an array of liquid droplets and an immiscible liquid on the base layer, the method comprising: adding a wash buffer onto the apparatus; and draining a substantial portion of the wash buffer from the apparatus.

In some embodiments, the method further comprises: prior to adding the wash buffer, draining a substantial portion of the immiscible liquid from the apparatus.

In some embodiments, the method further comprises: after adding the wash buffer and prior to draining the substantial portion of the wash buffer, shaking the apparatus.

In some embodiments, the method further comprises: after draining the substantial portion of the wash buffer, adding an immiscible liquid onto the apparatus.

In some embodiments, the wash buffer is selected from the group consisting of: phosphate buffered saline, phosphate buffered saline with Tween 20, and tris buffered saline.

Method of Providing Reagents to an Apparatus

In one aspect, the invention provides a method of providing reagents to an apparatus disclosed herein, the method comprising: providing one or more reagents to one or more liquid droplets of the array of liquid droplets on the apparatus.

In some embodiments, the method further comprises: after providing the one or more reagents to the one or more liquid droplets, placing the apparatus on the plate holder of the device for providing reagents to the apparatus described herein or the device for washing the apparatus described herein; and initiating the device.

In some embodiments, the method further comprises removing the apparatus from the plate holder of the device.

In some embodiments, the method further comprises washing the apparatus.

Method of Processing a Sample

In one aspect, the invention provides a method of processing a sample comprising: a) providing a processing compartment comprising a reservoir and a flat surface comprising a hydrophobic surface with an array of hydrophilic immobilization areas; b) dispensing a sample at a plurality of the areas; c) filling the reservoir with an immiscible medium; d) tilting the processing compartment to remove all but a thin layer of the immiscible medium that is retained on the flat surface; e) adding a first reagent to the processing compartment; and f) tilting the processing compartment to remove the first reagent.

In some embodiments, a plurality of the hydrophilic immobilization areas each comprise a different biological moiety. In some embodiments, a plurality of the hydrophilic immobilization areas each comprise the same biological moiety. In some embodiments, the biological moieties are antibodies. In some embodiments, the biological moieties are proteins. In some embodiments, the biological moieties are nucleic acids. In some embodiments, the biological moieties are cells. In some embodiments, the biological moieties are covalently attached to the hydrophilic immobilization areas.

In some embodiments, steps b)-f) are optionally repeated.

In some embodiments, the biological moieties are primary antibodies, the sample comprises a target analyte that binds to the primary antibodies, and the first reagent is a labeled secondary antibody that also binds to the target analyte, and the method further comprises detecting the label as an indicator of the presence or absence of the target analyte.

In some embodiments, the biological moieties are protein antigens, the sample comprises a target antibody that binds to the protein antigens, and the first reagent is a labeled secondary antibody that also binds to the target antibody, and the method further comprises detecting the label as an indicator of the presence or absence of the target antibody.

In some embodiments, the biological moieties are nucleic acid probes, the sample comprises a labeled target nucleic acid sequence that binds to the nucleic acid probes, and the method further comprises detecting the label as an indicator of the presence or absence of the target nucleic acid sequence.

In some embodiments, the biological moieties are nucleic acid probes, the sample comprises a target nucleic acid sequence that hybridizes to the nucleic acid probes, and the first reagent is a label probe that also hybridizes to the target sequence and the method further comprises detecting the label as an indicator of the presence or absence of the target nucleic acid sequence.

Method of Culturing Cells

In one aspect, the invention provides a method of culturing cells comprising: a) providing a flat surface comprising a hydrophobic surface with an array of hydrophilic immobilization areas, a plurality of the areas comprising cells disposed on the areas and a cell culture medium, wherein the surface is covered by an immiscible medium; b) incubating the surface at a temperature suitable for cell culture.

In some embodiments, the method further comprises replacing the cell culture medium by draining the cell culture medium and replacing with fresh cell culture medium. In some embodiments, the replacing is done using a pipette. In some embodiments, the replacing is done by tilting the surface to drain the cell culture medium and adding new cell culture medium.

In some embodiments, the cells are adherent cells. In some embodiments, the cells are non-adherent cells.

In some embodiments, the hydrophilic immobilization areas are coated with a biomaterial prior to the addition of cells. In some embodiments, the biomaterial is selected from the group consisting of collagen I, collagen II, collagen IV, poly-D-lysine (PDL), gelatin, laminin, and combinations thereof.

In some embodiments, the method further comprises adding a transfection nucleic acid to a plurality of the immobilization areas and incubating at a suitable temperature.

In some embodiments, the transfection nucleic acids are added to the immobilization areas prior to the addition of cells. In some embodiments, the transfection nucleic acid is DNA. In some embodiments, the transfection nucleic acid is siRNA.

In some embodiments, the method further comprises assaying the cells to determine whether transfection has occurred.

In some embodiments, the method further comprises: c) adding a compound to at least one of the areas; d) incubating the surface at a temperature suitable for cell culture; and e) detecting the effect of the compound on the cells.

BRIEF DESCRIPTION OF THE DRAWINGS

FIG. 4 shows the light microscopy images of HeLa cell morphology before and after docetaxel treatment, pursuant to the mitotic index assay described in Example 4. The top row of images is at 10× objective while the bottom row of images is at 32× objective.

FIG. 11 is a perspective view of an exemplary array plate in accordance with some embodiments.

FIG. 13C-1 is a partial sectional view of the exemplary array plate corresponding to a portion of the cross-sectional view illustrated in FIG. 13C in accordance with some embodiments.

FIG. 13E-1 is a partial sectional view of the exemplary array plate corresponding to a portion of the cross-sectional view illustrated in FIG. 13E in accordance with some embodiments.

FIG. 13G-1 is a partial sectional view of the exemplary array plate corresponding to a portion of the cross-sectional view illustrated in FIG. 13G in accordance with some embodiments.

FIGS. 16A-16D are flow charts representing a method of making an array plate in accordance with some embodiments.

FIGS. 17A-17D provide data obtained from a cell-based assay run with PBMCs on the Curiox 96 well plate as described in Example 9. In particular, FIG. 17A provides the cell count obtained for each of the four quadrants in Reads 1, 2, and 3, respectively. FIG. 17B shows the MitoTracker signal for each of the four quadrants in Reads 1, 2, and 3, respectively. FIG. 17C provides the sample images obtained from the quadrant having 5K cells/well with CellTak and FIG. 17D shows the composite image generated from the superimposition of the images for Reads 1, 2, and 3.

FIG. 21 provides PBMC cell images (based on DAPI and Mitotracker signals) from the same field in the same well prior to the first wash, after 3 washes, and after 6 washes, respectively. Some movement of the PBMCs was detected but loss from washing proved minimal.

FIG. 33 shows the retention of B cells (suspension cells) after a washing step is performed with an array plate of the present invention.

DETAILED DESCRIPTION OF THE INVENTION

Figure 1:
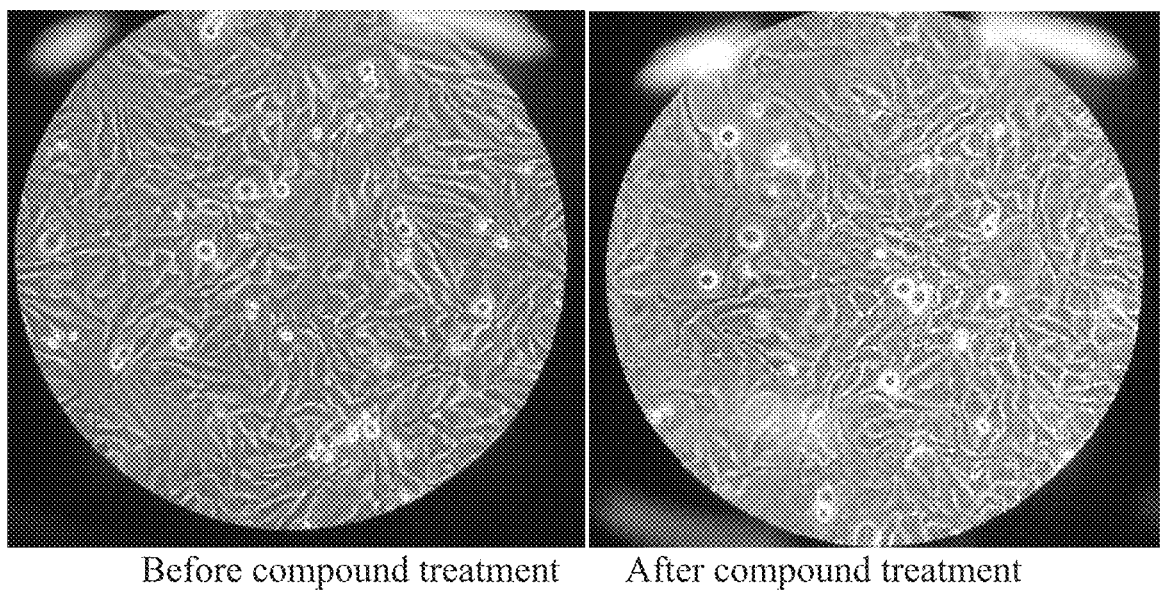
FIG. 1 provides two light microscopy images (as observed under 40× objective) of HeLa-LC3-GFP cell morphology, i.e. before and after compound treatment pursuant to the autophagy assay described in Example 3.
Figure 2:
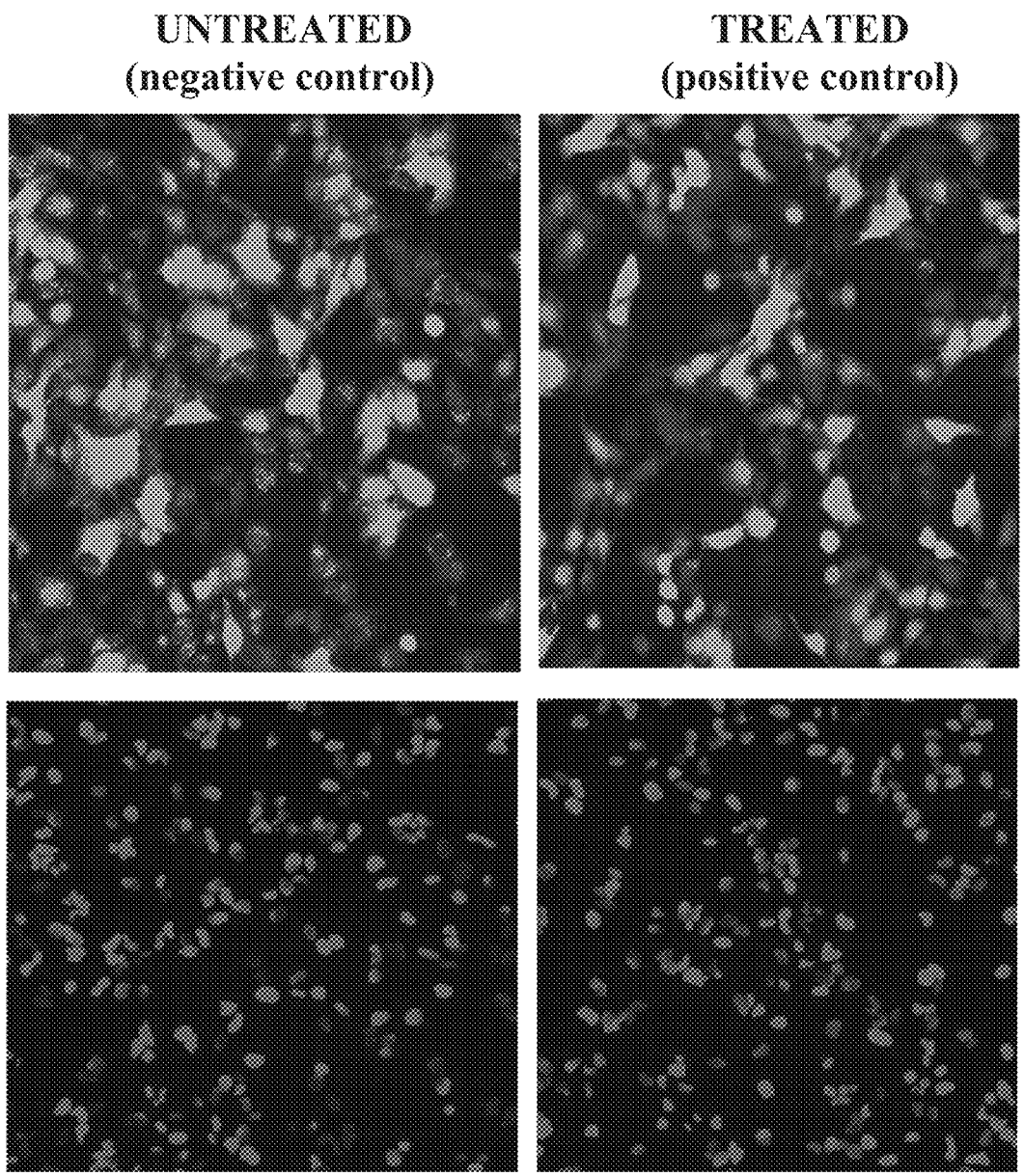
FIG. 2 provides four images of HeLa-LC3-GFP cells (as observed under 40× objective), the top row visualized with GFP nuclear staining and the bottom row visualized with ToPro-3 dye, pursuant to the autophagy assay described in Example 3. Cells imaged in the left column and right column were untreated and treated, respectively, with antagonist compound.
Figure 3:
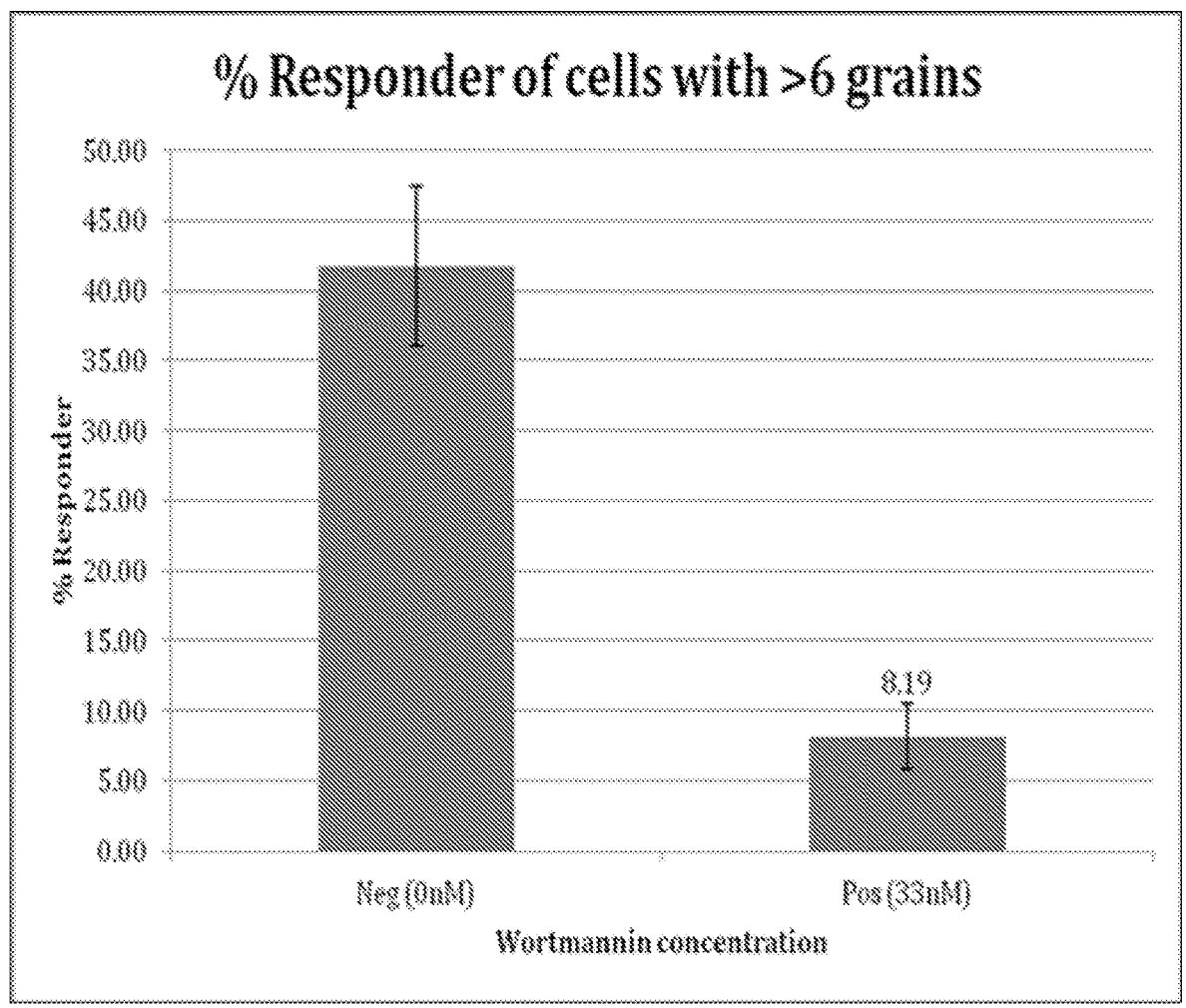
FIG. 3 is a plot of the percentage of HeLa-LC3-GFP cell responders (>6 grains per cell) when exposed to 0 nM and 33 nM of Wortmannin treatment, pursuant to the autophagy assay described in Example 3. Each column represents the average of 192 wells, in which the average value is labeled on top of column, and error bars represent standard deviations.
Figure 5:
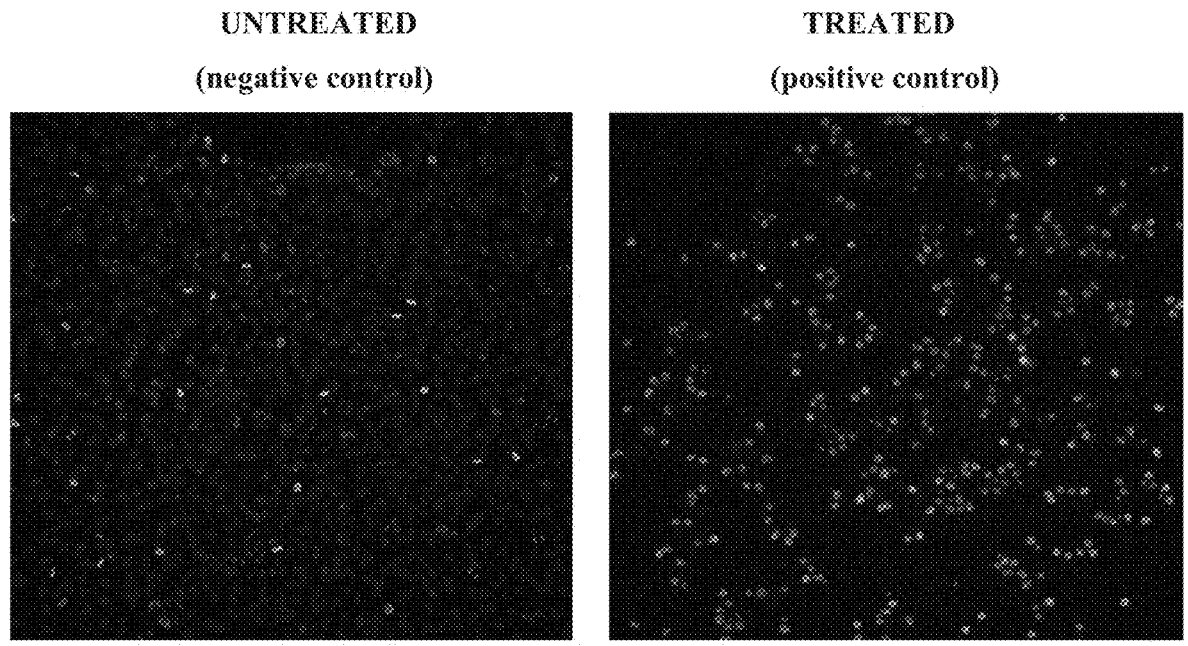
FIG. 5 shows four images of HeLa-LC3-GFP cells, the top row visualized with DyLight-488 nuclear staining and the bottom row visualized with Hoechst dye nuclear staining, pursuant to the mitotic index assay described in Example 4. Cells imaged in the left column and right column were untreated and treated, respectively, with docetaxel (20× objective).
Figure 6:
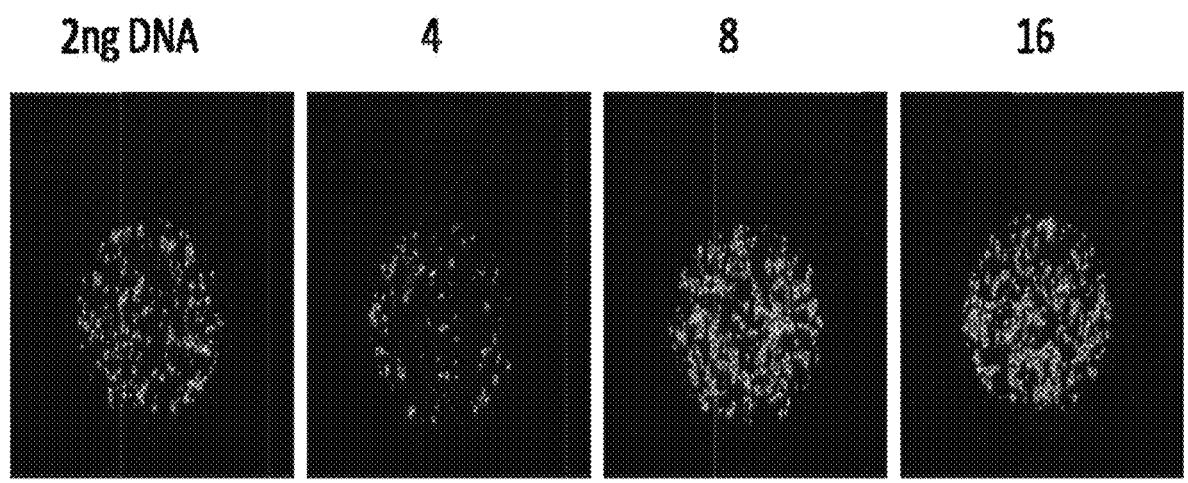
FIG. 6 shows the transfection of cells with GFP-encoding DNA achieved at four different concentrations of exogenous DNA, ranging from 2 ng to 8 ng, pursuant to the transfection protocol described in Example 6.
Figure 7:
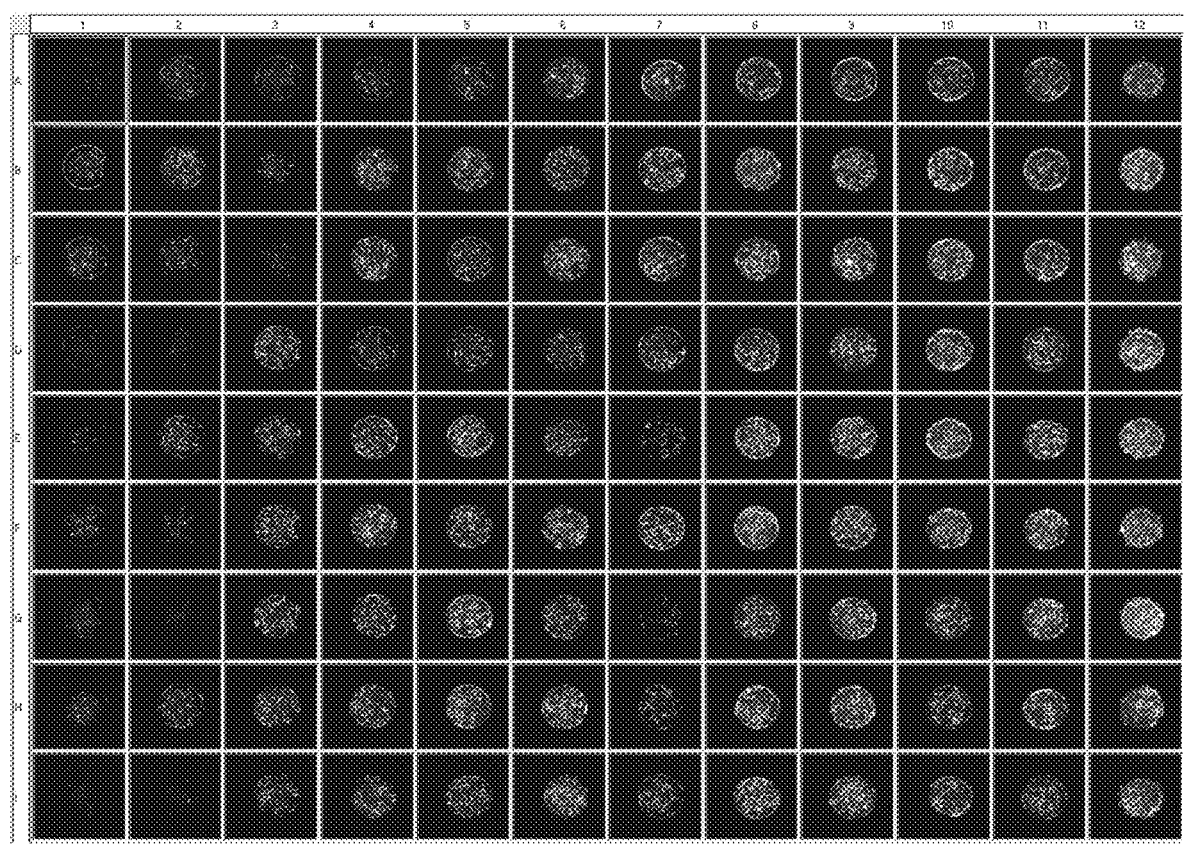
FIG. 7 shows the transfection of cells with GFP-encoding DNA at various discrete locations on a DropArray™ plate, pursuant to the reverse transfection protocol described in Example 6.

The present invention provides a "well-less" array plate that eliminates the need for standard wells formed by physical walls. The plate employs hydrophobic, hydrophilic interactions, surface tension, and a halogenated hydrocarbon, e.g. perfluorocarbon, to create a patterned surface that can hold and accommodate multiple cell-based assays, each performed in its own discrete area of the plate with reduced risk of cross-contamination. Immiscibility of the perfluorocarbon with the liquid samples and/or reagents, together with its hydrophobic interaction with the hydrophobic surface surrounding the immobilization area, leads to a film formation over each droplet of liquid sample and/or reagents. The perfluorocarbon film around each droplet establishes a barrier to evaporation and to crosstalk between distinct droplets. The array plates may be further functionalized and/or coated to optimize the culture conditions for specific cell lines. Also provided is a fluidics handling apparatus that uses gravity and vacuum forces to effect mixing, washing, and drainage of the hydrocarbon or assay reagents and/or the perfluorocarbon fluid.

This novel platform makes possible the performance of cell-based assays at drastically reduced sample and/or reagent volumes, e.g. 2-3 µl sample/virtual well. Attendant with reduced sample and reagent volumes are shorter incubation times, less time to reach reaction equilibrium, and significant cost-savings. For instance, the reduced cell requirement in immunoassays can, depending on statistical relevance considerations, be 500-1000 or 500-700 cells per data point or less, compared to the 3,000-10,000 cells per data point needed for conventional array plates. Since cells can be kept on the plate bottom through surface tension and the hydrophobic area surrounding the assay-containing drop, this platform facilitates handling of semi-adherent and suspension cells and eliminates the need to spin down cell samples associated with traditional array plates, resulting in significant benefits. The unique fluid dynamic by which contents of each assay are held in the hydrocarbon droplet and to the plate bottom also works in conjunction with the gentle whole-plate washing mechanism described herein to minimize cell loss, human error, machine error, and thereby enhance reproducibility and quality of results. Since the conventional plate layout can be implemented by the present invention, the well-less plate can be adapted to standard SBS-96, SBS-384, SBS-1536 well formats and is integratable in existing high-throughput systems and compatible with conventional microplate imagers and dispensers.

In contrast to conventional high throughput screening systems, which are limited to running homogeneous fluorescent assays, screening systems that use the presently described array plates have numerous advantages. They can be used with a wide range of assay types, e.g., heterogeneous assays, capture and wash assays, kinetic and flash detection assays. Those of skill in the art would appreciate that the presently described array plates can be applied in a variety of biochemical and cellular assays (including tissue-based, whole organism, and 2D and 3D systems with dimensions less than 8 mm across), particularly assays where it would be advantageous to minimize the total volume of reagents, where long incubations are involved, or where washing is required. The plates can be configured as a support surface of the assay or as an active part of the assay, e.g. a selective filter, or as an active element, e.g. one used for temperature control, electrical or magnetic stimulation or regulation. The array plates of the present invention are compatible with many detection methods such as: different modes of fluorescence (e.g., epi-fluorescence, fluorescence resonance energy transfer, homogeneous time resolved fluorescence, Aphalisa™, etc.), capillary electrophoresis, fluorescence activated cell sorting (FACS), mass spectroscopy, chemiluminescence (both glow and flash), absorbance, scattering, electroluminescence, isotope assays, as well as direct binding assays such as surface plasmon resonance (SPR), and reflective interference spectroscopy (RIPS), atomic absorption spectroscopy (AAS), optical and electron microscopy, electrophysiology, impedance measurements, membrane transfer/partitioning measurements, and others. The elimination of physical walls also reduces: often wasteful accumulation of cells near the edges, optical interference during imaging, formation of air bubbles or plugs of liquids trapped within wells, and edge effect from evaporation.

DEFINITIONS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range.

Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. In some embodiments, the definition of terms used herein is according to IUPAC. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The terms "individual," "subject," and "patient," used interchangeably herein, refer to a mammal, including, but not limited to, murines, simians, humans, mammalian farm animals, mammalian sport animals, and mammalian pets. In preferred embodiments, the individual is a human.

As used herein, the term "immiscible liquid" or "immiscible medium" refers to a fluid that is immiscible with a liquid droplet (e.g., hydrophilic liquid, such as water or a tissue culture media, or hydrocarbon-based liquids). Non-limiting examples of immiscible liquid useful in the present invention include the perfluorinated hydrocarbon liquid sold under the trademark Fluorinert™ name by the 3M Corporation (St. Paul, Minn., USA) and the immiscible fluid sold by Curiox Biosystems (Singapore), e.g. under the trademarks Rinsing Oil™, Incubation Oil™, or Sealing Fluid™. Some immiscible liquids, such as perfluorinated hydrocarbon liquid, are hydrophobic and oleophobic, which repels not only aqueous solutions but also hydrocarbon solutions.

The term "sample" as used herein refers to a biological sample obtained for the purpose of evaluation in vitro or ex vivo. In the context of the present invention, the sample may comprise any number of things, including, but not limited to, bodily fluids (including, but not limited to, blood, urine, serum, lymph, saliva, cerebrospinal fluid, synovial fluid, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., J Cell Physiol. (2007) 210(2):279-89; Osada et al., Carcinogenesis. (2007) 28(1):2-12; and Mattes et al., Am J Respir Cell Mol. Biol. (2007) 36(1):8-12, each of which is incorporated herein by reference in its entirety).

The term "processing compartment" as used herein refers to structure that includes a reservoir and a flat surface having a hydrophobic surface with an array of hydrophilic immobilization areas. In some embodiments, the flat surface constitutes part of the bottom surface of the reservoir. In other embodiments, the flat surface does not form a part of the bottom surface of the reservoir but is instead positioned within the reservoir. To illustrate, the flat surface could be part of a glass slide that is positioned in the reservoir. In some embodiments, the glass slide is coupled to side walls of the reservoir.

As used herein, the term "immobilization area" refers to a discrete area of the flat surface of the processing compartment that is surrounded by a hydrophobic surface and to which a sample can be bound. In exemplary embodiments, immobilization of the sample droplet can be accomplished by one or more of the following: hydrophilic interaction of the sample droplet with the immobilization area; hydrophobic interaction of a layer of immiscible liquid over the sample droplet with the hydrophobic surface surrounding an immobilization area; and the surface tension associated with the sample droplet, hydrophobic surface, and immiscible liquid.

The term "antibody" as referred to herein includes, at a minimum, an antigen binding fragment (i.e. "antigen-binding portion") of an immunoglobulin.

The definition of "antibody" includes, but is not limited to, full length antibodies, antibody fragments, single chain antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates") and fragments and/or derivatives of each, respectively. In general, a full length antibody (sometimes referred to herein as "whole antibodies") refers to a glycoprotein which may comprise at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$ or $V_K$) and a light chain constant region. The light chain constant region is comprised of one domain, $C_L$. The $V_H$ and $V_L/V_K$ regions can be further subdivided into regions of hypervariability, termed complementarity determining regions (CDR), interspersed with regions that are more conserved, termed framework regions (FR). Each $V_H$ and $V_L/V_K$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

In one embodiment, the antibody is an antibody fragment. Specific antibody fragments include, but are not limited to, (i) the Fab fragment consisting of $V_L$, $V_H$, $C_L$ and $C_H1$ domains, (ii) the Fd fragment consisting of the $V_H$ and $C_H1$ domains, (iii) the Fv fragment consisting of the $V_L$ and $V_H$ domains of a single antibody, (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulfide bridges linking the $V_H$ and $V_L$ domains. Examples of antibody formats and architectures are described in Holliger & Hudson (2006) *Nature Biotechnology* 23(9):1126-1136, and Carter (2006) *Nature Reviews Immunology* 6:343-357, and references cited therein, all expressly incorporated by reference.

The present disclosure provides antibody analogs. Such analogs may comprise a variety of structures, including, but not limited to full length antibodies, antibody fragments, bispecific antibodies, minibodies, domain antibodies, synthetic antibodies (sometimes referred to herein as "antibody mimetics"), antibody fusions, antibody conjugates, and fragments of each, respectively.

In one embodiment, the immunogloublin comprises an antibody fragment. Specific antibody fragments include, but are not limited to (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g. prepared chemically or from hybrid hybridomas. In one embodiment, the antibody is a minibody. Minibodies are minimized antibody-like proteins comprising a scFv joined to a $C_H3$ domain. In some cases, the scFv can be joined to the Fc region, and may include some or all of the hinge regions. For a description of multispecific antibodies, see Holliger and Hudson (2006) *Nature Biotechnology* 23(9):1126-1136 and references cited therein, all expressly incorporated by reference.

By "Fab" or "Fab region" as used herein is meant the polypeptide that comprises the $V_H$, $C_H1$, $V_L$, and $C_L$ immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the $V_L$ and $V_H$ domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

The term "antigen-binding portion" of an antibody (or simply "antibody portion"), as used herein, refers to one or more fragments of an antibody that retain the ability to specifically bind to an antigen (e.g. BST1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L/V_K$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody; (vi) a dAb fragment [Ward et al. (1989) *Nature* 341:544-546], which consists of a $V_H$ domain; (vii) an isolated complementarity determining region (CDR); and (viii) a Nanobody, a heavy chain variable region containing a single variable domain and two constant domains. Furthermore, although the two domains of the Fv fragment, $V_L/V_K$ and $V_H$, are coded for by separate genes, they can be joined, using recombinant methods, by a synthetic linker that enables them to be made as a single protein chain in which the $V_L/V_K$ and $V_H$ regions pair to form monovalent molecules (known as single chain Fv (scFv); see e.g. Bird et al. (1988) *Science* 242:423-426; and Huston et al. (1988) *Proc. Natl. Acad. Sci. USA* 85:5879-5883. Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody" as used herein, is intended to refer to an antibody that is substantially free of other antibodies having different antigenic specificities (e.g. an isolated antibody that specifically binds to the BST1 is substantially free of antibodies that specifically bind antigens other than the BST1). An isolated antibody that specifically binds to the BST1 may, however, have cross-reactivity to other antigens, such as BST1 molecules from other species. Moreover, and/or alternatively an isolated antibody may be substantially free of other cellular material and/or chemicals, that is in a form not normally found in nature.

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced.

As used herein, "isotype" refers to the antibody class (e.g. IgM or IgG1) that is encoded by the heavy chain constant region genes.

Methods for detecting target analytes are provided by the present invention. By "target analyte" or "analyte" or grammatical equivalents herein is meant any molecule or compound to be detected and that can bind to a binding species, defined below. Suitable analytes include, but are not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs, cells; antibodies; antigens; cellular membrane antigens and receptors (neural, hormonal, nutrient, and cell surface receptors) or their ligands.

Suitable target analytes include biomolecules associated with: (1) viruses, including but not limited to, orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like; and (2) bacteria, including but not limited to, a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. Iamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like.

Other suitable target analytes include, but are not limited to, enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (2) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-.alpha. and TGF-.beta.), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (3) other proteins (including $\alpha$.-fetoprotein, carcinoembryonic antigen CEA, cancer markers, etc.).

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

Other suitable target analytes include metal ions, particularly heavy and/or toxic metals, including but not limited to, aluminum, arsenic, cadmium, selenium, cobalt, copper, chromium, lead, silver and nickel.

In a preferred embodiment, the methods of the invention are used to detect pathogens such as bacteria. In this embodiment, preferred target sequences include rRNA, as is generally described in U.S. Pat. Nos. 4,851,330; 5,288,611; 5,723,597; 6,641,632; 5,738,987; 5,830,654; 5,763,163; 5,738,989; 5,738,988; 5,723,597; 5,714,324; 5,582,975; 5,747,252; 5,567,587; 5,558,990; 5,622,827; 5,514,551; 5,501,951; 5,656,427; 5,352,579; 5,683,870; 5,374,718; 5,292,874; 5,780,219; 5,030,557; and 5,541,308, all of which are expressly incorporated by reference.

As will be appreciated by those in the art, a large number of analytes may be detected using the present methods; basically, any target analyte for which a binding ligand, described below, may be made may be detected using the methods of the invention. While many of the techniques described below exemplify nucleic acids as the target analyte, those of skill in the art will recognize that other target analytes can be detected using the same systems.

If required, the target analyte is prepared using known techniques. For example, the sample may be treated to lyse the cells, using known lysis buffers, electroporation, etc., with purification and/or amplification as needed, as will be appreciated by those in the art. When the target analyte is a nucleic acid, the target sequence may be amplified as required; suitable amplification techniques are outlined in PCT US99/01705, hereby expressly incorporated by reference. In addition, techniques to increase the amount or rate of hybridization can also be used; see for example WO 99/67425 and U.S. Ser. Nos. 09/440,371 and 60/171,981, all of which are hereby incorporated by reference.

A "label," as used herein, is a molecule that produces or which may be induced to produce a detectable signal. Examples of suitable labels include, but are not limited to, an organic molecule, an enzyme, a radioactive, fluorescent, and/or chromogenic moiety, a luminescent moiety, a hapten, digoxigenin, biotin, a metal complex, a metal and colloidal gold.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252 3 (1998); positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The term "nucleic acids" also encompasses peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. Similarly, due to their non-ionic nature, hybridization of the bases attached to these backbones is relatively insensitive to salt concentration.

I. Overview

The present invention is generally directed to the use of plates and apparatus that find use in a wide variety of biological and biochemical assays, similar to the use of microtiter plate assay systems but with some remarkable advantages. The present invention is directed to making and using array plates (sometimes referred to herein as "biochips"), that generate the array through the use of drops of aqueous biological samples on hydrophilic "spots" or "addresses" on the array plate against a background of hydrophobic surface. This allows the array plate to be covered with an oil (generally perfluorocarbon-based oil, although hydrocarbon-based oil and/or a mixture of perfluorocarbon and hydrocarbon may be used) that is immiscible with the drops of aqueous solutions at the hydrophilic locations. Surprisingly, this coating of oil keeps the reaction volumes at each location separate, and yet allows new reagents to be introduced, including assay components as well as washing reagents, for example, without disturbing the content of the virtual wells (sometimes referred to herein as "drop wells"), preventing cross contamination. Also surprising is the ability of this fluid, in at least some embodiments, to act as a barrier for reducing evaporation while allowing gas transfer.

As a general and non-limiting overview, the patterned hydrophobic/hydrophilic array plates are made as described below. The array plates are then loaded with a starting biology, which typically includes a hydrophilic material (e.g. coatings, nucleic acid or protein capture probes, cells, antibodies, etc., as is more fully described below) and the oil is applied, generally by placing the plates into appropriate washing apparatus, as is more fully described below, that comprises a reservoir into which the plate fits. When the oil is mainly composed of perfluorocarbon or fluorinated carbon materials, the array plates may be loaded with hydrocarbon-based chemicals and/or non-biological materials. The reservoir is filled with the immiscible oil. The plate is then removed from the oil and tilted at an angle, so as to remove all but a thin layer of oil on the plate's surface.

As is also more fully described below, the plates can be stored with the oil in place for a period of time; for example, to be shipped to an end user. Alternatively, the unloaded plates can be provided to the end user who can load with their particular biology and then add the oil for use.

Once the plates are ready to use, they can be placed in the reservoir that can be filled with the next reagent to be added to the virtual well. If the reagent is an aqueous reagent, it frequently exchanges out with the reagent already present in the drop well, for example to wash an unbound reagent out. The addition of oil, tilting and reagent addition can be repeated as many times as needed for the assay in question.

Depending on the desired use and the assay, the reaction can be monitored or detected in a wide variety of ways, as is described herein. For example, when biological or biochemical fluorescent assays are done, for example, the drop wells can be read using fluorescent optical readers. For some cell assays, the cells can be "sipped" from each spot and assayed using a flow cytometry apparatus or a capillary electrophoresis apparatus.

As a result, the present invention provides essentially "virtual microtiter plate wells", that allows not only any standard biologic or biochemical assay to be run in much smaller volumes with far less reagent use (and in some cases in less time), but also allows a number of novel cell based assays using small cell volumes as well as semi-adherent and non-adherent cells.

Accordingly, the present invention provides plates and apparatus for a variety of uses, including a wide variety of chemical and biochemical assays, as are all further discussed below. In some embodiments, the plates are precoated with transfection reagents.

II. Devices

Some embodiments include plates (sometimes referred to as "biochips" as discussed below) and apparatus used in a variety of assays.

Plates

Some embodiments include drop array plates that comprise solid supports with patterned hydrophobic/hydrophilic surfaces. In some embodiments, the drop array plates include porous structures. The drop array plates with the porous structures may be used in automated electrophysiology systems or in conjunction with a vacuum manifold. As discussed below, there are a number of additional components that can be either part of the plate or as part of the washing device, as described below.

Surfaces/Solid Supports

In some embodiments, the solid supports include a planar surface. The planar surface has predefined hydrophobic or hydrophilic characteristics. In some embodiments, patterned areas are formed on the planar surface. The patterned areas have different hydrophobic or hydrophilic characteristics. In some embodiments, the planar surface has hydrophilic characteristics and the patterned areas have hydrophobic characteristics. In some embodiments, the planar surface has hydrophobic characteristics and the patterned areas have hydrophilic characteristics. In some embodiments, the patterned areas are formed by depositing a material having different hydrophobic/hydrophilic characteristics on the planar surface. For example, a polytetrafluoroethylene film may be formed on a glass substrate.

By "substrate" or "solid support" or other grammatical equivalents herein is meant any material that can be modified to contain the discrete individual sites appropriate for the creation of the drop arrays of the invention. Suitable substrates include metallic surfaces such as gold, glass and modified or functionalized glass, fiberglass, mica, plastic (including acrylics, polystyrene and copolymers of styrene and other materials, polypropylene, polyethylene, polybutylene, polyimide, polycarbonate, polyurethanes, cyclic olefin copoloymer, cyclic olefin polymer, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers. In some embodiments, the solid support is characterized by a flat or relatively flat surface, optionally with through holes that permit the flow of current or fluid under certain conditions, and/or selectively modified to achieve certain surface properties. For example, the solid support can be subjected, in some embodiments, to additional processing steps prior to use, e.g. chemical etching, plasma treatment, to selectively modify the surface properties thereof.

In some embodiments, the planar surface has a flatness of at most 300 µm. In some embodiments, the planar surface has a flatness of less than 50 µm. In some embodiments, the planar surface has a flatness of less than 10 µm over a 300 µm distance. The flatness can be important in embodiments where the planar surface is scanned or imaged. For example, when the planar surface is not flat, an image taken from either side of the planar surface may be distorted when the image is taken through the planar surface.

In some embodiments, the solid supports include an indented surface. For example, the solid supports may include protrusions or recesses. In some embodiments, the solid supports define shallow wells. In some embodiments, the wells may be formed by the fabrication process and/or the addition of layers to the supports. For 96-well plate, in some embodiments, the diameter is in the range of 1 mm-6 mm, preferably 2 mm-5 mm, with the well-to-well pitch of 9 mm. For 384-well plate, in some embodiments, the diameter will be in the range of 0.5 mm-3 mm, preferably 1 mm-2.5 mm, with well-to-well pitch of 4.5 mm. For 1536-well plate, in some embodiments, the diameter will be in the range of 0.3 mm-2 mm, preferably 0.5 mm-1.5 mm, with well-to-well pitch of 2.25 mm. For a slide of 75 mm×25 mm or 3"×1", the slide preferably follows the same well size and spacing as those of a conventional 96-well plate. The depth or protrusion height of the wells, in embodiments where there is a recess or protrusion, may be shorter than 2 mm, preferably less than 1 mm. In some embodiments, the recess is configured to hold a portion of a droplet. In such embodiments, the recess does not necessarily contain the entire volume of reagent within the recess, as is common with conventional microtiter plates. In some other embodiments, the recess is configured to contain the entire droplet.

Drop Arrays

FIG. 12 is perspective views of an exemplary array plate in accordance with some embodiments. In particular, FIG. 12 includes a top perspective view 110-A, a front perspective view 110-B, a left perspective view 110-C, a right perspective view 110-D, and oblique perspective views 110-E and 110-F of an exemplary array plate 110.

The exemplary array plate 110 includes at least a combination of a first structure (e.g., a plate) and a second structure (e.g., a frame). The details of the first structure and the second structure are described with respect to FIGS. 13A-13G below.

Figure 13A:
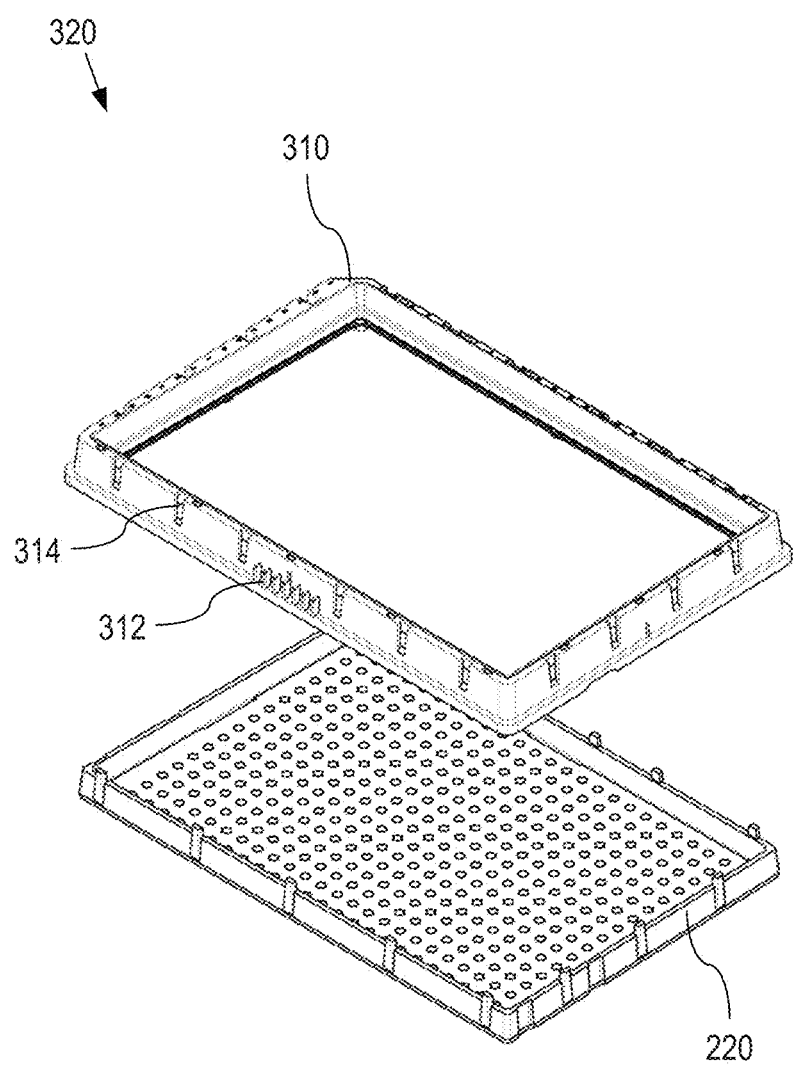
FIG. 13A is an exploded view of an exemplary array plate in accordance with some embodiments.

FIG. 13A is an exploded view of an exemplary combination of a first structure 202 and a second structure 204 in accordance with some embodiments. The first structure 202 includes a sheet layer that typically has a square or rectangular planar shape. Alternatively, in some embodiments, the sheet layer of the first structure 202 has a round shape, e.g. an ellipse, circle, or oval, with or without cutout(s). In some embodiments, the sheet layer has the same or similar dimensions as a microtiter plate when standard robotic mitrotiter handling devices are used. In other embodiments, the sheet layer has the same or similar dimensions to a microscope slide. Optionally, the first structure 202 may also include additional features, such as one or more vertical structures described below (e.g., the first structure 202 may be a tray including the sheet layer and one or more short sidewalls). In some embodiments, the sheet layer of the first structure 202 includes a sheet of a preselected material of a predefined thickness. The preselected material includes a polymer (e.g., polytetrafluoroethylene, any other perfluorocarbon polymer, or any other fluorocarbon polymer). The sheet layer has a thickness typically of 0.01-10 mm, 0.1-2 mm, 0.2-1 mm, or 1-2 mm.

In some embodiments, the first structure includes multiple layers. In some embodiments, the first structure includes at least one layer of a polymer material in addition to the sheet layer. In some embodiments, the first structure includes a glass layer in addition to the sheet layer. Typically, the one or more additional layers of the first structure are located below the sheet layer. In some embodiments, the one or more additional layers are made of an optically transparent material. Providing the one or more additional layers made of an optically transparent material allows scanning of the array plate through the one or more additional layers. For example, when the one or more additional layers are made of an optically transparent material, the array plate can be scanned from below the array plate. "Optically transparent" in this context means that the material will not interfere with the optical detection of the targets; for example, when fluorescence detection is used, "optically transparent" materials allow both detection of the fluorophores without significant interference. In some embodiments, a phase contrast microscopy or differential interference contrast microscopy (also known as Nomarski microscopy) is used. For example, some plastics have inherent fluorescent properties and should be avoided in these embodiments. Other embodiments may not require an optically transparent material; for example, in the case where the reactions are done on the array and then the sample is removed for detection or where the reading is done from the top (e.g. through the use of a "sipper" to add the sample to a capillary electrophoresis, FACS or mass spec detector), such materials are not necessary.

A plurality of discrete through holes 206 are defined in the sheet layer of the first structure 202. The plurality of discrete through holes 206 are formed by punching holes through the sheet layer of the first structure 202 (which typically includes a polymer). Typically, the plurality of discrete through holes have substantially the same diameter (e.g., with less than 50, 30, 20, 10, or 5% variation among the holes). In some embodiments, a respective through hole has a 1 mm-5 mm diameter, or 2 mm-3 mm diameter. In some embodiments, the discrete through holes are arranged in a predefined pattern. For example, when 96 discrete through holes are defined in the sheet layer of the first structure 202, the 96 discrete through holes are arranged in an 8×12 array. In some embodiments, the discrete through holes have a predefined spacing.

In some embodiments, pairs or other plurality of holes in the Teflon layer, e.g. within the space of a 96 or 384 pitch, are located adjacent to one another. Such configuration allows for the monitoring of cell or fluid migration between the different holes if the holes are close enough and the fluids can be mixed at a defined time, e.g. to create a chemoattractant gradient. For example, the attractant can be adhered to one of the wells such that it has a relatively slow off rate. In some embodiments, multiple reagents are pre-pipetted to the different wells. The multiple reagents can be mixed simply by making an addition such that the fluid touched the adjacent "well".

In some embodiments, the sheet layer of the first structure 202 includes at least 50% of fluorocarbon by weight. Alternatively, the sheet layer of the first structure 202 may include at least 60, 70, 80, 90, 95, or 99% of fluorocarbon by weight. In some embodiments, the sheet layer of the first structure 202 includes at least 90% of polytetrafluoroethylene by weight. Alternatively, the sheet layer of the first structure 202 may include at least 50, 60, 70, 80, 95, or 99% of polytetrafluoroethylene by weight. Alternatively, the sheet layer of the first structure 202 may include silicone polymer of silane, carbon and hydrogen, and hydrocarbon of carbon and hydrogen.

In some embodiments, the pattern of hydrophobicity and hydrophilicity is made by forming a hydrophilic coating on top of a hydrophobic substrate or by activating the selected areas of a hydrophobic substrate chemically or other methods such as plasma treatment. In some embodiments, a substrate includes a material of hydrophilicity, where a hydrophobic coating is formed on the surface of a hydrophilic substrate with a specific pattern. In some embodiments, the substrate is covered by a hydrophilic and hydrophobic coating. As a result, the substrate may not be directly involved in the surface interaction with biological molecules.

In some embodiments, a first surface (e.g., a surface facing away from the second structure 204) of the first structure 202 is roughened to increase the hydrophobicity and/or oleophobicity.

In some embodiments, at least the first surface of the first structure 202 is coated with a material of at least 50% of fluorocarbon by weight. The thickness of the coated material may be as thin as 1 nm, 2 nm, 5 nm, or 10 nm.

The second structure 204 includes a base layer 208 and one or more vertical structures 212 along, or adjacent to, a periphery of the base layer 208, adjacent a first surface of the base layer 208 (e.g., a top surface of the base layer 208 facing the first structure 202 as illustrated in FIG. 13A). In some embodiments, the base layer 208 defines an opening through which at least a portion of a second surface of the first structure (e.g., a bottom surface of the first structure) is exposed. As used herein, a vertical structure 212 refers to a structure protruding from a plane defined by the base layer 208. The vertical structure 212 typically defines a plane that is substantially perpendicular to the plane defined by the base layer 208 (e.g., the angle formed by the vertical structure 212 and the base layer 208 is 45° or less). In some embodiments, the one or more vertical structures 212 typically have at least 3 mm height. Alternatively, the one or more vertical structures 212 may have 1 mm, 2 mm, 4 mm, 5 mm, 6 mm, 8 mm, 10 mm, 12 mm, 14 mm, or 15 mm height. In some embodiments, the one or more vertical structures 212 have 0.1-5 mm width. Alternatively, the one or more vertical structures 212 may have 1-4 mm, 1-3 mm, 2-4 mm, 1-2 mm, or 2-3 mm width. In some embodiments, the one or more vertical structures 212 are configured to form a reservoir with the base layer 208. In other words, the reservoir is defined by the one or more vertical structures 212 and the base layer 208. In such embodiments, the reservoir formed by the one or more vertical structures of the second structure hold liquid without leaks. In some embodiments, the reservoir formed by the first structure and the second structure is configured to store at least a predefined volume of liquid (e.g., 1 ml, 5 ml, 10 ml, 20 ml, 50 ml, 100 ml, etc.).

In some embodiments, the base layer 208 of the second structure 204 includes a plurality of structures 210 that correspond to the plurality of discrete through holes in the first structure 202. In some embodiments, the second structure 204 is configured to mate with the first structure 202.

In some embodiments, the one or more vertical structures 212 include a plurality of pins 214. In some embodiments, the plurality of pins 214 vertically protrudes from the rest of the one or more vertical structures (e.g., a tip of a pin 214 is located further away from the rest of the one or more vertical structures). In some embodiments, the pins 214 provide additional stiffness for the one or more vertical structures 212. In some embodiments, the pins 214 also provide additional stiffness for the one or more side walls formed over the one or more vertical structures 212 so that the one or more side walls may maintain a flat top surface. In some embodiments, the pins 214 are used to remove an array plate from a mold, the process of which is described below with respect to FIG. 14J.

The second structure 204 typically includes a plastic material. In some embodiments, the plastic material includes polycarbonates. In some embodiments, the plastic material includes cyclic olefin polymer or copolymer. In some embodiments, the plastic material includes polystyrenes.

In some embodiments, the plastic material of the second structure 204 is optically transparent. This allows the second structure 204 to be optically imaged from a bottom surface side of the base layer 208 facing away from the first structure 202. In order to obtain high quality images, it is important to keep the first structure and the second structure.

Figure 13B:
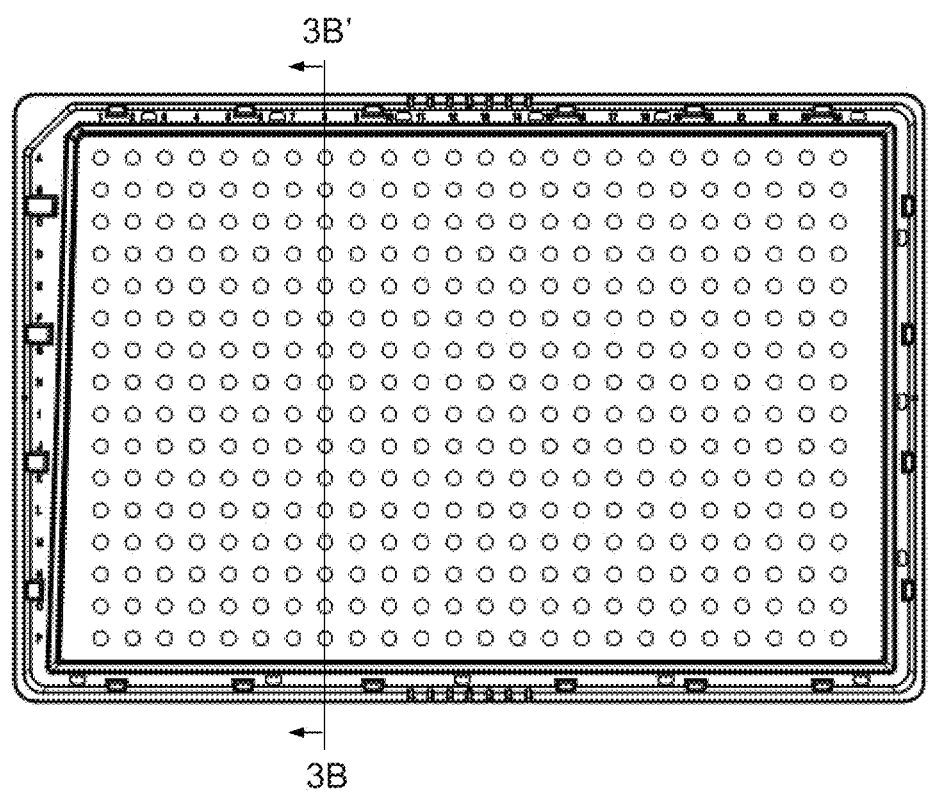
FIGS. 13B, 13D, and 13F are top perspective views of an exemplary array plate in accordance with some embodiments.

FIG. 13B is a perspective view of the exemplary combination 220 of the first structure 202 and the second structure 204 in accordance with some embodiments.

In some embodiments, the combination 220 of the first structure 202 and the second structure 204 is made by forming the second structure 204 through a molding process while the first structure is placed in a mold. The details of the molding process are described with respect to FIGS. 13E-13H below. Alternatively, the first structure 202 and the second structure 204 may be separately manufactured and subsequently attached together. However, forming the second structure through the molding process provides several advantages, including a better seal between the first structure and the second structure, the absence of glue or adhesives in forming the combination 220 of the first structure 202 and the second structure 204, and also a reduced number of manufacturing steps. The absence of glue or adhesives reduces the interference on biological experiments on the plate.

FIG. 13B also indicates a line 2B-2B' across the combination 220 of the first structure 202 and the second structure 204. The line 2B-2B' corresponds to the cross-sectional view illustrated in FIG. 13C.

Figure 13C:
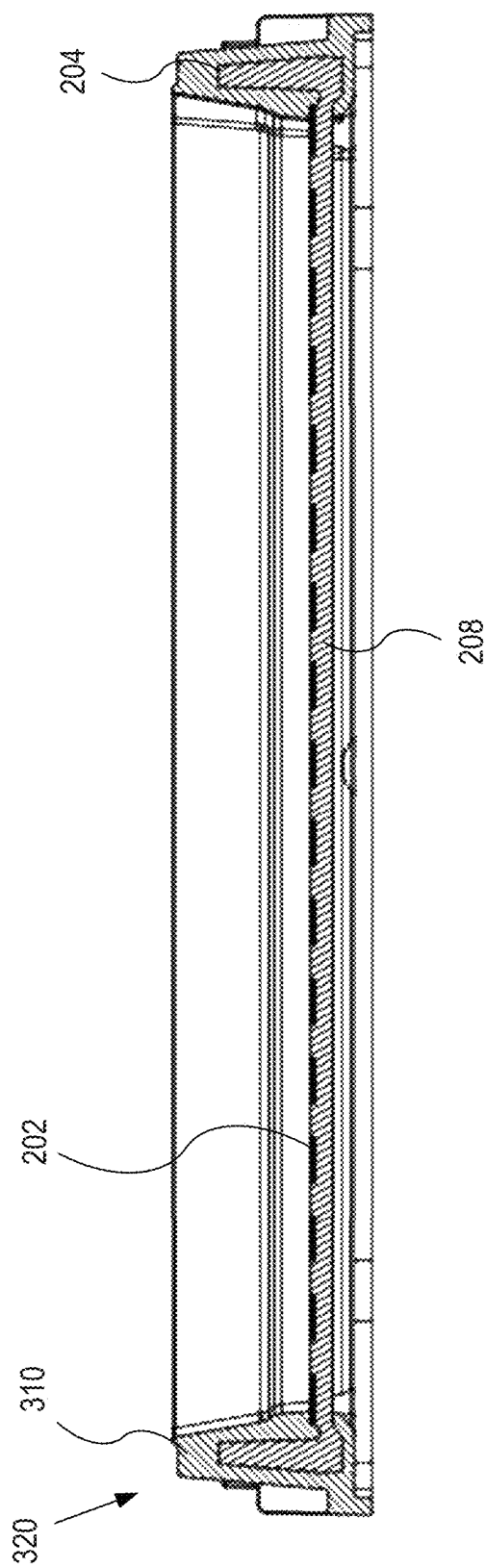
FIG. 13C is a cross-sectional view of the exemplary array plate corresponding to a section indicated in FIG. 13B in accordance with some embodiments.
Figures 1, 13C:
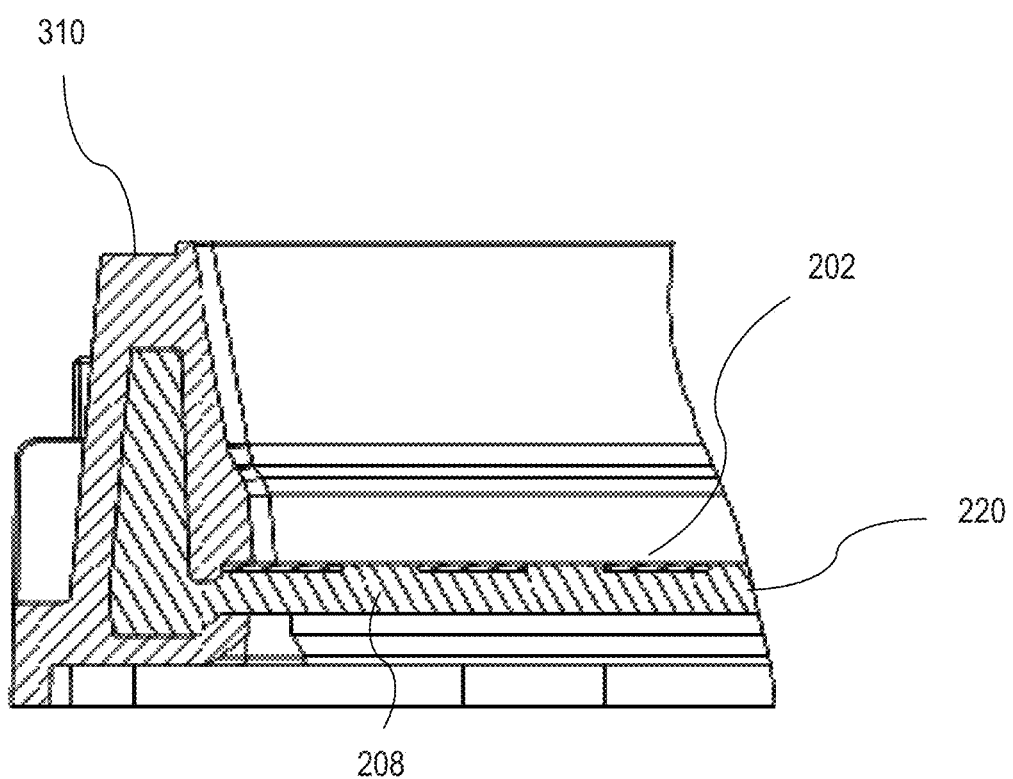

FIG. 13C is a cross-sectional view of the exemplary combination 220 of the first structure 202 and the second structure 204 in accordance with some embodiments. FIG. 13C also illustrates a pin 214 that vertically protrudes from the rest of the second structure 204 and a base layer 208.

Figure 13D:
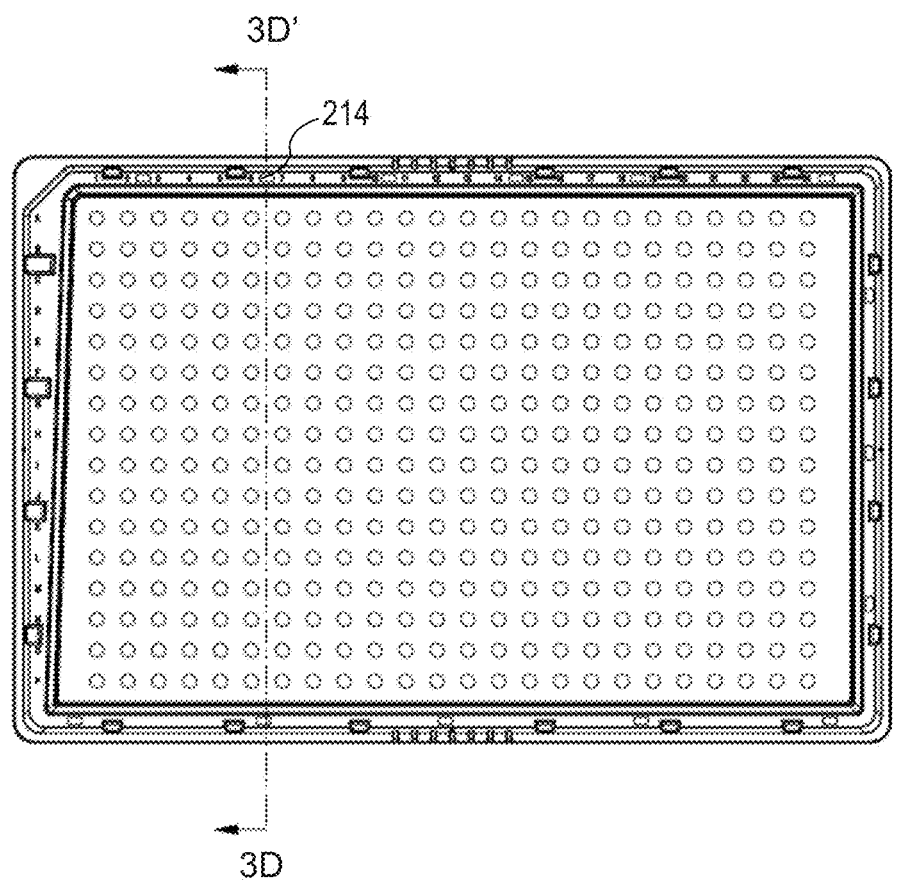

FIG. 13D is a partial sectional view of the exemplary combination 220 illustrated in FIG. 13C, near the junction of the base layer 208 and the one or more vertical structures 212, in accordance with some embodiments. When the second structure 204 is formed by a molding process, the base layer 208 and the one or more vertical structures 212 are integrally formed so that there is no hole or gap through which liquids leak.

As shown in FIG. 13D, in the combination 220 of the first structure 202 and the second structure 204, at least a portion of a first surface of the sheet layer of the first structure 202 (e.g., a top surface of the sheet layer of the first structure 202 facing away from the second structure 204) is exposed from the second structure 204, and a second surface of the sheet layer, opposite to the first surface of the sheet layer, (e.g., a bottom surface of the sheet layer of the first structure 202 facing the base layer 208 of the second structure 204) is embedded in the base layer 208 of the second structure 204 adjacent the first surface of the base layer 208. In other words, the top surface of the sheet layer of the first structure 202 is not entirely covered by the second structure 204. However, in some embodiments, a portion of the top surface of the sheet layer of the first structure 202 is covered by the second structure 204 along the periphery of the first structure. The bottom surface of the sheet layer of the first structure 202 is in contact with the base layer 208 of the second structure 204.

In some embodiments, the first structure 202 and the second structure 204 have different surface tensions. In some embodiments, structure 202 is configured to present a hydrophobic surface. Structure 204 is typically configured to present a surface that is compatible with an intended application or can be tailored to be compatible with an intended application. The materials of these two structures can have significantly different surface tensions. In some cases, these two structures exhibit weak or no adhesion at the contact. For example, when structure 202 is made of perfluorocarbon and when structure 204 is made of hydrocarbon, these two materials can show minimal adhesion at the contact. In such instances, the surface of the structure 202, which contacts the structure 204, may be treated to enhance the adhesion between these two contacting surfaces. In the example of structure 202 made of perfluorocarbon, the contacting surface of 202 is treated by chemical oxidation to create a less hydrophobic surface, leading to better adhesion with the structure 204. Also see description in paragraph [0074] above.

FIGS. 13E-13H are schematic diagrams illustrating selected steps for manufacturing an exemplary combination 220 of a first structure 202 and a second structure 204 in accordance with some embodiments. The elements in FIGS. 13E-13H are not drawn to scale.

Figure 13E:
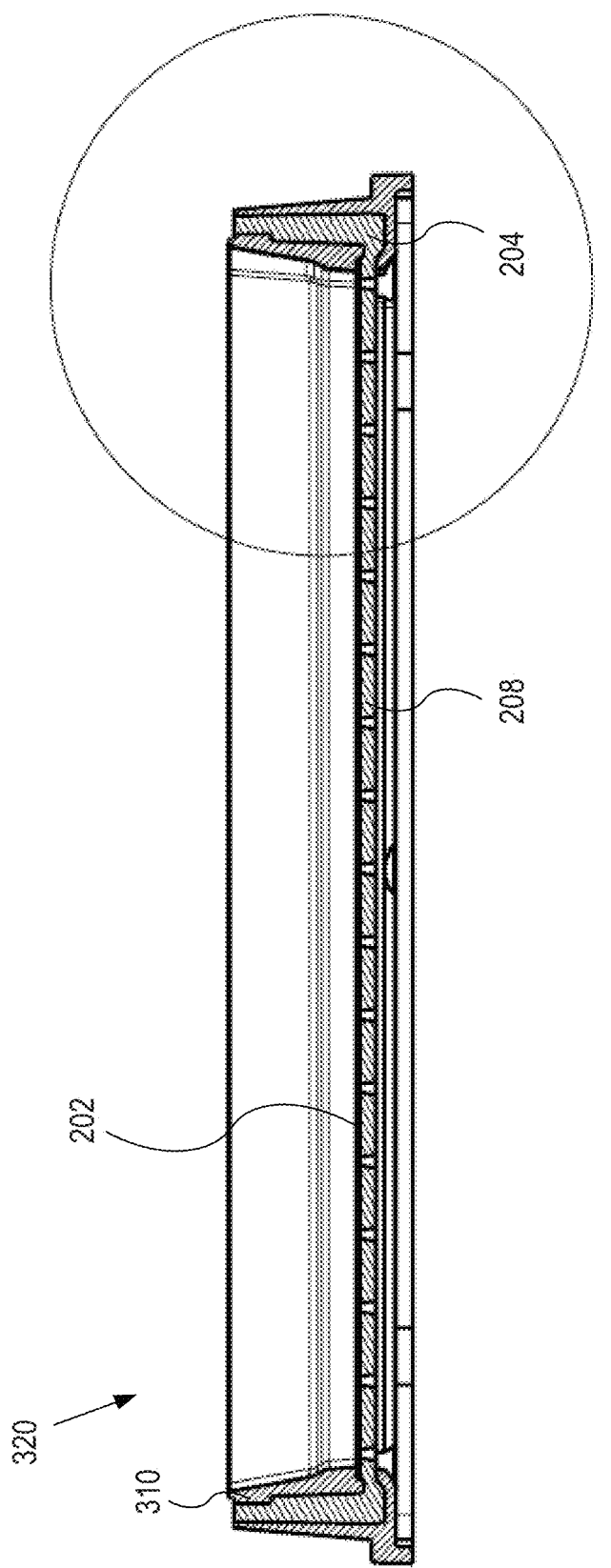
FIG. 13E is a cross-sectional view of the exemplary array plate corresponding to a section indicated in FIG. 13D in accordance with some embodiments.
Figures 1, 13E:
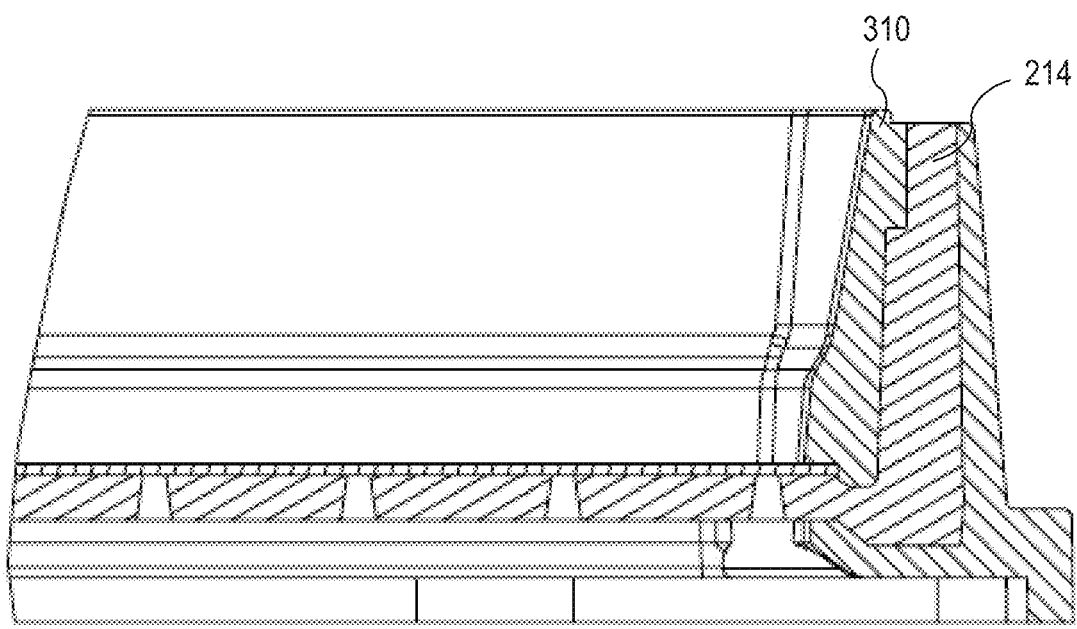

FIG. 13E illustrates that the first structure 202 is held in a first mold component 230 by vacuum suction. The vacuum suction pulls the first structure 202 toward the first mold component 230 so that the first structure 202 remains flat through the molding process. Typically, the vacuum suction is applied over a plurality of locations on the first structure 202. The vacuum suction typically leaves one or more indentations on the surface of the first structure 202 facing the first mold component 230. In some embodiments, the first mold component 230 includes a plurality of vacuum holes (not shown).

In some embodiments, a plurality of pins 242 coupled with the second mold component 240 are spring loaded so that the plurality of pins 242 are configured to apply force on the first structure 202 toward the first mold component 230 when the first mold component 230 and the second mold component 240 are assembled together.

In some embodiments, the bottom surface of the first structure 202 (e.g., the surface facing the second mold component 240) is treated, typically before the first structure 202 is held in the first mold component 230, to facilitate coupling with the second structure 204. In some embodiments, the bottom surface of the first structure 202 is treated to reduce the hydrophobicity (e.g., increase the surface tension) of the first structure 202. In some embodiments, the bottom surface of the first structure 202 is roughened to increate the contact area with the second structure 204.

In some embodiments, the first mold component 230 has a flat surface or a portion of the surface that is flat facing the first structure 202. In some embodiments, the surface of the first mold component 230 has protrusions and/or indentations, the impact of which is described below with respect to FIGS. 16A-16C below.

Figure 13F:
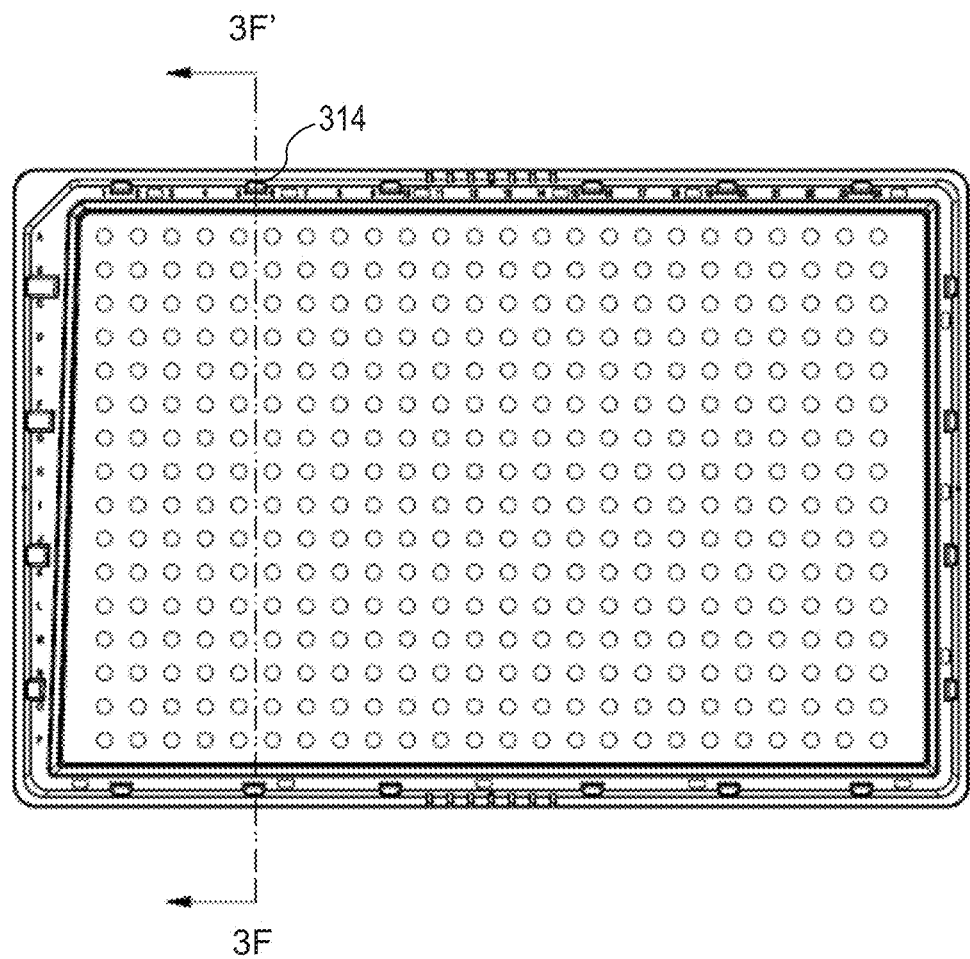

FIG. 13F illustrates that the first mold component 230 and the second mold component 240 are assembled, thereby forming a cavity inside, into which a heated plastic material is introduced for a molding process. In some embodiments, a surface of the mold component 230, which the structure 202 contacts, has a particular roughness. Preferably, the arithmetic average roughness is in the range of 0.1-1000 µm, preferably 100-1000 µm. The roughened surface of the contacting mold surface may induce roughness on the contacting surface of structure 202. The roughness on the contacting surface of structure 202 may be similar to or less than the roughness of the contacting mold surface. The roughness of the surface of the structure 202 may contribute to the increase of its hydrophobicity.

Figure 13G:
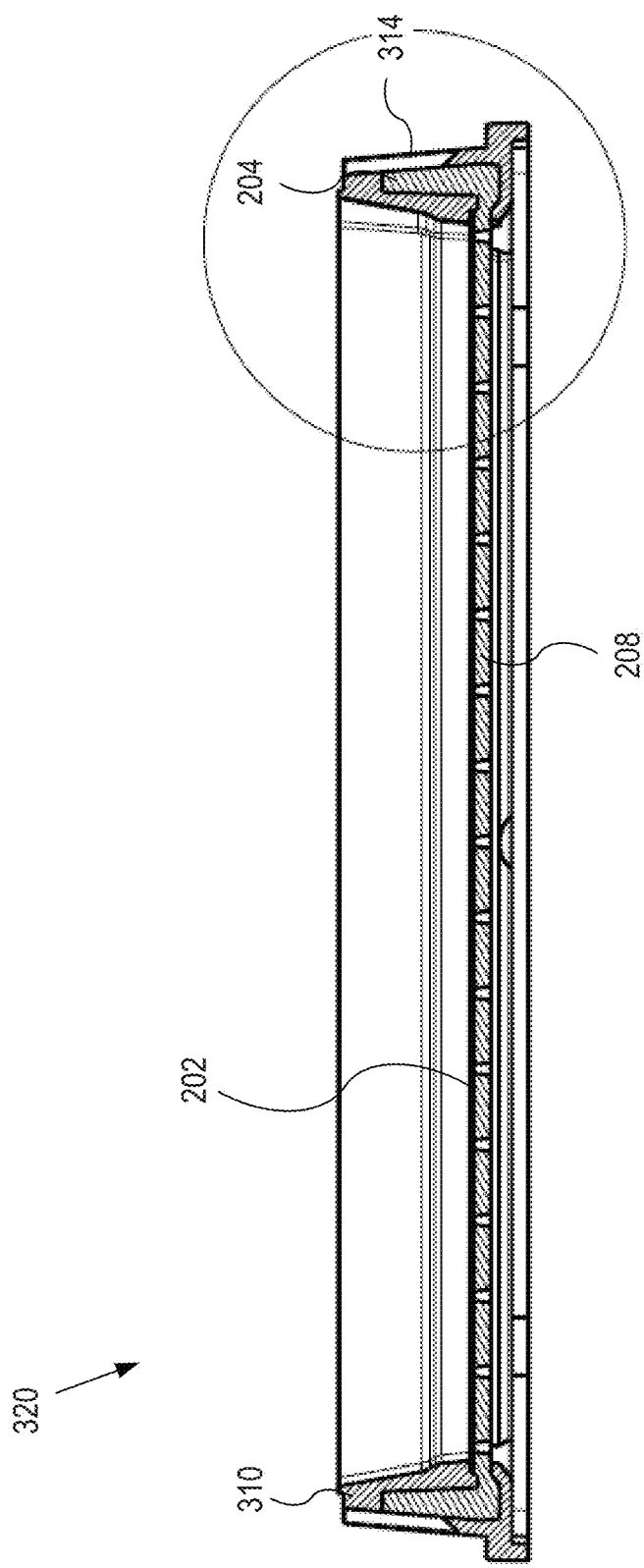
FIG. 13G is a cross-sectional view of the exemplary array plate corresponding to a section indicated in FIG. 13F in accordance with some embodiments.
Figures 1, 13G:
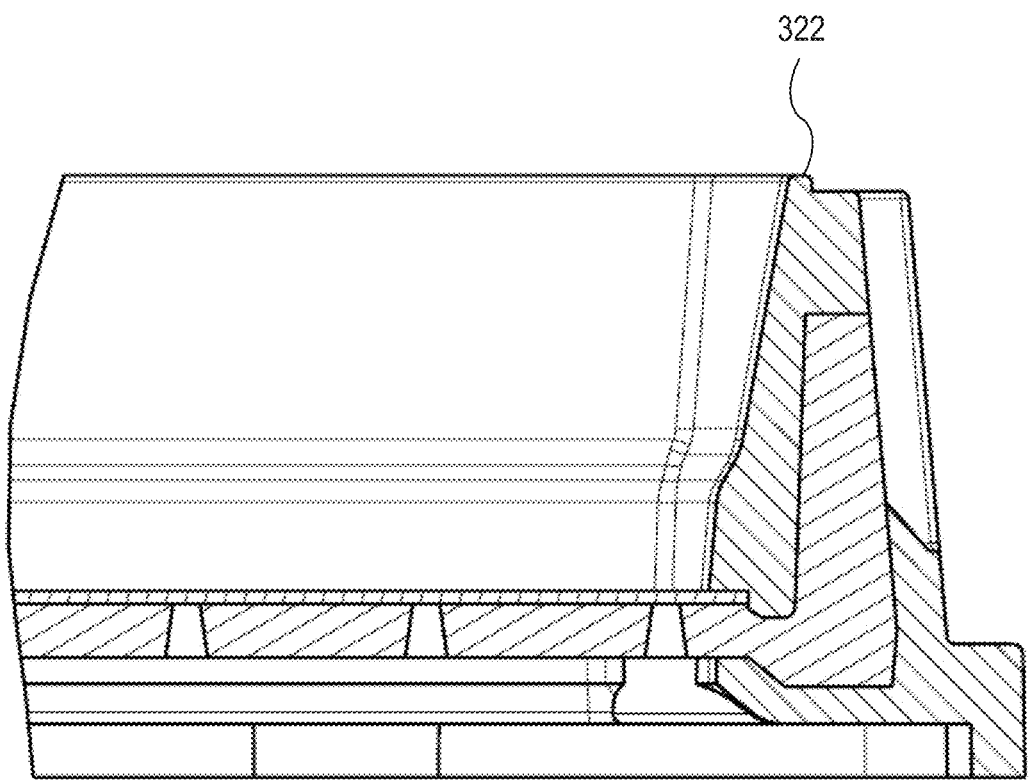

FIG. 13G illustrates that a heated plastic material is introduced into the cavity. In some embodiments, the plastic material includes polycarbonates. In some embodiments, the plastic material includes cyclic olefin polymer or copolymer.

Once the heated plastic material is cooled, the plastic material forms the second structure 204. When the second structure 204 is formed, the second structure 204 is coupled with the first structure 202 so as to form the combination 220 of the first structure 202 and the second structure 204.

Figure 13H:
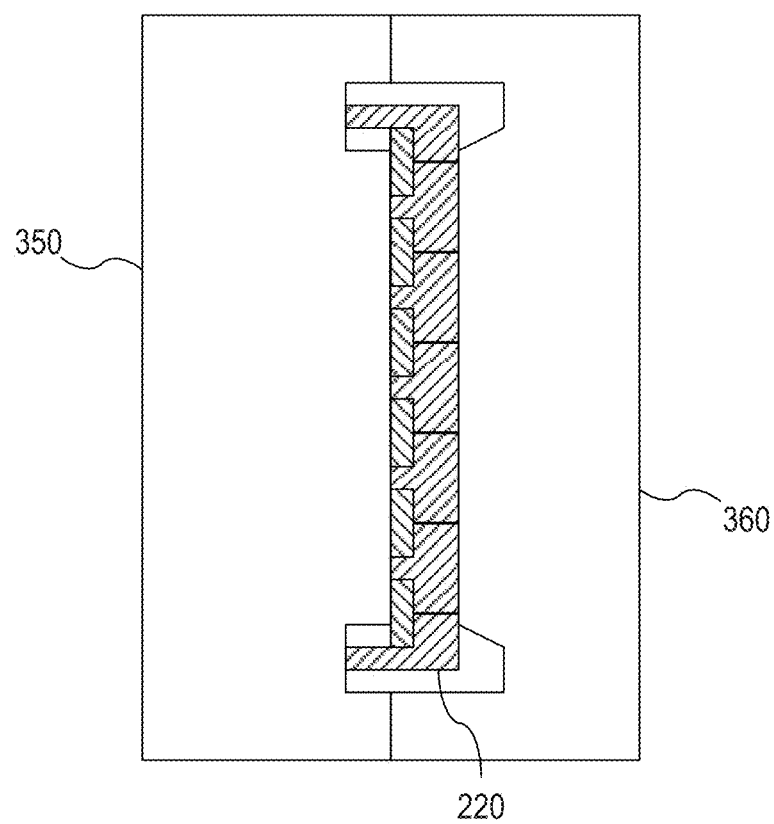
FIGS. 13H-13J are schematic diagrams illustrating selected steps for manufacturing an exemplary array plate in accordance with some embodiments.
Figure 13I:
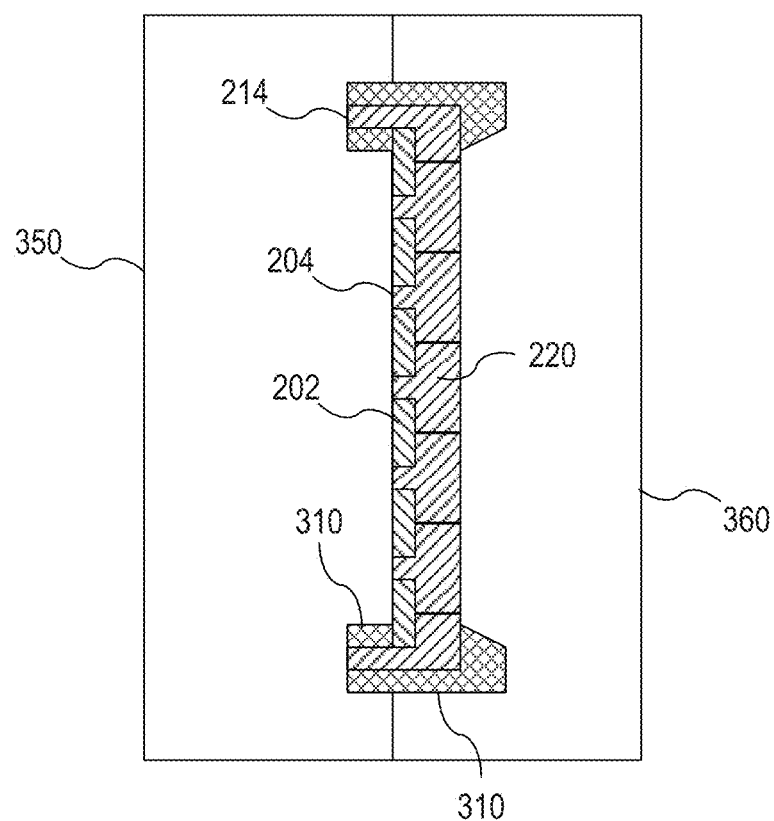
Figure 13J:
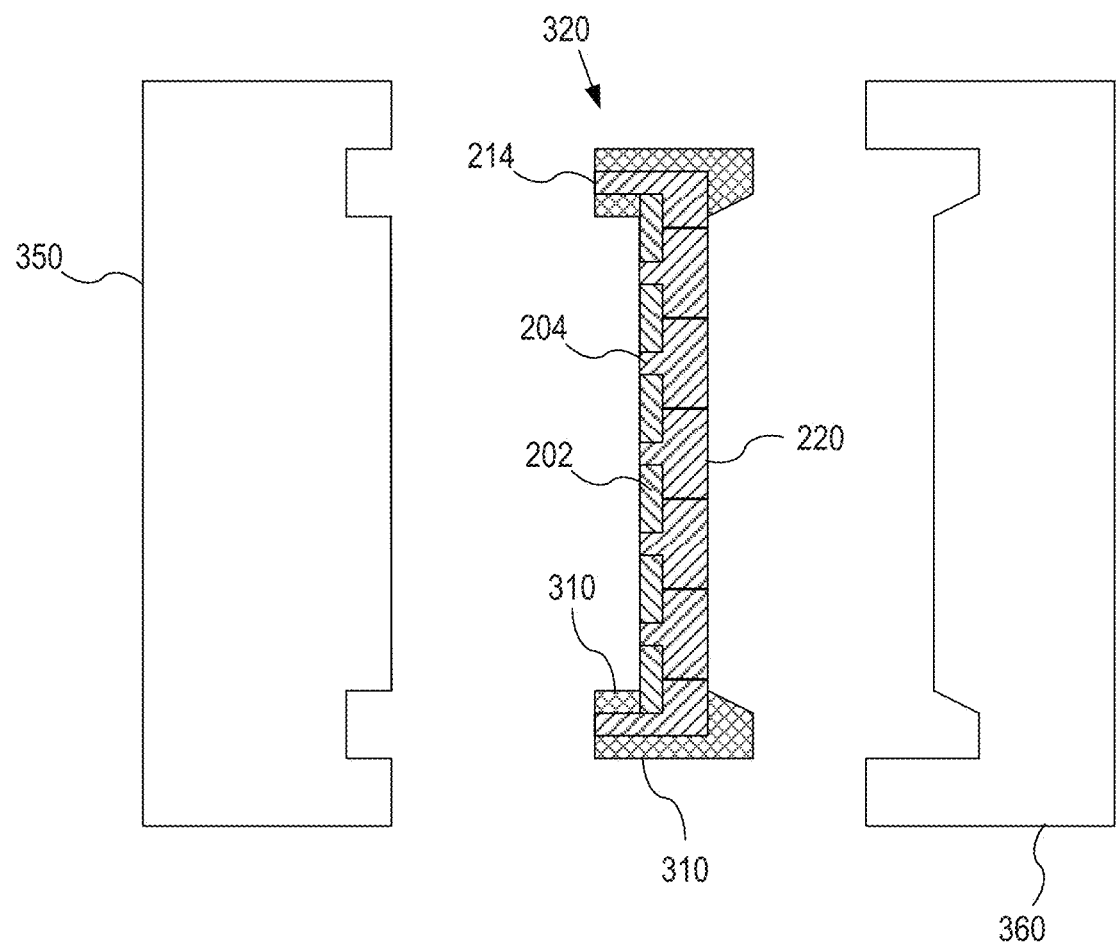

FIG. 13H illustrates that the combination 220 is removed from the first mold component 230 and the second mold component 240.

Note that the combination 220 removed from the first mold component 230 and the second mold component 240 has pin marks corresponding to the plurality of pins 242 coupled with the second mold component 240. When optical measurements (e.g., collection of optical images or optical signals) are performed through respective portions of the second structure 204 corresponding to the plurality of discrete through holes defined in the first structure 202, if the pin marks are located at the respective portions of the second structure 204 corresponding to the plurality of discrete through holes defined in the first structure 202, the pin marks interfere optical measurements. Thus, to avoid the interference by the pin marks, the plurality of pins 242 are located offset from the plurality of discrete through holes defined in the first structure 202. Alternatively, the first structure 202 and the second structure 204 are aligned so that the plurality of discrete through holes defined in the sheet layer of the first structure 202 is offset from the plurality of holding locations in the second structure 204.

Although FIGS. 13E-13H illustrate forming the combination 220 of the first structure 202 and the second structure 204 by a molding process, the combination 220 of the first structure 202 and the second structure 204 may be manufactured by attaching the first structure 202 to a preformed second structure 204.

Figure 14A:
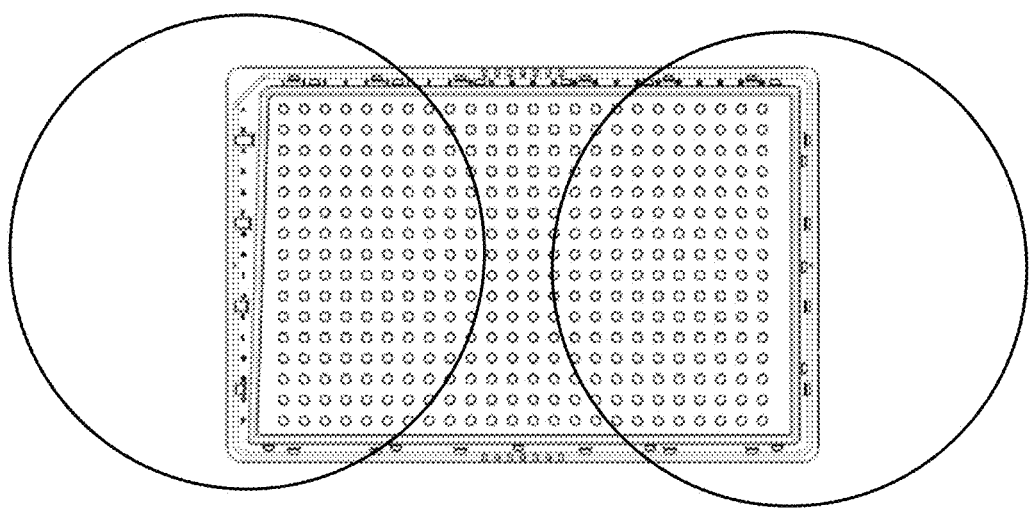
FIG. 14A is a top perspective view of an exemplary array plate in accordance with some embodiments.

FIG. 14A is an exploded view of an exemplary array plate 320 in accordance with some embodiments. The exemplary array plate 320 includes a third structure 310 and the combination 220 of the first structure 202 and the second structure 204 described above with respect to FIGS. 13E-13H.

In some embodiments, the third structure 310 includes a plurality of vertical indentations 314 along the outside of the third structure 310. In some embodiments, a respective side of the third structure 310 defines a longitudinal axis, and respective vertical indentations 314 located on the respective side of the third structure 310 are substantially perpendicular to the longitudinal axis formed by the respective side of the third structure 310 (e.g., a respective vertical indentation 314 forms 60-120° with the longitudinal axis of the respective portion of the third structure 310). In some embodiments, the vertical indentations 314 are substantially perpendicular to the plane defined by the base layer 208 of the second structure 202 of the combination 220 (e.g., a respective vertical indentation 314 forms 45° or less with a surface normal of the base layer 208 of the second structure 202 of the combination 220). In some embodiments, the plurality of vertical indentations 314 reduces distortion of the third structure 310, thereby maintaining a flatness of the top surface of the third structure 310.

In some embodiments, the third structure 310 includes one or more handles 312, each handle 312 including a plurality of fins.

Figure 14B:
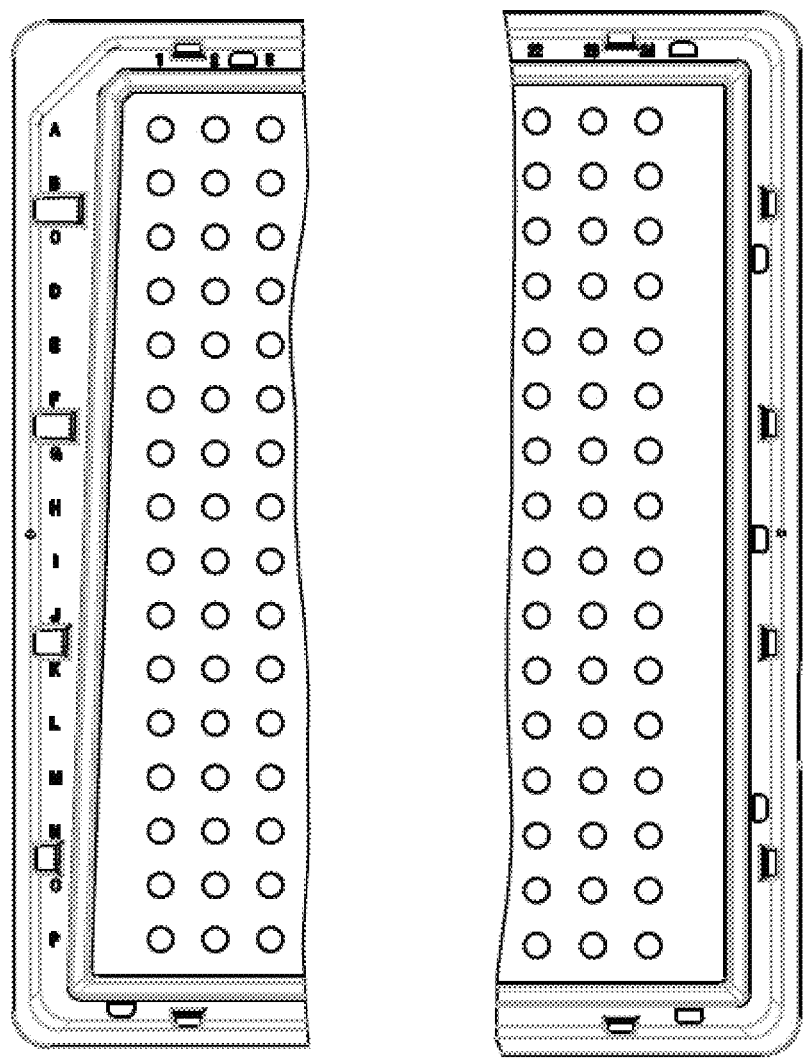
FIG. 14B is a partial top view of an exemplary array plate in accordance with some embodiments.

FIGS. 14B, 14D, and 14F are top perspective views of an exemplary array plate in accordance with some embodiments.

FIG. 14B also indicates a line 3B-3B' across the array plate 320. The line 3B-3B' traverses a plurality of the discrete through holes in the sheet layer of the first structure 202. The line 3B-3B' corresponds to the cross-sectional view illustrated in FIG. 14C.

FIG. 14C is a cross-sectional view of the exemplary array plate 320 corresponding to a section indicated in FIG. 14B in accordance with some embodiments. FIG. 14C-1 is a partial sectional view of a side wall region of the exemplary array plate 320 illustrated in FIG. 14C. FIGS. 14C and 14C-1 show that, in some embodiments, at least a portion of the first structure 202 is covered by the third structure 310 so that the first structure 202 is securely coupled, and any leak or retention of a liquid solution along the line between the first structure 202 and the third structure 310.

FIG. 14D also indicates a line 3D-3D' across the array plate 320. The line 3D-3D' corresponds to the cross-sectional view illustrated in FIG. 14E. The line 3D-3D' traverses the pins 214 in the vertical structures of the second structure 204. The line 3D-3D' corresponds to the cross-sectional view illustrated in FIG. 14E.

FIG. 14E is a cross-sectional view of the exemplary array plate 320 corresponding to a section indicated in FIG. 14D in accordance with some embodiments. FIG. 14E-1 is a partial sectional view of a side wall region (corresponding a circle illustrated in FIG. 14E) of the exemplary array plate 320 illustrated in FIG. 14E. As illustrated in FIG. 14E, in some embodiments, the pin 314 extends through the third structure 310 so that a top of the pin 314 is exposed.

FIG. 14F also indicates a line 3F-3F' across the array plate 320. The line 3F-3F' corresponds to the cross-sectional view illustrated in FIG. 14E. The line 3F-3F' traverses vertical indentations 314 on the side walls. The line 3F-3F' corresponds to the cross-sectional view illustrated in FIG. 14G.

FIG. 14G is a cross-sectional view of the exemplary array plate corresponding to a section indicated in FIG. 14F in accordance with some embodiments. FIG. 14G-1 is a partial sectional view of a side wall region (corresponding to a circle illustrated in FIG. 14G) of the exemplary array plate 320 illustrated in FIG. 14G. In some embodiments, the one or more side walls each have an inner surface, an outer surface, a bottom adjacent the sheet layer of the first structure 202, and a top surface opposite the bottom, and a respective side wall of the one or more side walls includes one or more lips 322 on the top surface, at least one of the one or more lips aligned with the inner surface of the respective side wall.

FIGS. 14H-14J are schematic diagrams illustrating selected steps for manufacturing an exemplary array plate with a second molding process in accordance with some embodiments. The elements in FIGS. 14H-14J are not drawn to scale.

FIG. 14H illustrates that the combination 220 of the first structure 202 and the second structure 204 is located in a cavity formed by a third mold component 350 and a fourth mold component 360.

FIG. 14I illustrates that the cavity formed by the third mold component 350 and the fourth mold component 360 is filled with a heated second plastic material. In some embodiments, the second plastic material is distinct from the plastic material used to form the second structure. In some embodiments, the second plastic material is identical to the plastic material used to form the second structure. In some embodiments, the second plastic material has a glass transition temperature lower than the glass transition temperature of the plastic material used for the second structure 204. This reduces the glass transition of the plastic material in the second structure 204 during the second molding process so that the second structure 204 maintains its shape and flatness during the second molding process. Exemplary glass transition temperatures are ~95° C. for polystyrene, ~130° C. for polyfluorotetraethylene, and 145-150° C. for polycarbonates. The glass transition temperature of cyclic olefin copolymer may exceed 150° C. In some embodiments, the melting temperature for the second plastic material is typically not higher than 200° C.

Once the second plastic material is cooled, the third structure 310 is formed. The third structure 310 is coupled with the combination 220 of the first structure 202 and the second structure 204. In some embodiments, the third structure 310 covers at least the one or more vertical structures of the second structure 204. In some embodiments, the third structure 310, when included, covers at least a portion of an inner surface of respective vertical structures 204, thereby forming one or more side walls. In other words, in such embodiments, the reservoir of the array plate 320 is defined by the third structure 310 on the sides, and the first structure 202 and the second structure 204 on the bottom. In some embodiments, a respective side wall of the one or more side walls has 1-8 mm, 2-5 mm, 2-4 mm, 2-3 mm, or 3-4 mm width. In some embodiments, a respective side wall of the one or more side walls has 1-10 mm, 2-9 mm, 3-8 mm, 4-7 mm, or 5-6 mm height.

In some embodiments, the one or more side walls each have an inner surface, an outer surface, a bottom adjacent the sheet layer of the first structure 202, and a top surface opposite the bottom, and a respective side wall of the one or more side walls includes one or more vertical indentations 314 (FIG. 14G) along the outer surface of the respective side wall.

In some embodiments, the one or more side walls are made of a hydrophobic material of a surface tension lower than 35 dynes/cm (e.g., hydrocarbon polymer, polypropylene, polytetrafluoroethylene, and their derivative, etc.). In some embodiments, the one or more side walls are made of a hydrophobic material of a surface tension lower than 25 dynes/cm. A surface having a low surface tension generally has a tendency to repel a solution. Thus, the surface of a low surface tension facilitates draining the solution from the plate.

In some embodiments, the one or more side walls each have an inner surface, an outer surface, a bottom adjacent the sheet layer of the first structure, and a top surface opposite the bottom, and the inner surface of a respective side wall of the one or more side walls is coated to expose a hydrophobic surface of a surface tension lower than 35 dynes/cm. The low surface tension of the inner wall facilitates draining the solution. As a result, the use of the inner wall with a low surface tension reduces the amount of a solution left after adding the solution and draining a bulk of the solution.

Array plates with the one or more side walls made with an elastic material may better handle thermal stress. Thus, in some embodiments, the hardness of the second plastic material is Shore A hardness of 85 or less. In some embodiments, the hardness of the second plastic material is Shore A hardness of 80 or less. In some embodiments, the hardness of the second plastic material is Shore A hardness of 75 or less. In some embodiments, the second plastic material has a tensile modulus of less than 2 GPa. The methods for measuring Shore A hardness and/or a tensile modulus are well known in the art, and are not repeated herein for brevity.

FIG. 14J illustrates that the array plate 320 is released from the third mold component 350 and the fourth mold component 360. In some embodiments, releasing the array plate 320 from the third mold component 350 includes pushing the plurality of pins 214 of the second structure 204. In some embodiments, the second structure 204 and the plurality of pins 214 of the second structure 204 are made of a stiffer material (e.g., a material with a higher elastic modulus, such as a spring constant, Young's modulus, etc.) than the third structure 310.

Although FIGS. 14H-14J illustrate forming the array plate 320 by a molding process, the array plate 320 may be manufactured by interposing the combination 220 of the first structure 202 and the second structure 204 between a top layer and a bottom layer, both of which are prefabricated, and attaching the top layer and the bottom layer to each other and/or to the combination 220 of the first structure 202 and the second structure 204.

Although FIGS. 13E-13H and FIGS. 14H-14J illustrate manufacturing an exemplary array plate using two-step molding processes, it is also possible to make an array plate with a single molding process.

In some embodiments, the one or more vertical structures formed during the first molding process may be configured to form one or more side walls, thereby eliminating the need for a second molding process to form one or more side walls over the one or more vertical structures.

Alternatively, in some embodiments, the first structure 202 includes one or more vertical structures (e.g., the first structure 202 includes a tray that has the sheet layer and one or more vertical structures, such as short walls, along the periphery of the sheet layer). In such embodiments, the molding step to form the vertical structures is skipped. In a molding step for forming one or more side walls, the first structure 202 is placed inside a mold, and a heated plastic is introduced to form one or more side walls over the one or more vertical structures of the first structure.

Figure 15A:
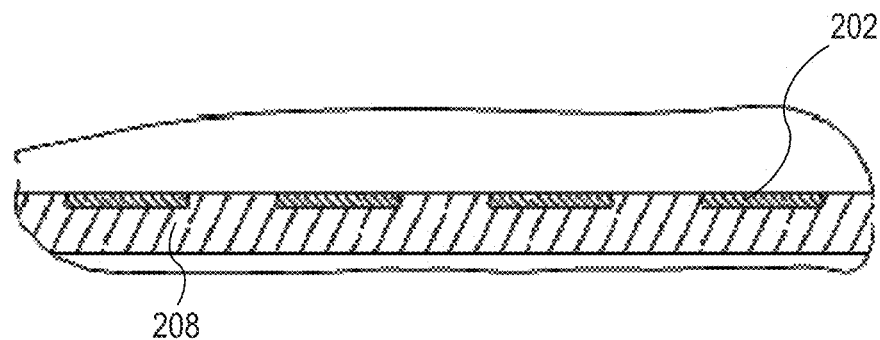
FIGS. 15A-15C are partial sectional views of exemplary array plates in accordance with various embodiments.
Figure 15B:
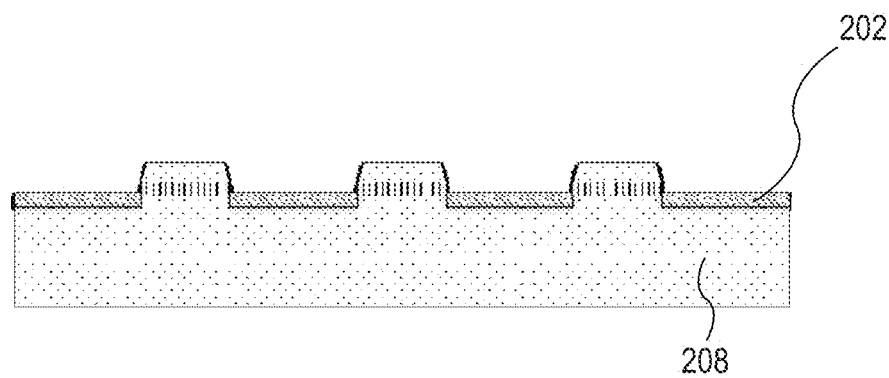

FIG. 15A is a top perspective view of an exemplary array plate in accordance with some embodiments. FIG. 15B are partial top views of an exemplary array plate, corresponding to regions indicated with circles in FIG. 15A, in accordance with some embodiments.

Figure 15C:
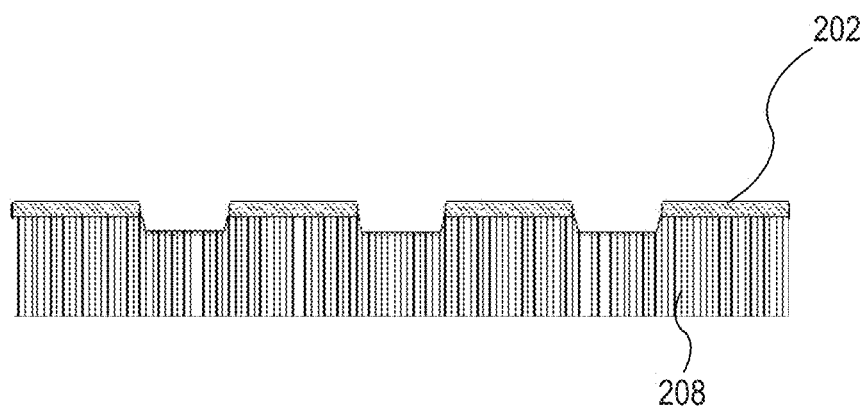

When the inner side walls and the base layer form sharp corners (e.g., the inner side walls and the base layer form 90 degree angle), the sharp corners hold more residual wash solution due to increased surface interaction, i.e. adhesion between the plastic surface and the solution. Therefore, in some embodiments, the contact lines between the inner side walls and the base layer of the second structure have a curved transition (e.g., rounded) as shown in FIG. 15. The rounded four corners of the circumferential wall reduce residual solution after a washing process.

FIGS. 15A-15B illustrate that, in some embodiments, at least one side wall is tilted outward an angle of 2-20 degrees so that the top of the side wall (e.g., the end of the side wall that is away from the base layer) is positioned outside the bottom of the side wall (e.g., the end of the side wall that is closer to the base layer). In some embodiments, all side walls are tilted by between 2-5 degrees.

Figure 16A:
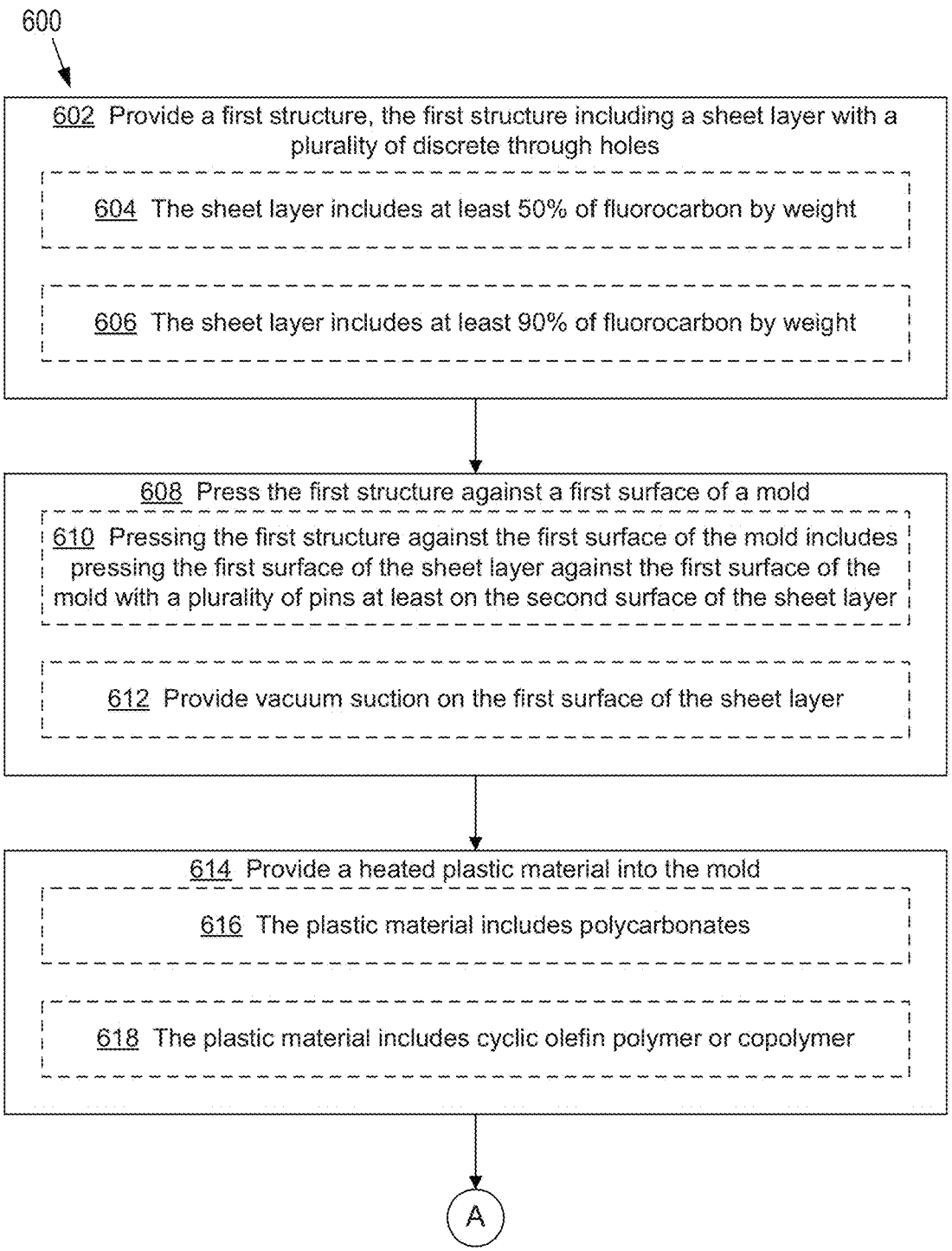

FIGS. 16A-16C are partial sectional views of exemplary array plates in accordance with various embodiments.

FIG. 16A illustrates that, in some embodiments, a top surface of the sheet layer of the first structure 202 is aligned with a top surface of the base layer 208 of the second structure 204. In some embodiments, the alignment of the top surface of the sheet layer of the first structure 202 and the top surface of the base layer 208 of the second structure 204 is achieved by using a mold component (e.g., the first mold component 230, FIG. 13E) that has a flat surface at least over a portion of the surface facing the top surface of the first structure 202. As shown in FIG. 13G, the heated plastic material fills up the plurality of discrete through holes defined in the first structure 202 up to the surface of the mold component 230 that faces the first structure 202, which is aligned with the top surface of the first structure 202.

In some embodiments, a mold surface that has indentations and/or protrusions is used. When the mold surface facing the top surface of the first structure 202 has indentations at locations corresponding to the plurality of discrete through holes defined in the first structure 202, the heated plastic material, when introduced into the cavity formed by mold components, fills the indentations. As a result, the top surface of the second structure is located above the top surface of the first structure as shown in FIG. 16B. Alternatively, when the mold surface facing the top surface of the first structure 202 has protrusions at locations corresponding to the plurality of discrete through holes defined in the first structure 202, the heated plastic material, when introduced into the cavity formed by mold components, underfills the discrete through holes defined in the first structure 202. As a result, the top surface of the second structure is located below the top surface of the first structure as shown in FIG. 16C. In some embodiments, the top surface of the second structure includes a plurality of concave surfaces. In some embodiments, a mold surface that has both indentations and protrusions is used. When the mold surface facing the top surface of the first structure 202 has indentations and protrusions at locations corresponding to the plurality of discrete through holes defined in the first structure 202, complex structures can be formed at the locations corresponding to the plurality of discrete through holes defined in the first structure 202.

FIGS. 17A-17D are flow charts representing a method 600 of making an array plate in accordance with some embodiments.

The method includes (602) providing a first structure. The first structure includes a sheet layer with a plurality of discrete through holes.

In some embodiments, the sheet layer includes (604) at least 50% of fluorocarbon by weight.

In some embodiments, the sheet layer includes (606) at least 90% of fluorocarbon by weight.

The method includes (608) pressing the first structure against a first surface of a mold.

In some embodiments, pressing the first structure against the first surface of the mold includes (610) pressing the first surface of the sheet layer against the first surface of the mold with a plurality of pins at least on the second surface of the sheet layer.

In some embodiments, the method includes (612) providing vacuum suction on the first surface of the sheet layer.

The method includes (614) providing a heated plastic material into the mold.

In some embodiments, the plastic material includes (616) polycarbonates.

In some embodiments, the plastic material includes (618) cyclic olefin polymer or copolymer.

In some embodiments, the plastic material includes polystyrene.

The method includes (620, FIG. 17B) cooling the plastic material to form a second structure so that the first structure and the second structure are coupled. The second structure includes a base layer and one or more vertical structures along a periphery of the base layer, adjacent a first surface of the base layer. At least a portion of a first surface of the sheet layer of the first structure is exposed from the second structure, and a second surface of the sheet layer, opposite to the first surface of the sheet layer, is embedded in the base layer of the second structure adjacent the first surface of the base layer.

In some embodiments, the plastic material of the second structure is (622) optically transparent, although as is discussed herein, some detection methods do not require optical tranparency.

In some embodiments, the method includes (624) coupling a third structure with at least the second structure over at least a portion of the one or more vertical structures, the third structure including one or more side walls.

In some embodiments, the one or more vertical structures of the second structure include (626) a plurality of pins vertically protruding from the rest of the one or more vertical structures.

In some embodiments, the method includes (628) molding the third structure over at least a portion of the one or more vertical structures with a second mold so as to couple the second structure and the third structure, and removing a combination of the second structure and the third structure from the second mold by pushing respective locations on the third structure that correspond to the plurality of pins of the second structure.

In some embodiments, the one or more side walls are (630) made of a plastic material that has a glass transition temperature lower than the glass transition temperature of (the material for) the second structure.

In some embodiments, the one or more vertical structures include (632) one or more side walls.

In some embodiments, the one or more side walls are (634, FIG. 17C) made of a material that has Shore A hardness of 85 or less.

In some embodiments, the one or more side walls each have (636) an inner surface, an outer surface, a bottom adjacent the sheet layer of the first structure, and a top surface opposite the bottom, and a respective side wall of the one or more side walls includes one or more lips on the top surface, at least one of the one or more lips aligned with the inner surface of the respective side wall.

In some embodiments, the one or more side walls each have (638) an inner surface, an outer surface, a bottom adjacent the sheet layer of the first structure, and a top surface opposite the bottom, and a respective side wall of the one or more side walls includes one or more vertical indentations along the outer surface of the respective side wall.

In some embodiments, the one or more side walls are (640) made of a hydrophobic material of a surface tension lower than 35 dynes/cm.

In some embodiments, the one or more side walls each have (642) an inner surface, an outer surface, a bottom adjacent the sheet layer of the first structure, and a top surface opposite the bottom, and the inner surface of a respective side wall of the one or more side walls is coated to expose a hydrophobic surface of a surface tension lower than 35 dynes/cm.

In some embodiments, the second structure includes (644) a plurality of holding locations, the method comprising aligning the first structure and the second structure so that the plurality of discrete through holes defined in the sheet layer of the first structure is offset from the plurality of holding locations in the second structure.

In some embodiments, the mold is configured (646, FIG. 17D) so that a top surface of the sheet layer of the first structure is aligned with a top surface of the base layer of the second structure.

In some embodiments, the mold is configured (648) so that a top surface of the sheet layer of the first structure is above a top surface of the base layer of the second structure.

In some embodiments, the mold is configured (650) so that a top surface of the sheet layer of the first structure is below a top surface of the base layer of the second structure.

In some embodiments, the first surface of the mold has (652) one or more of: a plurality of indentations and a plurality of protrusions corresponding to the plurality of discrete through holes defined in the sheet layer.

In some embodiments, at least one of the side walls includes (654) one or more handles, each handle comprising a plurality of parallel fins.

Many modifications and variations are possible in view of the above teachings. For example, in accordance with some embodiments, a method for making an array plate includes providing a first structure. The first structure including a sheet layer with a plurality of discrete through holes. The method includes pressing the first structure against a first surface of a mold, and providing a heated plastic material into the mold. The method includes cooling the plastic material to form a second structure so that the first structure and the second structure are coupled. The second structure includes a base layer and one or more side walls along a periphery of the base layer, adjacent a first surface of the base layer. At least a portion of a first surface of the sheet layer of the first structure is exposed from the third structure, and a second surface of the sheet layer, opposite to the first surface of the sheet layer, is embedded in the base layer of the second structure adjacent the first surface of the base layer.

In some embodiments, an array plate includes a first structure. The first structure including a sheet layer with a plurality of discrete through holes. The array plate also includes a second structure coupled to the first structure. The second structure including a base layer and one or more side walls along a periphery of the base layer, adjacent a first surface of the base layer. At least a portion of a first surface of the sheet layer of the first structure is exposed from the second structure, and a second surface of the sheet layer, opposite to the first surface of the sheet layer, is embedded in the base layer of the second structure adjacent the first surface of the base layer.

In accordance with some embodiments, a method for making an array plate includes providing a first structure. The first structure includes a sheet layer with a plurality of discrete through holes. The first structure also includes one or more vertical structures along a periphery of the sheet layer. The method includes pressing the first structure against a first surface of a mold, and providing a heated plastic material into the mold. The method includes cooling the plastic material to form a second structure so that the first structure and the second structure are coupled. The second structure includes a base layer and one or more side walls formed over the one or more vertical structures. At least a portion of a first surface of the sheet layer of the first structure is exposed from the third structure, and a second surface of the sheet layer, opposite to the first surface of the sheet layer, is embedded in the base layer of the second structure adjacent the first surface of the base layer.

In some embodiments, an array plate includes a first structure. The first structure including a sheet layer with a plurality of discrete through holes. The first structure also includes one or more vertical structures along a periphery of the sheet layer. The array plate also includes a second structure coupled to the first structure. The second structure including a base layer and one or more side walls formed over the one or more vertical structures. At least a portion of a first surface of the sheet layer of the first structure is exposed from the second structure, and a second surface of the sheet layer, opposite to the first surface of the sheet layer, is embedded in the base layer of the second structure adjacent the first surface of the base layer.

In some embodiments, the hydrophilic and hydrophobic pattern on a plate is created by forming a layer of hydrophilic material and/or hydrophobic material. In some embodiments, the hydrophilic and hydrophobic pattern on a plate is formed by selective surface treatment. For example, when an underlying substrate is relatively hydrophilic, a coating of a hydrophobic pattern can be formed by selective deposition of such a coating by plasma. It is well known that a hydrophobic film such as fluorinated carbon materials may be produced on a substrate, for example made of polymer, glass, metal or silicon. The method can be applied to the plate in order to produce a pattern of hydrophobic coating on the existing surface. Alternatively, when a substrate is relatively hydrophobic, a coating of a hydrophilic pattern may be produced similarly, for example by plasma deposition. Alternatively, when a substrate is relatively hydrophobic, selected surface areas of the hydrophobic substrate may be exposed to a condition such as chemical etching or plasma in order to produce a pattern of hydrophilic surface. When a method of treating a surface of the substrate with a chemical and/or plasma is employed, a plate can be made of a single material in a single molding process. Thereafter, the surface of the plate may be tailored by employing the coating and activation method by plasma, chemical etching, or deposition of a coating in order to produce appropriate surface properties at the right locations.

Operations and characteristics described above with respect to the method 600 are also applicable to these methods and apparatuses. For brevity, such operations and characteristics are not repeated herein.

Lids

In some embodiments, an array plate includes a lid. In some embodiments, the lid prevents or reduces evaporation of the one or more liquid droplets when the one or more liquid droplets are exposed to air. In some embodiments, the lid prevents or reduces contamination of the immiscible liquid and/or the one or more liquid droplets. In some embodiments, the lid is used to form an air-gap sealing. The lid forming an air-gap sealing may be used for aerobic cell culture, and in some cases anaerobic cell culture if needed.

In some embodiments, the lid extends over the side walls of the array plate. In some embodiments, the lid is configured to sit on the side walls of the array plate. The resulting lid/array plate combination does not necessarily have an air-tight seal.

In some embodiments, the lid or the array plate includes an elastomeric material to form an air-tight seal when the lid is placed over the array plate. In some embodiments, the lid or the array plate includes a gel to form an air-tight seal when the lid is placed over the array plate.

In some embodiments, the lid or the array plate has a lip to form a tighter seal. In some embodiments, both the lid and the array plate have mating indentations to form a tighter seal.

In some embodiments, the lid or the array plate has a clamper to form a tight seal when the lid is placed with the array plate. In some embodiments, the clamper includes a spring loaded mechanism to maintain the lid in place with the array plate. In some embodiments, the lid or the array plate has one or more magnets to form a tight seal when the lid is placed with the array plate.

Washing/Washing Devices

In use, the array plate includes one or more liquid droplets and an immiscible liquid on the base layer. At times, it is necessary to wash the array plate. In some embodiments, washing the array plate includes removing a substantial portion of the one or more liquid droplets. In some embodiments, washing the array plate includes replacing the substantial portion of the one or more liquid droplets with a different liquid. For example, a liquid droplet containing a reaction agent may be replaced with a buffer that does not include the reaction agent.

In some embodiments, a method of washing includes adding a wash buffer onto the array plate, and draining a substantial portion of the wash buffer from the array plate. In some embodiments, draining the substantial portion of the wash buffer includes tilting the array plate to a predefined angle (e.g., 30, 60, 90, 120, or 150 degrees or any other predefined angle). In some embodiments, draining the substantial portion of the wash buffer includes continuing to tilt the array plate to the predefined angle while the substantial portion of the wash buffer is drained from the array plate. It has been found that continuing to tilt the array plate while the substantial portion of the wash buffer is drained from the array plate retains a large amount of the wash buffer at hydrophilic regions of the plate. The largest wash buffer left on the plate may benefit mixing with the fresh incoming wash buffer at the next wash cycle. In general, however, the draining of the wash buffer at the last wash step of the given continuous wash is preferred to be performed at an angle more than 90 degree, say 120 degree from the horizontal position. Draining the wash buffer when a plate is tilted at 90 degree or higher angle has been found to leave the least amount of the wash buffer at hydrophilic pattern on the plate.

In some embodiments, a method of washing includes adding an additional amount of wash buffer into the assembly of the array plate and the cover (so-called clamper) before draining from the array plate. This is to ensure uniform amount of the wash buffer left on each hydrophilic feature. The addition of the additional wash buffer is particularly important at the last wash cycle of the continuous wash. It is because the plate is ready for the addition of reagent upon the completion of the wash. In a general wash process, a wash buffer is added into the space created by assembling the assay plate and the clamper. The amount of wash buffer may be best to fill the assembled space by 25-90%, preferably 50-80%. A space of air within the assembled space may be desirable to induce sufficient flow of the wash buffer during the shaking. In such case, the additional amount of wash buffer may be added into the assembly, so even when a plate is tilted to more than 90 degree, the entire array surface is still immersed under the wash buffer. Only when the wash buffer is drained, the array surface starts to get exposed. When the array plate remains at the same angle while the wash buffer is drained, the amount of the wash buffer left at hydrophilic features remains uniform throughout the plate. If a part of the array surface is exposed while the plate is tilted, the amount of the wash buffer left at the array exposed at the particular angle less than 90 degrees may be left with a volume bigger than the rest of the array. This may lead to dilution of the next reagent, which is typically undesirable.

In some embodiments, the method includes, prior to adding the wash buffer, draining a substantial portion of the immiscible liquid from the array plate. In some embodiments, draining the substantial portion of the immiscible includes tilting the array plate to a second predefined angle (e.g., 30, 60, 90, 120, or 150 degrees or other predefined angle). In some embodiments, draining the substantial portion of the immiscible liquid includes continuing to tile the array plate to the predefined angle while the substantial portion of the immiscible liquid is drained from the array plate. In some embodiments, the method includes exposing the plate to open air after draining the substantial portion of an immiscible liquid. This facilitates removing the immiscible liquid further.

In some embodiments, the method includes, after adding the wash buffer and prior to draining the substantial portion of the wash buffer, shaking the array plate. In some embodiments, shaking the array plate enables releasing molecules positioned near the base layer.

In some embodiments, the method includes, after draining the substantial portion of the wash buffer, adding an immiscible liquid onto the array plate.

In some embodiments, the method includes, after adding an immiscible liquid, shaking the array plate. For example, the array plate may be shaken briefly in order to spread the liquid uniformly over the entire surface of the plate.

In some embodiments, the wash buffer is selected from the group consisting of: phosphate buffered saline, phosphate buffered saline with Tween 20, and tris buffered saline. However, those of skill would recognize that other washer buffers are known in the art and may be selected and used in the present invention. Generally, for biological samples, washer buffers are aqueous solutions. For applications in chemistry or metallurgy, wash buffers may include hydrocarbon fluids. In some embodiments, the immiscible liquid is generally removed before disturbing any of the aqueous samples. In some embodiments, samples are washed by pipetting through the immiscible fluid and removing a portion of diluted liquid.

Timing Cycles

In some embodiments, the method includes resting the array plate for 1 sec-60 sec, preferably 5 sec-30 sec, between the addition of the wash buffer and shaking of the plate. The resting period may ensure the merging of the drops with the bulk wash buffer added, before the shaking starts.

Washing can be performed manually or in an automated device (e.g., a robotic device). In some embodiments, a device for washing the array plate (also called a washer) includes a plate holder for holding the array plate, wherein the plate holder is configured to hold and rotate the array plate at a plurality of angles.

In some embodiments, the washer includes a shaker coupled with the plate holder, wherein the shaker is configured to shake the array plate held in the plate holder. In some embodiments, the shaker is configured to shake the array plate at a frequency selected from the group consisting of 1-1000 rpm, 5-500 rpm, 10-100 rpm, 10-50 rpm, 15-40 rpm, and 18-40 rpm. In some embodiments, shaking the array plate includes rotating the array plate along a circular path having a radius selected from the group consisting of: 1-200 mm, 1-100 mm, 2-80 mm, 3-50 mm, 5-40 mm, and 10-35 mm. In some other embodiments, shaking the array plate includes moving the array plate along a linear path having a distance selected from the group consisting of: 1-200 mm, 1-100 mm, 2-80 mm, 3-50 mm, 5-40 mm, and 10-35 mm. Alternatively, shaking the array plate includes moving the array plate along a non-linear path (e.g., an orbital path).

In some embodiments, the method includes shaking the array plate. The shaking may last for 5 sec-60 sec, preferably 10-30 sec. The shaking may provide better mixing of the reagent from the drops and bulk wash buffer present in the assembly of the plate and clamper.

In some embodiments, the washer includes a cover placing mechanism for placing a cover over the array plate held in the plate holder. In some embodiments, the cover prevents spill of the one or more liquid droplets, the immiscible liquid, and/or the wash buffer from the array plate. In some embodiments, the cover mates with the lip on the array plate to form a tighter seal.

In some embodiments, the cover includes one or more holes for draining a substantial portion of the immiscible liquid.

In some embodiments, the plate holder is configured to receive the array plate at a first angle and rotate the array plate to a second angle for draining a substantial portion of the immiscible liquid, the second angle being distinct from the first angle. The first angle is, typically, substantially horizontal (e.g., 0 degree). However, the first angle may correspond to a non-horizontal orientation (e.g., 10 degrees, 15 degrees, 30 degrees, etc.). The second angle may be selected based on the type of the immiscible liquid. In some embodiments, the difference between the first angle and the second angle is selected from the group consisting of: 30 degrees, 60 degrees, 90 degrees, 120 degrees.

In some embodiments, the plate holder is configured to receive the array plate at a first angle and rotate the array plate to a third angle for providing a wash fluid into a cavity formed by the array plate and the cover. In some embodiments, the third angle is distinct from the first angle. In some embodiments, the plate holder is configured to keep the array plate at the first angle for providing the wash fluid. In some embodiments, the difference between the first angle and the third angle is selected from the group consisting of: 30 degrees, 60 degrees, 90 degrees, 120 degrees.

In some embodiments, the washer includes a wash fluid dispenser configured to provide a wash fluid into a cavity formed by the array plate and the cover.

In some embodiments, the plate holder is configured to receive the array plate at a first angle and rotate the array plate to a fourth angle for draining a substantial portion of the wash fluid, the fourth angle being distinct from the first angle. In some embodiments, the plate holder is configured to rotate the array plate to the fourth angle while draining the substantial portion of the wash fluid. As described above, it has been found that rotating the array plate to a drain angle (e.g., the fourth angle) while draining the substantial portion of the wash fluid removes a larger portion of the wash fluid. The fourth angle may be selected based on a type of the wash fluid. In some embodiments, the difference between the first angle and the fourth angle is selected from the group consisting of: 30 degrees, 60 degrees, 90 degrees, 120 degrees. In some embodiments, the stop and start of drainage is achieved by closing and opening an outlet, which controls the flow of the washing fluid. When this method is used, the tilt angle may be less critical and in some cases, the angle may not need to be changed during the washing.

In some embodiments, the washer includes an immiscible liquid dispenser configured to provide an immiscible liquid onto the array plate. In some embodiments, the immiscible liquid is recycled.

In some embodiments, the washer includes an array plate identifier component. In some embodiments, the array plate has an indentation for identification. In some embodiments, the washer includes a sensor and detects presence and orientation of the array plate based on a physical contact between the sensor and the array plate.

In some embodiments, the washer includes a plate scanner. In some embodiments, the plate scanner includes an optical scanner.

In some embodiments, the washer includes an incubator.

In some embodiments, the washer includes one or more magnets in or adjacent to the plate holder. In some embodiments, the one or more magnets are positioned under the array plate when the array plate is received in the plate holder. When the one or more liquid droplets include magnetic beads, the one or more magnets hold the magnetic beads. The use of the one or more magnets typically reduces a loss of the magnetic beads during washing. In some embodiments, the one or more magnets are used to align/position the plate. In some embodiments, the one or more magnets are configured to move toward or away from the plate. Moving the one or more magnets away from the plate facilitates resuspension of the magnetic beads. In some embodiments of the invention, resuspension of the magnetic beads is performed between washes.

Mixing/Agitation

In some embodiments, providing a respective reagent to a respective liquid droplet initiates mixing of the respective reagent with the respective liquid droplet. In some embodiments, agitating (e.g., shaking) the array plate increases a speed of mixing the respective reagent with the respective liquid droplet.

In some embodiments, agitating the array plate is done by an automated device (called a mixer). In some embodiments, the mixer includes a plate holder for holding the array plate, and a reagent dispenser coupled to provide one or more reagents to one or more liquid droplets of the array of liquid droplets on the array plate.

In some embodiments, the mixer includes a shaker coupled with the plate holder for shaking the array plate. In some embodiments, shaking the array plate releases suspension cells positioned adjacent to the base layer.

In some embodiments, the shaker is configured to shake the array plate at a rotational speed selected from the group consisting of: 1-10,000 rpm, 10-5000 rpm, 100-3000 rpm, 500-2000 rpm, 750-1500 rpm, and 800-1200 rpm.

In some embodiments, shaking the array plate includes rotating the array plate along a circular path having a radius selected from the group consisting of: 1-200 mm, 1-100 mm, 2-80 mm, 3-50 mm, 5-40 mm, and 10-35 mm.

In some embodiments, the mixer is integrated with the washer described above.

Dispenser

In some embodiments, the washer includes a dispenser. The dispenser is integrated to deliver solutions/reagents as needed onto the specific spot on the array plate. The typical volume of the dispenser is adjusted to accommodate the volume required for each type of the array plate. The range of the dispensing volume may be 0.1 ul-100 ml, preferably 0.3 ul-50 ml.

Sterilization

In some embodiments, the washer may undergo priming of the fluidic channels and/or a typical wash cycle with a sterilization solution such as 70% EtOH in water or a hypochlorite solution. Once the washer is exposed to the sterilization solution, it is extensively flushed with DI water and/or a biological buffer such as phosphate saline buffered solution in order to minimize the presence of the sterilization solution.

Immiscible Liquids

In some embodiments, the array plate includes an immiscible liquid that coats the plate with a thin layer. As used herein, immiscible liquid means a fluid that is immiscible with a liquid droplet (e.g., hydrophilic liquid, such as water or a tissue culture media, or hydrocarbon-based liquids). Non-limiting examples of immiscible liquid useful in the present invention include the perfluorinated hydrocarbon liquid sold under the trademark Fluorinert™ name by the 3M Corporation (St. Paul, Minn., USA) and the immiscible fluid sold by Curiox Biosystems (Singapore), e.g. under the trademarks Rinsing Oil™, Incubation Oil™, or Sealing Fluid™. Some immiscible liquids, such as perfluorinated hydrocarbon liquid, are hydrophobic and oleophobic, which repels not only aqueous solutions but also hydrocarbon solutions. The presence of hydrophobic immiscible liquid reduces the possibility of the leakage between neighboring wells in the presence of a hydrophilic liquid (e.g., a liquid bearing a reagent). The hydrophobic immiscible liquid thus makes a hydrophobic surface of a solid substrate such as polypropylene and polytetrafluoroethylene more resistant against wetting by a hydrophilic liquid.

In some embodiments, the immiscible liquid has substantially the same (e.g., the difference is not more than 25%) surface energy as the hydrophobic area of the array plate (e.g., base layer and/or circumferential wall). In some embodiments, the immiscible liquid has a lower surface energy than the hydrophobic area of the array plate.

Once made, the plates and washing apparatus of the present invention find use in a variety of applications, including biochemical assays.

III. Applications and Assays

The present invention finds use in the processing of a variety of samples for various applications.

Samples and Sample Preparation

Accordingly, in one aspect the present invention provides compositions and methods for detecting the presence or absence of target sequences in samples. As will be appreciated by those in the art, the sample solution may comprise any number of things, including, but not limited to, bodily fluids (including, but not limited to, blood, urine, serum, lymph, saliva, cerebrospinal fluid, synovial fluid, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., J Cell Physiol. (2007) 210(2):279-89; Osada et al., Carcinogenesis. (2007) 28(1):2-12; and Mattes et al., Am J Respir Cell Mol. Biol. (2007) 36(1):8-12, each of which is incorporated herein by reference in its entirety).

As will also be appreciated by those in the art, the samples can be prepared in a variety of ways, depending on the sample and the desired assay, as is generally outlined below. For example, to assay intracellular proteins, the cell sample may require lysis.

The present invention is directed in some embodiments to the detection of targets in samples. By "target analyte" or "analyte" or grammatical equivalents herein is meant any molecule or compound to be detected and that can bind to a binding species, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), peptides, cell fragments, metabolites, ions or other small molecules, nucleic acids, lipids, lectins, carbohydrates, hormones, whole cells (including prokaryotic (such as pathogenic bacteria) and eukaryotic cells, including mammalian tumor cells), viruses, spores, etc. Particularly preferred analytes are proteins including enzymes; drugs; cells; antibodies; antigens; cellular membrane antigens and receptors (neural, hormonal, nutrient, and cell surface receptors) or their ligands.

In some embodiments, the term "sample" as used herein refers to a biological sample obtained for the purpose of evaluation in vitro or ex vivo.

Cell-Based Assays

Those of skill in the art will appreciate that the array plates and devices described herein can be used in both homogeneous and heterogeneous cell-based assays. Cell-based assays, which are fundamental for understanding the behavior of and biochemical events in cells, have been used with increasing frequency in biology, pharmacology, toxicology, genetics, and oncology (see, e.g., Benjamin et al. (1992) Mol. Cell. Biol. 12:2730-2738). Such cell lines may be constructed or purchased (see, e.g., the Pro-Tox Kit available from Xenometrix, Boulder Colo.; see, also International PCT Application No. WO 94/7208 cell lines). Established cell lines, primary cell culture, stem cells (e.g. embryonic, fetal, iPS cells), co-cultures of cells, mixed cell cultures, reporter gene systems in recombinant cells, cells transfected with gene of interest, and recombinant mammalian cell lines have been used to set up cell-based assays. For example, Xenometrix, Inc. (Boulder, Colo.) provides kits for screening compounds for toxicological endpoints and metabolic profiles using bacteria and human cell lines; screening is effected by assessing activation of regulatory elements of stress genes fused to reporter genes in bacteria, human liver or colon cell lines and provide information on the cytotoxicity and permeability of test compounds.

In any drug discovery program, cell-based assays offer a broad range of potential targets as well as information on cytotoxicity and permeability. The ability to test large numbers of compounds quickly and efficiently provides a competitive advantage in pharmaceutical lead identification.

High throughput screening with cell-based assays is often limited by the need to use separation, wash, and disruptive processes that can compromise the functional integrity of the cells and performance of the assay or result in cell loss, especially when semi-adherent cells or suspension cells are involved. In contrast, the unique fluid dynamic by which contents of each assay are held in the hydrocarbon droplet that defines each virtual well of the array plate precludes the need for a centrifugation step commonly employed in the art. In this manner, one can minimize the instance of cell loss, human error, machine error, and thereby enhance reproducibility and quality of results.

In some embodiments, the invention provides a method of culturing cells involving: a) providing a flat surface comprising a hydrophobic surface with an array of hydrophilic immobilization areas, a plurality of said areas comprising cells immobilized on said areas and a cell culture medium, wherein said surface is covered by an immiscible medium; and b) incubating said surface at a temperature suitable for cell culture. Standard cell culture conditions can be employed, e.g., sterile environment at 37° C. in an incubator containing a humidified 95% air/5% $CO_2$ atmosphere. The appropriate cell culture media can be selected according to the cell type and assay by those of skill in the art. Examples include media containing undefined biological fluids such as fetal calf serum, or media which is fully defined and serum-free. For example, MCDB 153 is a selective medium for the culture of human keratinocytes (Tsao et al. (1982) J. Cell. Physiol. 110:219-2291.

In some embodiments, the invention provides a method of running assays at multiple temperatures, e.g. PCR reactions, using the array plates described herein. For example, an array plate with a lid can be placed in a thermocycler, whereby the plate with reagents is then exposed to different temperatures respectively for the desired duration for running assays.

The array plates of the invention are also suitable for use with any adherent, partially adherent cell type, or even suspension cell type that can be cultured on standard micro titer plates, including culture of primary cells, normal and transformed cells derived from recognized sources species and tissue sources. In addition, cells that have been transfected with the recombinant genes may also be cultured using the invention. There are established protocols available for the culture of many of these diverse cell types (see, e.g., Freshney et al. (1987) Culture of Animal Cells: A Manual of Basic Technique. 2nd Edition, Alan R. Liss Inc.). These protocols may require the use of specialized coatings and selective media to enable cell growth and the expression of specialized cellular functions.

The array plate of the present invention, as with conventional microtiter plates, may require surface modification in order to be adapted for the attachment and/or growth of cells in select cell-based assays. Treatment can involve the use of high voltage plasma discharge, a well-established method for creating a negatively charged plastic surface (see, e.g., Amstein et al. (1975) Clinical Microbiol. 2:46-54). Cell attachment, growth and the expression of specialized functions can be further improved by applying a range of additional coatings to the culture surface of the array plate. These can include: (i) positively or negatively charged chemical coatings such as poly-lysine or other biopolymers (McKeehan et al. (1976) J. Cell Biol. 21:727-734 (1976)); (ii) components of the extracellular matrix including collagen, laminin, fibronectin (see, e.g., Kleinman et al. (1987) Anal. Biochem. 166: 1-13); and (iii) naturally secreted extracellular matrix laid down by cells cultured on the plastic surface (Freshney et al. (1987) Culture of Animal Cells: A Manual of Basic Technique, 2nd Edition, Alan R. Liss Inc.). Furthermore, the array plate plate may be coated with agents, such as lectins, or adhesion molecules for attachment of cell membranes or cell types that normally grow in suspension. Methods for the coating of plasticware with such agents are known (see, e.g., Boldt et al. (1979) J. Immunol. 123:808).

In addition, the surface of the array plate may be coated with living or dead cells, cellular material, or other coatings of biological relevance. The interaction of radiolabeled living cells, or other structures with this layer can be monitored with time allowing processes such as binding, movement to or from or through the layer to be measured.

Virtually all types of biological molecules can be studied. Any molecule or complex of molecules that interact with the cell surface- or that can be taken up, transported and metabolized by the cells, can be examined using real time analysis. Examples of biomolecules will include receptor ligands, protein and lipid metabolite precursors (e.g., amino acids, fatty acids), nucleosides and any molecule that can be radiolabeled. This would also include ions such as calcium, potassium, sodium and chloride, that are functionally important in cellular homeostasis, and which exist as radioactive isotopes or which could be measured by some type of spectroscopy, e.g. atomic absorption spectroscopy. Furthermore, viruses and bacteria and other cell types, which can be radiolabeled as intact moieties, can be examined for their interaction with monolayer adherent cells grown in the array plate virtual well format.

Where radiolabeling is employed for detection, the type of radioactive isotope that can be used with this system will typically include any of the group of isotopes that emit electrons having a mean range up to 2000 µm in aqueous medium. These will include isotopes commonly used in biochemistry such as ($^{3}H$), ($^{125}I$), ($^{14}C$), ($^{35}S$), ($^{45}Ca$), ($^{33}P$), and ($^{32}P$), but does not preclude the use of other isotopes, such as ($^{55}Fe$), ($^{109}Cd$) and ($^{51}Cr$) that also emit electrons within this range. The wide utility of the invention for isotopes of different emission energy is due to the fact that the current formats envisaged would allow changes to the thickness of the layer containing a scintillant substance, thereby ensuring that all the electron energy is absorbed by the scintillant substance. Furthermore, cross-talk correction software is available which can be utilized with all high energy emitters. Applications using these plates include protein synthesis, $Ca^{2+}$ transport, receptor-ligand binding, cell adhesion, sugar transport and metabolism, hormonal stimulation, growth factor regulation and stimulation of motility, thymidine transport, and protein synthesis.

In some embodiments of the invention, cells are cultured on an array plate to which test compounds and/or reagents have been immobilized. The reagents includes cDNAs or RNAs, which may be immobilized for transfection. Cytostatic, cytotoxic and proliferative effects of the test compounds will be measured using colorimetric (MTT, XTT, MTS, Alamar blue, and Sulforhodamine B), fluorimetric (carboxyfluorescein diacetate), chemiluminescent reagents (e.g., CytoLite™, Packard Instruments, which is used in a homogeneous luminescent assay for cell proliferation, cell toxicity and multi-drug resistance), impedance detection (e.g., xCELLigence by Roche and ACEA Biosciences) or resonant waveguide grating sensor (e.g., waveguide plate by Corning and SRU Biosystems).

In some embodiments, cells that have been stably or transiently transfected with a specific gene reporter construct, e.g. containing an inducible promoter co-operatively linked to a reporter gene that encodes an indicator protein, can be colorimetrically monitored for promoter induction. Cells are cultured on the array plates described herein and the effect of the immobilized compounds in the respective virtual wells on the expression of the transfected gene can be assessed. Those of skill will appreciate that the array plates described herein can be used with commercial monitoring systems known in the art, e.g. for assessing cellular processes, health, biochemical binding, or activity. For example, the Cytosensor Microphysiometer (Molecular Devices) evaluates cellular responses that are mediated by G protein-linked receptors, tyrosine kinase-linked receptors, and ligand-gated ion channels. It measures extracellular pH to assess profiles of compounds assessed for the ability to modulate activities of any of the these cell surface proteins by detecting secretion of acid metabolites as a result of altered metabolic states, particularly changes in metabolic rate. Receptor activation requires use of ATP and other energy resources of the cell thereby leading to increased cellular metabolic rate. Other examples include SPR or various forms of a waveguide. Monitoring may also be implemented by creating a binding surface in the wells or, alternatively, the wells could have some porosity such that electrical current, or small molecules could pass through the wells in response to an imposed gradient, force, diffusion or other basic physical phenomenon.

It is contemplated that, in some embodiments, stimulation may come from the planar surface of the "well," e.g. in the form of stimulatory molecules attached to the surface or if there is a gradient of molecules on the surface. Alternatively, an electrically active surface could be generated as would be used in MSD systems or for extracellular stimulation of cells. In still other embodiments, such surfaces of the "wells" could be used for magnetic entrapment or sensing.

Screening Assays

The array plates and devices described herein can be used in high-throughput screening, which encompasses biochemical, genetic, or pharmacological testing. Such screening assays can identify active compounds, antibodies, genes, proteins, peptides, lipids, carbohydrate, hormones, or other molecules which modulate the biomolecular pathway of interest or produce a desired effect. Results of these assays are useful in drug design, diagnosis, and/or studying the interaction with or role of particular biochemical processes. Accordingly, the present invention provides for the use of the novel array plates described herein in any screening assays practicable with traditional microtiter plates. Such assays include cell-based assays and biochemical assays.

In some embodiments of the invention, the method involves spotting an array of biological samples onto the oil-covered immobilization areas of the array plate and contacting each array droplet with a compound of interest. The compound may be selected from naturally occurring or synthetic molecules, an oligonucleotide such as a siRNA, ribozyme, or aptamer, a lipid, an oligosaccharide, a peptide, a protein, another cell type, or mixture thereof.

In some embodiments of the invention, the method of screening involves: a) providing a patterned surface comprising a hydrophobic surface with an array of hydrophilic immobilization areas, a plurality of said areas comprising cells immobilized on said areas and a cell culture medium, wherein said surface is covered by an immiscible medium; b) adding a compound to at least one of said areas; c) incubating said surface at a temperature suitable for cell culture; and d) detecting the effect of said compound on said cells. Accordingly, the present invention provides for the use of the novel array plates described herein in cell-based assays. The cell based assays could be run in singlicate or multiplicate and can be heterogeneous or homogeneous. Cell based assays could be run for a wide variety of purposes such as testing or predicting potency/activity, selectivity, toxicity/toxic effects, ADME properties, off target effects, or other properties.

Those of skill will appreciate that the array plates described herein have application in cell-based assays that can be run in a conventional microtiter plate. Common examples of cell-based screening assays include, without limitation, drug escalating dose response assays or IC50 assays, mitotic index assays, cell viability assays, cell death assays, and intracellular calcium mobilization assays, cell growth, cell morphology, cell interaction, protein trafficking or movement, molecular localization or movement, nucleic acid assays, metabolism assays, in addition to others known in the art. Biochemical screening assays are also practicable with the array plates of the present invention and includes, without limitation, enzyme activity assays (proteases, NADH-dependent enzymes, GST, phosphatases/kinases, etc.), ELISAs and other immunoassays (EIA (enzyme immunoassay), RIA (radioimmunoassay), etc.), protein quantitation, nucleic acid quantitation, genomic assays, and chemical measurements (ATP, reactive oxygen species, etc.), in addition to others known in the art.

In various screening assays of the present invention, the appropriate cells are deposited as arrays on the array plates for treatment and analysis. These arrays can be formed on the "virtual wells" of the array plates described herein, containing 96, 384, 1536, 3456 or more individual wells. As will be appreciated by those of skill in the art, these numbers are chosen for easy integration into conventional microtiter plate components and systems, although any number or geometric configuration can be used. These arrays can be of the same cell type and are treated with a combinatorial of distinct compounds, or alternatively, the arrays can be a combinatorial of cell types treated with one or more compounds. Such compounds include, without limitation, inhibitors, activators, potentiators and inducers.

In some embodiments, cells in arrays are treated with drugs or other naturally occurring or synthetic molecules, and the physiological response is measured temporally and spatially within a population of single living cells after an appropriate incubation period. Luminescent stains, dyes, and other small molecules can be used to measure the physiological response of living cells to drugs. Molecular-based chromophores expressed by the cells themselves (such as GFP and its mutants) are particularly suited to live cell measurements. These reagents can be used to measure the temporal and spatial intracellular changes of ions, metabolites, macromolecules, and organelles induced by drugs. Macromolecular-based indicators of cellular physiology can also be used in the assay. These luminscent analogs and biosensors can be used to measure the temporal and spatial changes in the distribution and activity of macromolecules such as protein, DNA, RNA, lipids, and carbohydrates in response to drug treatments.

In other embodiments, the cells are transiently or stably transfected with a DNA construct (either plasmid or viral based) that expresses a receptor of interest fused to an epitope tag at its amino terminus and a molecular based chromophore at its carboxy terminus. Alternatively, the receptor may be fused to an epitope tag at its carboxyl terminus and a molecular based chromophore at its amino terminus. The expression of the fusion receptor may be constitutive or inducible.

The appropriate cells are then patterned into arrays for treatment and analysis. These arrays can be formed on the "virtual wells" of the array plates described herein, containing 96, 384, 1536, or more individual wells. As will be appreciated by those of skill in the art, these numbers are chosen for easy integration into conventional microtiter plate components and systems, although any number or geometric configuration can be used. These arrays can be of the same cell type and are treated with a combinatorial of distinct compounds, or alternatively, the arrays can be a combinatorial of cell types treated with one or more compounds. Such compounds include, without limitation, inhibitors, activators, potentiators, and inducers.

Once the chosen cells are patterned into arrays, they are treated with solutions of candidate drugs or ligands to either inhibit or stimulate receptor internalization. The fluidic delivery system can be manual, robotic, or employ microfluidics. After an appropriate incubation period, the cells are fixed with a chemical crosslinking agent and stained with luminescence-based reagents. These reagents include, but are not limited to, luminescently labeled primary or secondary antibodies that react with the receptor, the epitope tag, or other cellular antigens determined to correlate with internalization of the receptor. Luminescent stains, dyes, and other small molecules can also be used to measure the physiological response of the cells to drugs. These reagents are used to measure the temporal and spatial changes in ions, metabolites, macromolecules, and organelles induced by drugs. Macromolecular-based indicators of cellular physiology can also be used in the assay.

In some embodiments of the invention, cells in arrays are treated with candidate drugs, and the physiological response is measured temporally and spatially within a population of single living cells after an appropriate incubation period. Luminescent stains, dyes, and other small molecules can be used to measure the physiological response of living cells to drugs. Molecular-based chromophores expressed by the cells themselves (such as GFP and its mutants) are particularly suited to live cell measurements. These reagents can be used to measure the temporal and spatial intracellular changes of ions, metabolites, macromolecules, and organelles induced by drugs. Macromolecular-based indicators of cellular physiology can also be used in the assay. These luminscent analogs and biosensors can be used to measure the temporal and spatial changes in the distribution and activity of macromolecules such as protein, DNA, RNA, lipids, and carbohydrates in response to drug treatments.

In another embodiment, fluorescently labeled ligand is used to induce receptor sequestration and the fate of the ligand is assayed as a parameter of the high-content screen.

The array plates of the present invention are useful at the stage of ADMET (absorption, distribution, metabolism, excretion, and toxicology) testing after a number of potential drug leads have been derived and the pool of biochemically efficacious compounds must be winnowed down for further development as a pharmaceutical compound. For instance, for metabolism studies, compound can be tested for their propensity to be degraded by various cytochrome P-450 (CYP-450) enzymes or by liver microsome preparations. Propensity of causing drug-drug interactions can be estimated by assaying for inhibition of various CYP450 enzymes by a given drug or candidate drug. Accordingly, the present invention provides for measurement of cellular metabolism of compounds from a library. As described above, the compound to be assayed may be selected from a small molecule, lipid, peptide, oligonucleotide, or oligosaccharide. The cells can be suspended in liquid medium within the "virtual wells" of the array plate, which are individually formed by the hydrophobic interaction and surface tension of the halogenated hydrocarbon, e.g. perfluorocarbon, with the hydrophobic areas on the surface of the array plate and the liquid medium, respectively. The "virtual wells" are then loaded with volumes of known concentrations of compound(s) from the library to determine the change in compound composition or amount with cellular metabolism.

In other embodiments, the present invention provides for the measurement of cellular toxicity of compounds from a library. As described above, the compound to be assayed may be selected from a small molecule, lipid, peptide, oligonucleotide, or oligosaccharide. The cells can be suspended in liquid medium within the "virtual wells" of the array plate, which are individually formed by the hydrophobic interaction and surface tension of the halogenated hydrocarbon, e.g. perfluorocarbon, with the hydrophobic areas on the surface of the array plate and the liquid medium, respectively. The "virtual wells" are then loaded with volumes of known concentrations of compound(s) from the library to determine the level of cellular toxicity.

In still other embodiments, the present invention provides for the affinity measurement or affinity ranking of various members of a compound library toward a given target molecule or the measurement of analyte affinity toward various members of a probe array. Such screening can be carried out using the new methods described herein. For example, affinity experiments can be carried out by immobilizing a target in the immobilization area(s) of the array plate described herein and probing with a library of candidate ligands, or by immobilizing a ligand library in an array and probing with a target. As described above, the compound to be assayed may be selected from a small molecule, lipid, peptide, oligonucleotide, or oligosaccharide. The cells can be suspended in liquid medium within the "virtual wells" of the array plate, which are individually formed by the hydrophobic interaction and surface tension of the halogenated hydrocarbon, e.g. perfluorocarbon, with the hydrophobic areas on the surface of the array plate and the liquid medium, respectively. The "virtual wells" are then loaded with volumes of known concentrations of compound(s) from the library to determine the affinity of the compound(s) for a given target.

In alternative embodiments, the affinity of various members of a compound library toward a given target molecule can be determined by immobilizing the target molecule on the immobilization area(s) of the array plate, loading volumes of known concentration of compound(s) from the library, detecting those members of the array that retain a compound, subjecting the array to thermal denaturation or denaturing solvent condition, then detecting unfolding of the target molecule as a function of temperature of denaturing solvent condition. Those of skill in the art will appreciate that bound compounds will confer stabilize target molecules to thermal denaturation to a degree that can correlate with the degree of affinity. By detecting unfolding of protein as a function of temperature or denaturing solvent condition, affinities can be ranked, as described, for example, in U.S. Pat. No. 6,020,141 to Pantoliano et al. As described above, the compound to be assayed may be selected from a small molecule, lipid, peptide, oligonucleotide, or oligosaccharide. The cells can be suspended in liquid medium within the "virtual wells" of the array plate, which are individually formed by the hydrophobic interaction and surface tension of the halogenated hydrocarbon, e.g. perfluorocarbon, with the hydrophobic areas on the surface of the array plate and the liquid medium, respectively.

In some embodiments, the present invention provides for cancer screening assays using the array plates described herein. An appropriate sample is deposited onto "virtual wells" of the array plates described herein, containing 96, 384, 1536, or more individual wells. A sample, for example, may be a biological fluid taken from an individual. In preferred embodiments, the biological fluid is of human origin. Exemplary biological fluids include blood, serum, plasma, cerebrospinal fluid, synovial fluid, urine, or saliva. In preferred embodiments, the biological fluid is selected from whole blood, serum, plasma, and a fraction or processed derivative thereof. In some embodiments, the nucleic acid in the biological sample is amplified and quantified to assess the risk or state of developing cancers. In some embodiments, the nucleic acid in the biological sample to be amplified is oncogenic mRNA. In other embodiments, the nucleic acid in the biological sample to be amplified is viral DNA or RNA. For example, high-risk types of human papillomavirus (hrHPV) are known to be causative agents of cervical cancer. An exemplary screening assay for the risk of developing cervical cancer could be conducted by i) amplifying viral DNA by established GP5+/6+PCR; ii) capturing biotinylated GP5+/6+PCR product in streptavidin-coated array plates described herein; iii) high stringency hybridizing of PCR products with labelled hrHPV-specific probes; iv) detecting label by a conjugate and visualizing by addition of substrate; and v) measuring optical density to determine presence of hrHPV.

In some embodiments, the array plate is engaged for biochemical assays where a series of reagents is added to the array for incubation and detection without involving any reagents and materials intentionally interacting with the array surface. In such application, the array plate may be washed, cleaned, dried, and reused for biochemical assays. The washing process of the used plate may involve washing with aqueous and organic solution such as phosphate buffer saline, alcohol, or dimethyl sulfoxide in order to remove non-specifically adsorbed reagents and materials from the surface. The structure of the array plate of a flat array surface facilitates reasonably clean and complete washing of the array surface. After washing, the array plate may be reused.

IV. Detection of Assays

A variety of detection methods known in the art may be used in conjunction with the present invention, as those of skill would appreciate. These include, for example, H Thymidine, colorimetric methodologies, fluorescence methodologies such as Alpha, DELFIA (dissociation-enhanced lanthanide fluorescent immunoassay), FP (fluorescence polarization detection), TRF (time-resolved fluorescence), TR-FRET (time-resolved fluorescence resonance energy transfer), and LANCE, luminescence, and radiometry. In some embodiments, the target antigen or antibody is immobilized on a surface of the array plate described herein. An aliquot of sample is added to discrete immobilization areas of the solid support and allowed to incubate with the target antigen or antibody in a liquid phase. An immunoglobulin (otherwise referred to herein as a secondary antibody) selected to recognize the antigen or antibody being assayed for is then added. In preferred embodiments, the secondary antibody is characterized by an IgG isotype. After separating the solid support from the liquid phase, the support phase is examined for a detectable signal. The presence of the signal on the solid support indicates the presence of antibodies to the target antigen or the presence of antigens defining the epitope of the target antibodies in the sample.

The signal producing system can include one or more components, at least one of which is a label, which generate a detectable signal that relates to the amount of bound label. The label is a molecule that produces or which may be induced to produce a signal. Detectable labels suitable for such use include any composition detectable by spectroscopic, photochemical, biochemical, immunochemical, electrical, optical or chemical means. Examples of suitable labels include fluorescers, enzymes, chemiluminescers, photosensitizers or suspendable particles. The signal is detected and may be measured by detecting enzyme activity, luminescence or light absorbance.

Useful labels in the present invention include magnetic beads (e.g., DYNABEADS), fluorescent dyes (e.g., fluorescein isothiocyanate, Texas red, rhodamine, green fluorescent protein, and the like), radiolabels (e.g., 3H, 125I, 35S, 14C, or 32P), enzymes (e.g., horseradish peroxidase, alkaline phosphatase and others commonly used in an ELISA), and colorimetric labels such as colloidal gold or colored glass or plastic (e.g. polystyrene, polypropylene, latex) beads. A general overview of the applicable technology can be found in Harlow & Lane, Antibodies: A Laboratory Manual (1988).

Although radiolabels may also be used and levels of radioactivity detected and measured using a scintillation counter, it is not preferred due to safety and environmental concerns. The most commonly used producing systems employ enzyme-mediated chromogenic or fluorophore-mediated fluorescent mechanisms. With chromogenic reporters, any bound enzyme label is then reacted with a substrate to yield a colored product that can be analyzed with a light microscope. Examples of additional enzymes labels which may be used include, without limitation, β-D-galactosidase, glucose-6-phosphate dehydrogenase ("G6PDH"), and glucose oxidase.

With fluorescent reporting systems, the fluorophores are conjugated to a probe or the secondary antibody and do not require a substrate to activate the enzyme as in chromogenic detection systems. Furthermore, fluorescent reporting systems are particularly useful in multiplex assays. Examples of fluorescer labels that can be used include, without limitation, fluorescein, isothiocyanate, rhodamine compounds, phycoerythrin, phycocyanin, allophycocyanin, o-phthaldehyde and fluorescamine. Chemiluminescers include e.g., isoluminol.

The amount or intensity of color, fluorescence, luminescence, or radioactivity present in the reaction (depending on the signal producing system used) should correlate with the concentration of autoantibodies in a sample. Quantification of optical density may be performed using spectrophotometric methods. Quantification of radiolabel signal may be performed using scintillation counting. Where enzyme labels are used, the enzymatic activity is dependent on severail variables, including enzyme nd substrate concentration, buffer, pH, temperature, and possibly light. Enzyme-substrate systems that can be employed are described in the art and may include, without limitation, DAB-HRP; metal-enhanced DAB-HRP; BCIP-AP; NBT-AP and glucose oxidase; 1-step NBT-BCIP and AP, etc.

Enzymes may be covalently linked to target antigen reactive antibodies for use in the methods of the invention using methods known to those of ordinary skill in the art. For example, alkaline phosphatase and horseradish peroxidase may be conjugated to antibodies using glutaraldehyde. Horseradish peroxidase may also be conjugated using the periodate method. Commercial kits for enzyme conjugating antibodies are widely available. Enzyme conjugated anti-human and anti-mouse immunoglobulin specific antibodies are available from multiple commercial sources.

Alternatively, indirect detection of the antiautobodies may be effected using avidin-biotin complex method, labeled streptavidin biotin method, or phosphatase-anti-phosphatase method as familiar to those of ordinary skill in the art.

Enzyme labeled antibodies produce different signal sources, depending on the substrate. Signal generation involves the addition of substrate to the reaction mixture. Common peroxidase substrates include 3,3'-diaminobenzidine (DAB), ABTS™2,2'-azinobis(ethylbenzothiazoline-6-sulfonate)), OPD (O-phenylenediamine) and TMB (3,3', 5,5'-tetramethylbenzidine). p-nitrophenyl phospate is a commonly used alkaline phosphatase substrate. Where alkaline phosphtase enzyme label is employed, the substrate is selected as a combination of nitro blue tetrazolium chloride (NBT) and 5-bromo-4-chloro-3-indolyl phosphate (BCIP). Where glucose oxidase enzyme label is employed, the substrate is selected to be nitro blue tetrazolium chloride. Where a β-galactosidase enzyme label is employed, the substrate is selected to be 5-bromo-4-chloro-3-indoyl-β-D-galactopyranoside (BCIG or X-Gal). During an incubation period, the enzyme gradually converts a proportion of the substrate to its end product. At the end of the incubation period, a stopping reagent may be added which stops enzyme activity. Signal strength is determined by measuring optical density, usually via spectrophotometer.

Alkaline phosphatase labeled antibodies may also be measured by fluorometry. Thus in the immunodetection methods of the present invention, the substrate 4-methylumbelliferyl phosphate (4-UMP) may be used. Alkaline phosphatase dephosphorylated 4-UMP to form 4-methylumbelliferone (4-MU), the fluorophore. Incident light is at 365 nm and emitted light is at 448 nm.

V. Methods of Transferring Samples from Virtual Wells

Still another method features transfer of contents from the virtual wells of the array plate into microtiter plates. In order to recover samples giving a positive response to a test, there is often a need to transfer fluid from selected virtual wells in a high-density array plate to a microtiter plate having a lower density of wells. Often, this transfer process must be performed with sterile technique. This will allow for sampling of materials held in virtual wells with selected properties from a larger collection of samples. There are three general methods for transferring fluids from the high density array plate to the wells of a microtiter plate: transfer with a single sampling device, transfer with a linear array of sampling devices and transfer with a two-dimensional array of sampling devices. Samples from the selected virtual wells can be removed by spatially localized mechanical action.

VII. Spectrometric Analysis of Compounds in an Array of Virtual Wells

Atmospheric Pressure Ionization Mass Spectrometry (API-MS)

Samples in an array of virtual wells of the array plate described herein can be analyzed by a spectrometric technique such as atmospheric pressure ionization mass spectrometry (API-MS). The spectrometric analyses are typically performed serially. Therefore, the chips should be environmentally isolated in a controlled temperature and humidity environment to avoid loss of sample due to evaporation. In API-MS, one simple method for introducing the sample to the mass spectrometer features aspirating a selected sample directly from a particular virtual well into a valve using a length of capillary tubing or drawn up with a capillary sipper. A metered volume of sample can then be introduced into a mass spectrometer using standard API-MS protocols.

Matrix Assisted Laser Desorption Ionization Time of Flight Mass Spectrometry (MALDI TOF-MS)

In MALDI TOF-MS analysis, a sample of interest is generally mixed with one or more matrix-forming compounds. Typically, a saturated solution of an organic matrix material (e.g., derivatives of hydroxycinnamic acid) is mixed with an equal volume of sample. In some applications of MALDI TOF-MS, the organic matrix compound is replaced by inorganic nanoparticles (e.g., colloidal gold, quantum dots, or porous silica). The mixture is then spotted in the form of a regular and addressable array on the array plate and allowed to evaporate. The sample plate is then positioned in the mass spectrometer, and the samples are ionized by irradiation from a pulsed laser.

The laser used for sample ionization in the MALDI TOF mass spectrometer can be focused within the virtual wells to provide the necessary irradiance for sample ionization. Internal reflection of the laser beam within the virtual wells can possibly increase the amount of laser energy absorbed by the matrix and transferred to the sample, thereby increasing the amount of sample ionization. Additionally, an array of virtual wells can allow for a very high density of samples to be spatially located in a small footprint without cross-contamination.

Typical MALDI-MS sample plates are solid surfaces onto which samples are spotted. The laser used to ionize the samples must be on the same side of a conventional MALDI-MS plate as the inlet of the flight tube of the mass spectrometer, since the sample plate is opaque to the laser energy. In some embodiments where the array plate of the present invention is used as the MALDI-MS plate and has a transparent surface, the source of laser irradiation and the inlet to the TOF mass spectrometer can be located on opposite faces of the array plate. Translocation of the array plate in front of the inlet of the flight tube allows for the laser ionization of a selected sample.

Alternatively, an array of posts or pins, precision-machined to fit into an array of virtual wells, can be coated with the MALDI matrix material by dipping the array into a bulk matrix solution. After the solvent has evaporated, the pin array can be inserted into the array of virtual wells. Fluid contained in each virtual well is transferred to the corresponding pin surface. After the solvent has evaporated, the pin array can be placed at the input to a TOF mass spectrometer and the pins can be illuminated sequentially with a focused laser beam. In such a pin array, a portion of the sample from each through-hole can be held isolated from its neighbor by the air gap between each pin.

A Device for the Analysis of an Array of Virtual Wells by Mass Spectrometry

Samples or aliquots of samples can be removed from an array of virtual wells for analysis by mass spectrometry by one of several different methods. One such method features drawing the sample or an aliquot thereof into a tube with the application of negative pressure. In one example of this approach, the tip of a syringe is inserted into a selected virtual well in an array and a metered amount of sample is drawn into the syringe. Alternatively a vacuum could be used to aspirate the samples into a length of tubing, a valve, or a container for storage.

For certain applications, it can be desirable to assay each sample in an array of virtual wells by a serial process such as mass spectrometry. Application of a serial process to a large number of samples in an array of samples on a conventional microtiter plate, even if done very rapidly, can still require a significant amount of time. If humidity conditions and temperature are not strictly regulated during this time, evaporation of samples from the physical wells of a conventional microtiter plate can occur and artificially bias assay results.

Accordingly, the present invention provides for a method of controlling evaporation from the virtual wells of an array plate. As described above, the virtual well is formed in part by a film of fluorinated hydrocarbon, e.g. perfluorocarbon, which interacts hydrophobically with the hydrophobic surfaces of the array plate to form a barrier to evaporation. The syringe needle used for aspirating the sample out of the virtual wells can easily perforate this thin film and will not hinder efficient sampling.

Once the sample is aspirated into a syringe, it can be delivered into a mass spectrometer for analysis by any one of many techniques known by those skilled in the art. These can include atmospheric pressure ionization techniques such as electrospray ionization (ESI) or atmospheric pressure chemical ionization (APCI).

In another embodiment of the invention, an array of pins coregistered with the array of virtual wells can be dipped into the array of virtual wells then withdrawn therefrom. Sample that is residually removed from the array of virtual wells can be allowed to evaporate on the tips of the array of pins. As in the previous embodiment, this evaporated sample can be used for a surface based mass spectrometry method.

VIII. Flow Cytometry Analysis of Compounds from an Array of Virtual Wells

Samples in an array of virtual cells of the array plate described herein can also be analyzed by a flow cytometry technique. In flow cytometry, a beam of light is directed onto a hydro-dynamically focused stream of fluid and a number of detectors are aimed at the point where the stream passes through the light beam, one in line with the light beam, i.e. forward scatter or FSC, and several perpendicular to it (side scatter or SSC), and optionally one or more fluorescent detectors, e.g. in embodiments where the particles in the stream have been fluorescently tagged or where flow cytometers use only light scatter for measurement. Analysis of the fluctuations in brightness at each detector can derive data for various parameters such as the physical and chemical structure of each individual particle. In some embodiments, the particle is a whole cell.

An exemplary method for introducing the sample to a flow cytometer features aspirating a selected sample directly from a particular virtual well into a valve using a length of capillary tubing or drawn up with a capillary sipper. A metered volume of sample can then be introduced into a flow cytometer using standard protocols. In some embodiments, the flow cytometer is a fluorescence activated cell sorter (FACS), which can separate and isolate particles having certain properties. FACS can be used to analyze expression of cell surface and intracellular molecules, characterize and define different cell types in heterogeneous cell populations, assess purity of isolated subpopulations, and analyze cell size and volume. Tagging of cell-surface molecules can be performed directly or indirectly. The tagging procedure involves making a suspension from cell culture or tissue samples. The cell suspension can be incubated with primary labeled antibodies (in direct cell surface tagging) or incubated successively with primary antibodies and fluorochrome-labeled secondary antibodies (in indirect cell surface tagging) in tubes, conventional microtiter plates, or the array plates described herein, then analyzed on the flow cytometer. As those of skill in the art would appreciate, the choice of fluorochrome is influenced by a plurality of factors, such as the photomultiplier voltage, type of signal amplification, available filters, autofluorescence of the cells to be analyzed, and other optical parameters.

IX. Time-Gated Fluorescence Imaging of a Virtual Well-Array

Many biological assays are configured to give a fluorescent readout that can be acquired from an array of virtual wells by fluorescence imaging. Typically, light from an excitation lamp or laser is passed through an excitation filter, through the array, through an emission filter and then to a CCD camera. In many cases, the sensitivity of the signal is limited by background light due to imperfect performance of the filters, and by inelastic and elastic scattering of light by the sample and optical components. Whereas the fluorophores of interest have fluorescence lifetimes of about 1 ns to 1 ms, scattering occurs at much shorter timescales. Thus removal of background light can be accomplished by the technique of time-gating. Time-gating the process of illuminating the sample while preventing the camera from acquiring data, quickly removing the excitation light, then waiting for a delay time before acquiring the fluorescence emission image. By not collecting photons emitted during the first 1 to 100 ps of after excitation, background noise is significantly reduced and signal to noise is improved. A similar apparatus can be used to repeat the data acquisition with varying delay times, thus yielding fluorescence lifetime information for each of the through-holes in the array.

Various strategies can be used to construct a time-gated fluorescence imaging system. A pulsed excitation source is needed and can be either a flash lamp or laser such as a passive or active mode-locked or Q-switched laser. If a laser is used, a beam expander and diffuser plate will give uniform irradiation of the platen. A continuous excitation source can also be used with a means for rapidly blocking and un-blocking the light such as an electro-optical, an acousto-optical cell or a rapidly rotating disk with slits. A pulse generator can be used to trigger the illumination source and detector at a given delay. The CCD camera can be electronically shuttered or physically shuttered as with a rotating disk with slits that is out of phase with the excitation pulsing.

EXAMPLES

Examples are provided below to illustrate the present invention. These examples are not meant to constrain the present invention to any particular application or theory of operation.

Example 1: Primary Cell Culture Feasible with Different Coating(s) on DropArray™ 96-Well Plate As previously described, the immobilization member of the array plate can be coated or covalently linked with biological moieties as deemed suitable by one of ordinary skill in the art for a given biochemical, screening, or cellular assay. Various coating options may be employed for cell culture. In general, the procedure for coating a DropArray plate is similar to coating conventional microtiter plates, except that the amount of coating should be adjusted based on the surface area of a DropArray™ 96 well plate (diameter 3.5 mm). Conditions for attachment can be optimized by one of skill in the art for each cell line and application.

Example 1A: Exemplary Guidelines for Preparing Various Coatings

Collagen Type I
Add collagen to 0.1 M acetic acid to obtain a 1 mg/ml collagen solution. Stir at room temperature for 1-3 hours until dissolved, then dilute collagen solution to obtain a working concentration of 50-100 μg/ml.

Collagen Type II and IV
Collagen Types II and IV may be reconstituted to a concentration of about 0.5-2.0 mg/ml in 0.25% acetic acid. Dissolve for several hours at 2-8° C., occasionally swirling.

Gelatin:
1) Dissolve gelatin powder in sterile MilliQ water (0.1%) by gently swirling mixture for 15 minutes in a 60° C. water bath. In some embodiments, a microwave is not used to dissolve gelatin in water as the resulting solutions may vary widely in behavior.
2) Cool the gelatin solution at room temperature, and, while still warm (~37-40° C.), filter it through a 0.45 μm cellular acetate membrane (CA). The gelatin solutions should have a shelf life of at least 1 month when stored at 4° C. When ready for coating, warm solution for 30 minutes in a 40° C. water bath.

PDL
1) Prepare PDL Coating solution. Dissolve 5 mg poly-D-lysine (Sigma # P6407 5 mg) in 50 ml COLD 0.1M Borate Buffer, pH 8.5.
2) Rock for 1 hour at room temperature to dissolve.
3) Filter with 0.2 micron filter to sterilize.

PDL/Laminin
1) Prepare coating solution with the following materials:
    a. 5 mg poly-D-lysine (Sigma # P6407 5 mg)
    b. 50 ml COLD 0.1M Borate Buffer, pH 8.5
    c. Natural Mouse Laminin (Invitrogen #23017-015 1 mg/ml)
2) Dissolve 5 mg PDL in 50 ml cold 0.1 M Borate buffer. Rock for 1 hour at room temperature to dissolve.
3) Filter with 0.2 micron filter to sterilize.
4) Add 25 μl Laminin into 10 ml PDL-Borate buffer, mix well.

Example 1B: Exemplary Work Flow Diagram for Primary Cell Culture

Figure 34A:
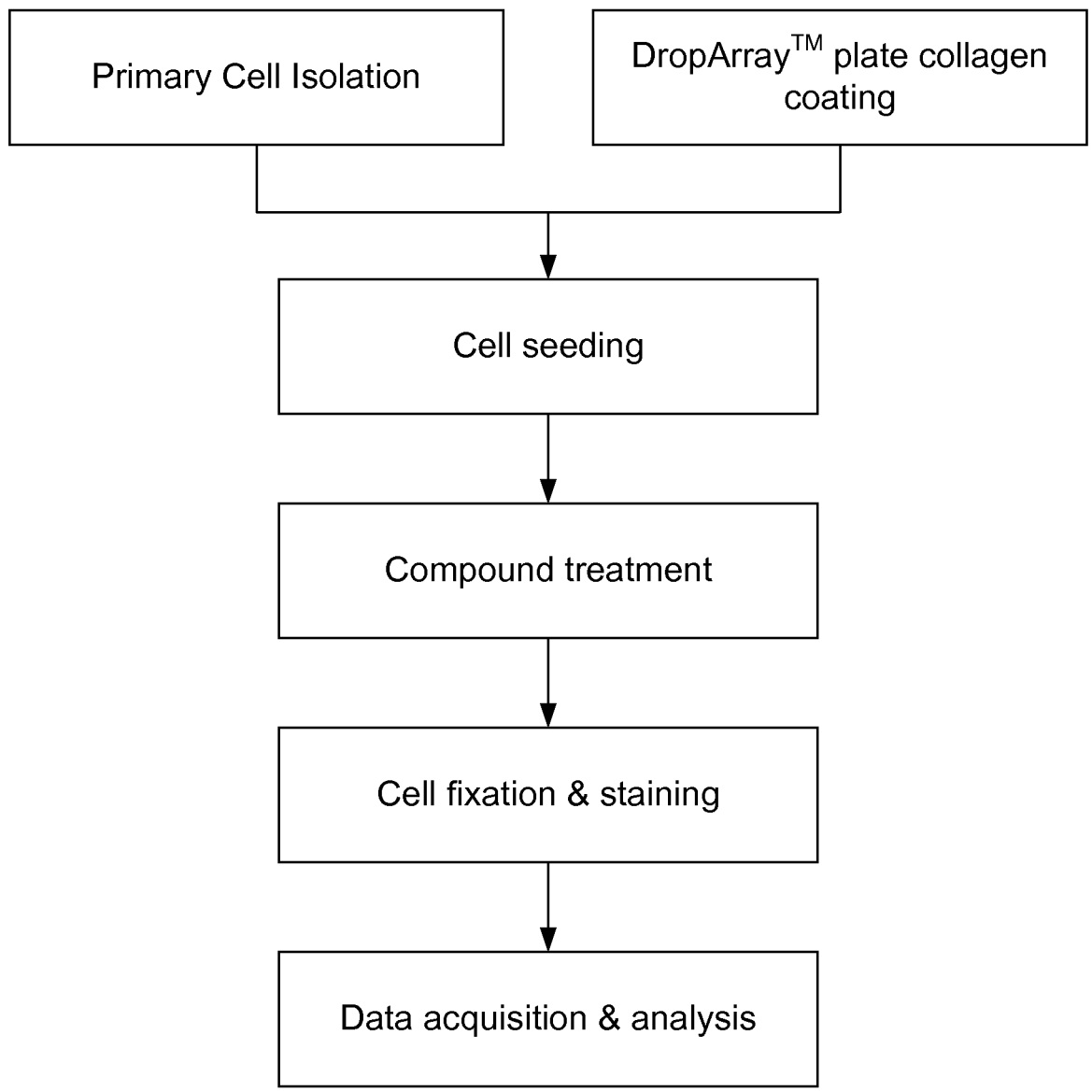
FIG. 34A is an exemplary work flow diagram for primary cell culture.

Please see FIG. 34A.

Example 1C: Exemplary Coating Procedures

1) Dispense coating solution at 8 μl/well.
2) Overlay with 4 ml rinsing fluid.
3) Incubate the plate with lid for 1 hour at room temperature, or in a 37° C. incubator.
4) Wash with 2×ddH$_2$O or medium using Curiox HT washing station or manually.
5) For manual washing, tap out any excess aqueous drops that may be retained on the plate.
6) Use the plate immediately, or air dry the plates overnight and store the coated plate at 2-8° C.

The coated plates can maintain stability for at least two weeks when stored at 2° C. to 8° C. in an air-tight environment. As those of skill in the art would appreciate, care should be taken to avoid drying out of the coated surface. Optionally, dried coated dishes can be sterilized by exposure to UV light in a sterile culture hood or by rinsing with 70% ethanol.

Example 1D: Exemplary Cell Preparation Procedures

1) Prepare primary cells in appropriate medium and cell concentration.
2) Seed cells on coated DropArray™ 96-well cell plate at density of 250-2500 cells/well/10 μl.
3) Overlay with 15 ml of sterile incubation fluid, dispense gently from the "P24" corner of plate.
4) Incubate cells for further treatment.

Example 1E: Exemplary Cell Fixation Procedures

1) Dummy wash 1× with 1×PBS using the Curiox HT/LT washing station.
2) Prepare 4% formaldehyde fresh from 37% stock in 1×PBS, pre-warmed at 37° C. water bath for 15-30 minutes in dark.
3) Replace incubation fluid with rinsing fluid for the cell plate.
4) Drain rinsing fluid for 5 seconds by holding plate at an angle of more than 120°.
5) Flood plate with 25-30 ml of 4% pre-warmed formaldehyde or wash assay plate 3× with 1×PBS and then dispense 10 μl of 4% pre-warmed formaldehyde, then top-up rinsing fluid to 10 ml to cover the drops.
6) Incubate at room temperature for 15 minutes. Alternatively, dispense concentrated fixing solution to the droplet directly.
7) Wash assay plate 3× with 1×PBS using the Curiox HT/LT washing station. Add 3 ml of rinsing fluid.

Example 1F: Exemplary Cell Permeabilization Procedures

1) Dispense 10 μl of 1× permeabilization buffer into each well.
2) Top-up rinsing fluid to 10 ml to cover the drops.
3) Incubate at room temperature for 15 minutes.
4) Wash assay plate 2× with 1×PBS using the Curiox HT HT/LT washing station. After wash, add 3 ml of rinsing fluid.

Example 1G: Exemplary Antibody and Nuclear Staining Procedures

1) Dispense 10 µl of diluted primary antibody into each well.
2) Top-up rinsing fluid to 10 ml to cover the drops.
3) Incubate at RT for 1 hour.
4) Wash assay plate 2× with 1×DPBS using the HT Curiox HT/LT washing station. After wash, add 3 ml of rinsing fluid.
5) Dispense 10 µl of diluted secondary antibody and Hoechst 33342 nuclear stain into each well.
6) Top-up rinsing fluid to 10 ml to cover the drops.
7) Incubate at room temperature for 1 hour in dark.
8) Wash assay plate 2× with 1×DPBS using the HT Curiox HT/LT washing station. After wash, add 5 ml of rinsing fluid immediately.
9) Seal plate with aluminum seals.
10) Follow appropriate scanning procedure compatible with the imager selected for use.
11) Store plate at 4° C. f plate is not sent for scanning immediately.

Example 2: Primary Cell Culture Feasible with Different Coating(s) on DropArray™ 384-Well Plate As previously described, the immobilization member of the array plate can be coated or covalently linked with biological moieties as deemed suitable by one of ordinary skill in the art for a given biochemical, screening, or cellular assay. Various coating options may be employed for cell culture. In general, the procedure for coating a DropArray plate is similar to coating conventional microtiter plates, except that the amount of coating should be adjusted based on the surface area of a DropArray™ 384 well plate (diameter 2.0 mm). Conditions for attachment can be optimized by one of skill in the art for each cell line and application.

Example 2A: Exemplary Guidelines for Preparing Various Coatings

Collagen Type I
  Add collagen to 0.1 M acetic acid to obtain 1 mg/ml collagen solution. Stir at room temperature 1-3 hours until dissolved. Then dilute collagen solution to obtain a working concentration of 50-100 µg/ml.

Collagen Type II and IV
  Collagen Types II and IV may be reconstituted to concentration of 0.5-2.0 mg/ml in 0.25% acetic acid. Dissolve for several hours at 2-8° C., occasionally swirling.

Gelatin:
  1) Dissolve gelatin powder in sterile MilliQ water (0.1%) by gently swirling mixture for 15 minutes in a 60° C. water bath. In some embodiments, a microwave is not used to dissolve gelatin in water as the resulting solutions may vary widely in behavior.
  2) Cool the gelatin solution at room temperature, and, while still warm (~37-40° C.), filter it through a 0.45 µm cellular acetate membrane (CA). The gelatin solutions do not deteriorate for at least 1 month when stored at 4° C. When ready for coating, warm for 30 minutes in a 40° C. water bath.

PDL
  1) Prepare PDL Coating solution.
    Dissolve 5 mg poly-D-lysine (Sigma # P6407 5 mg) in 50 ml COLD 0.1M Borate Buffer, pH 8.5.
  2) Rocking for 1 hour at room temperature to dissolve.
  3) Filter with 0.2 micron filter to sterilize.

PDL/Laminin
  1) Prepare coating solution
    a. 5 mg poly-D-lysine (Sigma # P6407 5 mg)
    b. 50 ml COLD 0.1M Borate Buffer, pH 8.5
    c. Natural Mouse Laminin (Invitrogen #23017-015 1 mg/ml)
  2) Dissolve 5 mg PDL in 50 ml cold 0.1 M Borate buffer. Rocking for 1 hour at room temperature to dissolve.
  3) Filter with 0.2 micron filter to sterilize.
  4) Add 25 µl Laminin into 10 ml PDL-Borate buffer, mix well.

Example 2B: Exemplary Work Flow Diagram for Primary Cell Culture

Figure 34B:
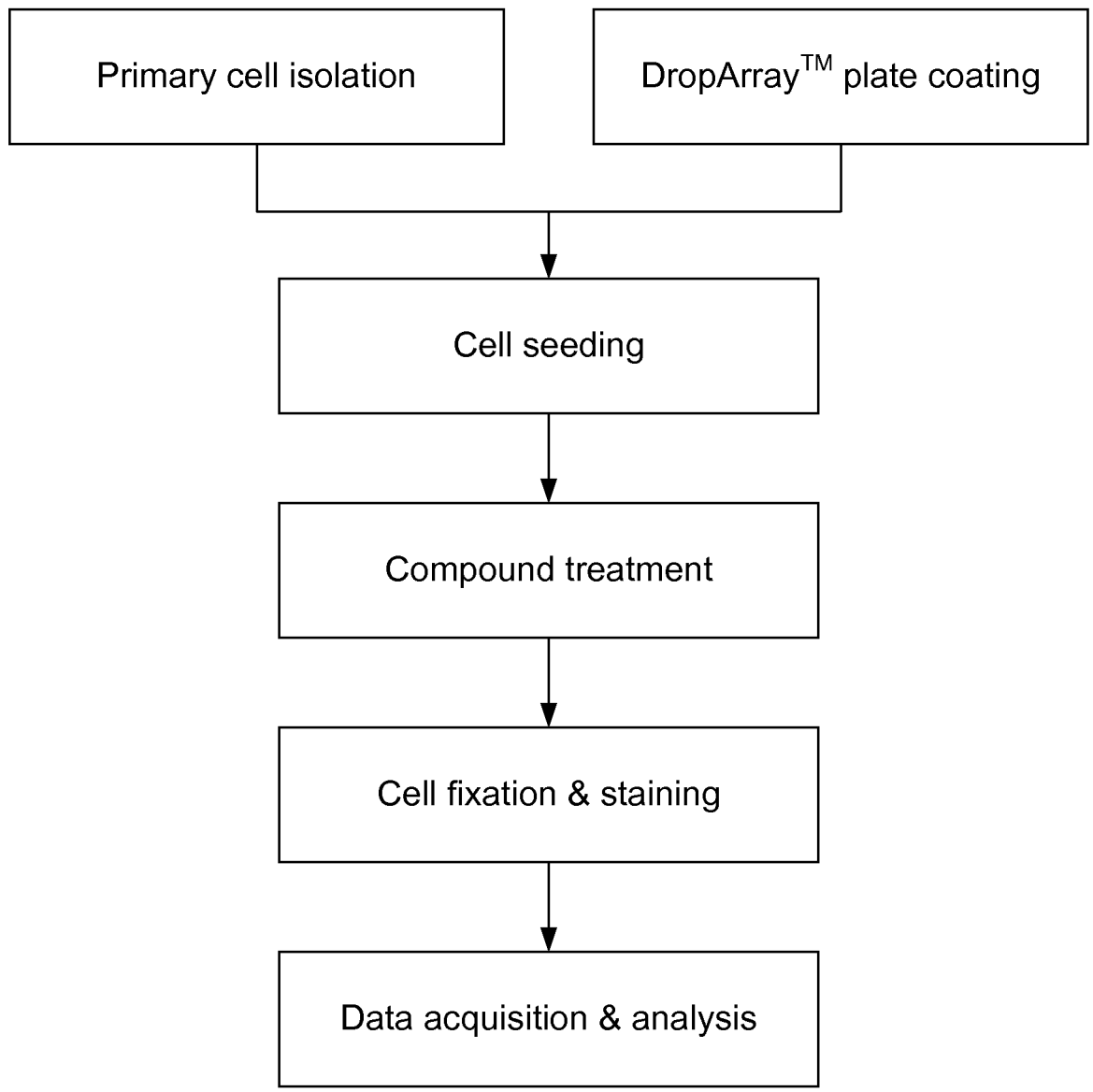
FIG. 34B is an exemplary work flow diagram for primary cell culture.

Please see FIG. 34B.

Example 2C: Exemplary Coating Procedures

1) Dispense 3 µl/well using automatic dispenser(s).
2) Overlay with 2 ml Rinsing fluid.
3) Incubate the plate with lid for 1-4 hour at room temperature or at 37° C. incubator, or overnight at 2-8° C.
4) Wash with 2×ddH$_2$O or medium using Curiox HT washing station or manually. (Keep in mind that DropArray Washing station provides evenly washing result across the wells and consistent results between plates.)
5) For manual washing, tap out any excess aqueous drops that may be retained on the plate.
6) Use the plate immediately, or air dry the plates overnight and store the coated plate at 2-8° C.

The coated plates can maintain stability for at least two weeks when stored at 2° C. to 8° C. in an air-tight environment. As those of skill in the art would appreciate, care should be taken to avoid drying out of the coated surface. Optionally, dried coated dishes can be sterilized by exposure to UV light in a sterile culture hood or by rinsing with 70% ethanol.

Example 2D: Exemplary Cell Preparation Procedures

1) Prepare primary cells in appropriate medium and cell concentration.
2) Seed cells on coated DropArray™ 384-well cell plate (Catalog #384-PT-TC-01) at density of 60-600 cells/well/41 using Multi-Drop combi at the dispensing speed 3 (fastest speed).
3) Overlay with 15 ml of sterile incubation fluid, dispense gently from the "P24" corner of plate.
4) Incubate cells for further treatment.

Example 2E: Exemplary Cell Fixation Procedures

1) Dummy wash 1× with 1×PBS using the Curiox HT/LT washing station.
2) Prepare 4% formaldehyde fresh from 37% stock in 1×PBS, pre-warmed at 37° C. water bath for 15-30 minutes in the dark.
3) Replace incubation fluid with rinsing fluid for the cell plate.

4) Drain rinsing fluid for 5 seconds by holding plate more than 120°
5) Flood plate with 25-30 ml of 4% pre-warmed formaldehyde or wash assay plate 3× with 1×PBS and then dispense 2 µl of 4% pre-warmed formaldehyde, then top-up rinsing fluid to 10 ml to cover the drops
6) Incubate at room temperature for 15 minutes
7) Wash assay plate 3× with 1×PBS using the Curiox HT/LT washing station. Add 3 ml of rinsing fluid immediately.

Example 2F: Exemplary Cell Permeabilization Procedures

1) Dispense 2 µl of 1× permeabilization buffer into each well.
2) Top-up rinsing fluid to 10 ml to cover the drops.
3) Incubate at room temperature for 15 minutes.
4) Wash assay plate 2× with 1×PBS using the Curiox HT HT/LT washing station. After wash, add 3 ml of rinsing fluid.

Example 2G: Exemplary Antibody and Nuclear Staining Procedures

1) Dispense 2 µl of diluted primary antibody into each well.
2) Top-up rinsing fluid to 10 ml to cover the drops.
3) Incubate at room temperature for 1 hour.
4) Wash assay plate 2× with 1×DPBS using the HT Curiox HT/LT washing station. After wash, add 3 ml of rinsing fluid.
5) Dispense 2 µl of diluted secondary antibody and Hoechst 33342 nuclear stain into each well.
6) Top-up rinsing fluid to 10 ml to cover the drops.
7) Incubate at room temperature for 1 hour in dark.
8) Wash assay plate 2× with 1×DPBS using the HT Curiox HT/LT washing station. After wash, add 5 ml of rinsing fluid immediately.
9) Seal plate with aluminum seals.
10) Follow appropriate scanning procedure compatible with the imager selected for use.
11) Store plate at 4° C. if plate is not sent for scanning immediately.

Example 3: Autophagy Assay

High content imaging of cell-based assay(s) can be also performed on the DropArray platform. To illustrate, the DropArray platform is useful for assaying autophagy, a homeostatic process by which cells break down their own components, via transport of cytoplasmic components for lysosomal degradation. In this example, cells used in the assay are from a clonal selection of GFP-transfected HeLa cell line. GFP is tagged to the LC3 autophagy marker. When cells are driven into autophagy process during starvation, granules are produced, recognized and bound by the LC3 marker, and identified as green tiny punctuate spots in the cell cytoplasm. In a normal cell mechanism, the production of granules is detected and the granules are digested by lysosomes. In order to stop this degradation and thereby allow a count of the intracellular granules, hydroxychloroquine sulfate is added after the drug treatment.

Example 3A: Exemplary Materials/Reagents

| Materials/Reagents | Brand name | Catalog number | Stock concentration | Function | Storage condition |
|---|---|---|---|---|---|
| DropArray™ 384-well cell plate (TC) | Curiox Biosystems | 384-PT-TC-01 | NA | Cell plate | RT |
| HeLa-LC3-GFP | ATCC | CCL-2 | NA | Cell line | LN$_2$ or −80° C. |
| DPBS without Ca$^{2+}$ or Mg$^{2+}$ | | | | Cell culture and cell wash | 4° C. or RT |
| DMEM-high glucose | Sigma-Aldrich | D5648 | 1× | Cell growth medium | 4° C. |
| Heat inactivated FBS | | | 10× | Cell growth medium | −20° C.; when defrosted at 4° C. |
| Penicillin-Streptomycin | | | 100× | Cell growth medium | −20° C.; when defrosted at 4° C. |
| Geneticin, G418 | CalBiochem | 345812 | 5 mg/ml | Cell growth medium | 4° C. |
| Trypsin-EDTA | PAA | L11-004 | 1× | Cell detachment | −20° C.; when defrosted at 4° C. |
| Accumax | Sigma-Aldrich | A7089 | 1× | Cell detachment | −20° C.; when defrosted at 4° C. |
| Earl's Balanced Salt Solution (EBSS) | Sigma-Aldrich | E2888 | 1× | Starvation medium | RT |
| DMSO | Sigma-Aldrich | D8418 | NA | Compound diluent | RT |
| Wortmannin | Sigma-Aldrich | W1628 | 10 mM or 4.28 mg/ml | Positive control | −80° C.; when defrosted at 4° C. |
| Hydroxycholoroquine sulfate | Sigma-Aldrich | H0915 | 10 mM or 4.3 mg/ml | Autophagic flux inhibitor | −20° C. in dark |
| 37% formaldehyde | Merck | 104003 | 37% | Cell fixative | RT in dark |
| ToPro-3 | Invitrogen | T3605 | 1 mM | Cell staining | −20° C.; when defrosted at 4° C. |
| Hoechst 33342 | Invitrogen | H3570 | 16.2 mM or 10 mg/ml | Cell staining | −20° C.; when defrosted at 4° C. |

Example 3B: Exemplary Work Flow Diagram of the Autophagy Assay

Figure 34C:
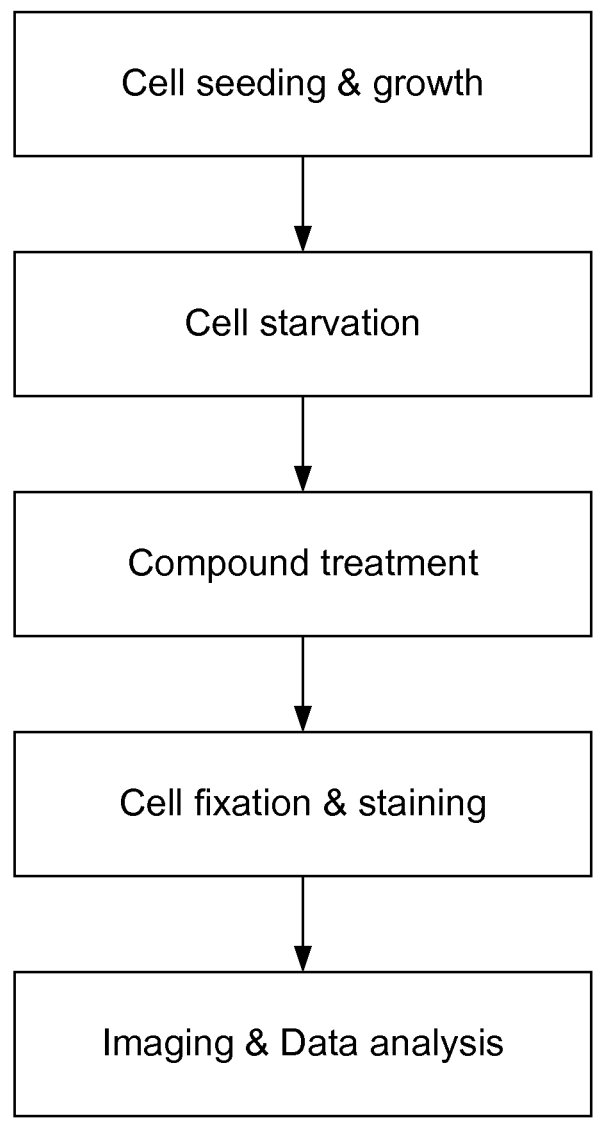
FIG. 34C is an exemplary work flow diagram of autophagy assays.

Please see FIG. 34C.

Example 3C: Exemplary Cell Preparation Procedures

1) HeLa-LC3-GFP cells were grown in D10 growth media (DMEM-high glucose (4.5 g/L) supplemented with 10% fetal calf serum, 5% of penicillin-streptomycin, geneticin 100 m/ml).
2) Trypsinize and seed cells on DropArray™ 384-well cell plate (Catalog #384-PT-TC-01) at density of 600 cells/well/3 µl using Multi-Drop combi at the dispensing speed 3 (fastest speed).
3) Overlay with 15 ml of sterile incubation fluid, dispense gently from the "P24" corner of plate.
4) Incubate cells for 24 hours or overnight at 37° C. in 5% $CO_2$ before compound treatment.

Example 3D: Exemplary Cell Starvation and Compound Treatment Procedures

1) Prepare DMSO-EBSS, Wortmannin and Hydroxychloroquine sulfate (HCQ) at the required working concentration. (Refer Appendix II for details)
2) Aliquot EBSS and all 3 compounds (DMSO-EBSS, Wortmannin and HCQ) into 384 well reservoir microtiter plate.
3) Dummy wash 1× with EBSS using the Curiox HT/LT washing station.
4) Replace incubation fluid with rinsing fluid on DropArray™ plate.
5) Wash 3× with EBSS using the Curiox HT/LT washing station. Add 3 ml of rinsing fluid immediately after wash.
6) Dispense 2 µl of EBSS using Bravo V11 or other automated dispenser (For Bravo v11, dispensing at 0.8 mm height from well bottom, at rate of 0.5 µl per second).
7) Add another 1 ml or top-up to 4 ml in total of rinsing fluid to the plate. Ensure drops were immersed under fluid.
8) Within 5 minutes, add 0.5 µl of Wortmannin of desired final concentration and 0.5 µl of 10 µM of HCQ into the same droplets; using Bravo V11 automated dispenser, at 0.5 mm height from well bottom, at rate of 0.5 µl per second. In conventional 384-well microtiter plate, compound treatment is done by adding 40 µl of EBSS+5 µl of either negative or positive control +5 µl of HCQ as opposed to DropArray plate, in which the volume is adjusted to 2 µl+0.5 µl+0.5 µl, respectively.
9) Adding another 10 ml Rinsing fluid.
10) Incubate cells for 2 hours at 37° C. in 5% $CO_2$.

Example 3E: Exemplary Cell Fixation and Nuclear Staining Procedures

1) Dummy wash 1× with 1×PBS using the Curiox HT/LT washing station.
2) Prepare 4% formaldehyde fresh from 37% stock in 1×PBS, pre-warmed at 37° C. water bath for 15-30 minutes in the dark.
3) Replace incubation fluid with rinsing fluid after compound incubation.
4) Drain rinsing fluid for 5 seconds by holding plate at an angle of more than 120°
5) Flood plate with 25-30 ml of 4% pre-warmed formaldehyde or wash assay plate 3× with 1×PBS and then dispense 2 µl of 4% pre-warmed formaldehyde, followed by top-up rinsing fluid to 10 ml to cover the drops.
6) Incubate at room temperature for 15 minutes
7) Wash assay plate 3× with 1×PBS using the Curiox HT/LT washing station. Add 3 ml of rinsing fluid immediately.
8) Dispense 2 µl of 1 µM ToPro-3 or 4 µM Hoechst 33342 into each well.
9) Top-up rinsing fluid to 10 ml to cover the drops
10) Incubate at room temperature for 15 minutes in dark
11) Wash assay plate 3× with 1×PBS using the Curiox HT/LT washing station. Add 3 ml of rinsing fluid immediately.
12) Dispense 2 µl of 1×PBS into each well.
13) Add 10 ml of rinsing fluid.
14) Seal plate with aluminum seal.
15) Follow appropriate scanning procedure compatible to the corresponding imager.
16) Store plate at 4° C. if plate is not sent for scanning immediately.

Example 3F: Preparation of Reagents and Compounds

Those of skill in the art will appreciate that, for automation, every piece of automation instrumentation has a non-recoverable dead volume associated with it. As such, dead volumes, priming volumes and rinsing volumes should be accounted for when calculating reagent requirements.
DMSO-EBSS
 Prepare fresh
 NEGATIVE CONTROL is at 0.3% DMSO final concentration
 Dilute 100% DMSO to 1.8% DMSO in EBSS (xxx)
 Add 25 µl into each well of a 384-well reservoir microtiter plate
Wortmannin
 Stock Wortmannin (10 mM or 4.28 mg/ml) is resuspended in 100% DMSO, and kept at −80° C. in multiple aliquots.
 Fresh tube of aliquots requires 5 minutes of sonication
 After the first dilution into aqueous solution i.e. EBSS, it is also recommended to sonicate it for 5 minutes
 Vortexing is sufficient for subsequent dilution
 POSITIVE CONTROL is at 33 nM final concentration.
 Dilute 1/100 (xxx) then 1/100 (xxx) to make 198 nM
 Add 25 µl into each well of a 384-well reservoir microtiter plate HCQ
 Stock HCQ (10 mM or 4.3 mg/ml) is resuspended in sterile $H_2O$, and kept at −20° C. in multiple aliquots.
 Dilute HCQ in EBSS
 Working concentration of HCQ is at 100 4 final concentration
 Dilute 1/100 (xxx) in EBSS to make 600 4
 Add 25 µl into each well of a 384-well reservoir microtiter plate Example 4: Mitotic Index Assay This assay protocol demonstrates the benefits provided by the gentle wash mechanism of the DropArray platform described herein. Though a commonly run assay, the mitotic index assay is difficult to run in a high-throughput manner due to extensive cell loss from the washing steps for various cell lines in mitotic phase. DropArray platform could perform the washing steps with minimal cell loss for loosely attached cells, including semi-adherent and suspension cells.

Mitotic index is a valuable means of characterizing cell proliferation, and represents the cell fraction within a population which is undergoing cellular division. The mitotic index is often higher in cancerous cells because of uncontrolled cell proliferation. Mitotic cells may be visualized using an antibody specific for a phosphorylated core histone protein abundant in the nuclei of dividing cells. Compounds which inhibit mitotic progression, such as nocodazole, vinblastine, colchicine, pactlitaxel, curacin and docetaxel, increase the mitotic index of a cell population.

In this example, docetaxel is used as the agonist for blocking mitotic progression. Therefore, in the positive control wells (i.e. docetaxel treated cells), a higher mitotic index can be observed than in the negative control wells (i.e. untreated cells)

Example 4A: Exemplary Materials/Reagents

| Materials/Reagents | Brand name | Catalog number | Stock concentration | Function | Storage condition |
|---|---|---|---|---|---|
| DropArray™ 384-well cell plate (TC) | Curiox Biosystems | 384-PT-TC-01 | NA | Cell plate | RT |
| HeLa cells | ATCC | | | Cell line | $LN_2$ or −80° C. |
| DPBS without $Ca^{2+}$ or $Mg^{2+}$ | | | | Cell culture and cell wash | 4° C. or RT |
| DMEM-high glucose | Sigma-Aldrich | D5648 | 1× | Cell growth medium | 4° C. |
| Heat inactivated FBS | PAA | | 10× | Cell growth medium | −20° C.; when defrosted at 4° C. |
| Penicillin-Streptomycin | | | 100× | Cell growth medium | −20° C.; when defrosted at 4° C. |
| Trypsin-EDTA | PAA | L11-004 | 1× | Cell detachment | −20° C.; when defrosted at 4° C. |
| DMSO | Sigma-Aldrich | D8418 | NA | Compound diluent | RT |
| Docetaxel | Sigma-Aldrich | 01885 | 5 mg/ml | Positive control | −20° C.; when defrosted at 4° C. |
| 37% formaldehyde | Merck | 104003 | 37% | Cell fixative | RT in dark |

Example 4B: Exemplary Work Flow Diagram for Mitotic Index Assay

Figure 34D:
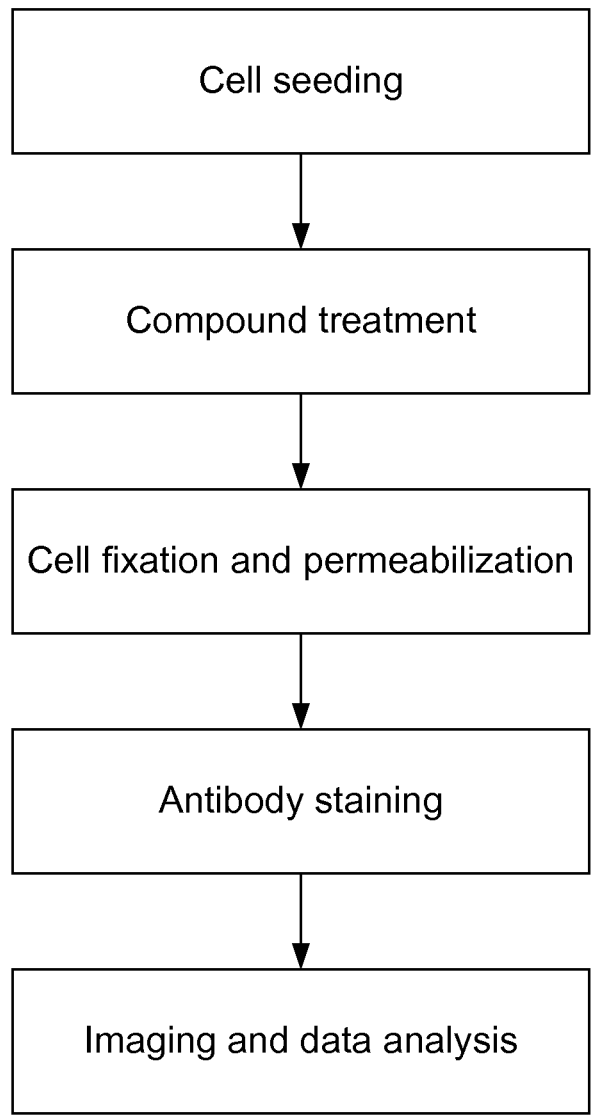
FIG. 34D is an exemplary work flow diagram for mitotic index assays.

Please see FIG. 34D.

Example 4C: Exemplary Procedures for Cell Preparation and Compound Treatment 1. HeLa-LC3-GFP cells were grown in D10 growth media (DMEM-high glucose (4.5 g/L) supplemented with 10% fetal calf serum, 5% of penicillin-streptomycin.)
2. Prepare Docetaxel at the required working concentration in D10 media.
3. Trypsinize and seed cells on DropArray™ 384-well cell plate (Catalog #384-PT-TC-01) at density of 1200 cells/well/30 media containing Docetaxel using Multi-Drop combi at the dispensing speed 3 (fastest speed).
4. Overlay with 15 ml of sterile incubation fluid, dispense gently from the "P24" corner of plate.
5. Incubate cells for 24 hours or overnight at 37° C. in 5% $CO_2$.

Example 4D: Exemplary Procedures for Cell Fixation

1. Dummy wash 1× with 1×PBS using the Curiox HT/LT washing station.
2. Prepare 4% formaldehyde fresh from 37% stock in 1×PBS, pre-warmed at 37° C. water bath for 15-30 minutes in the dark.
3. Replace incubation fluid with rinsing fluid for the cell plate.
4. Drain rinsing fluid for 5 seconds by holding plate at an angle of more than 120°
5. Flood plate with 25-30 ml of 4% pre-warmed formaldehyde. OR wash assay plate 3× with 1×PBS and then dispense 2 µl of 4% pre-warmed formaldehyde, then top-up rinsing fluid to 10 ml to cover the drops
6. Incubate at RT for 15 minutes
7. Wash assay plate 3× with 1×PBS using the Curiox HT/LT washing station. Add 3 ml of rinsing fluid immediately.

Example 4E: Exemplary Procedures for Cell Permeabilization

1. Dispense 2 µl of 1× permeabilization buffer into each well.
2. Top-up rinsing fluid to 10 ml to cover the drops.
3. Incubate at RT for 15 minutes.
4. Wash assay plate 2× with 1×PBS using the Curiox HT HT/LT washing station. After wash, add 3 ml of rinsing fluid immediately.

Example 4F: Exemplary Procedures for Antibody and Nuclear Staining

1. Dispense 2 µl of diluted primary antibody into each well.
2. Top-up rinsing fluid to 10 ml to cover the drops.
3. Incubate at room temperature for 1 hour.
4. Wash assay plate 2× with 1×DPBS using the HT Curiox HT/LT washing station. After wash, add 3 ml of rinsing fluid immediately.
5. Dispense 2 µl of diluted secondary antibody & Hoechst 33342 nuclear stain into each well.
6. Top-up rinsing fluid to 10 ml to cover the drops.

7. Incubate at room temperature for 1 hour in dark.
8. Wash assay plate 2× with 1×DPBS using the HT Curiox HT/LT washing station. After wash, add 3 ml of rinsing fluid immediately.
9. Seal plate with aluminum seals.
10. Follow appropriate scanning procedure compatible to the corresponding imager.
11. Store plate at 4° C. f plate is not sent for scanning immediately.

Example 5: IPS Derived Cardiomyocytes on DropArray™ Plate

IPS derived cardiomyocytes are more prevalently used in various types of assays. However, the cost of these cells has prohibited their broad use in drug discovery or tests. The DropArray™ platform permits dramatically reduced quantities of cell and reagents to be used with minimal cell loss during washing. This protocol describes the culture of IPS derived cardiomyocytes using DropArray™ 384 well plate with PDL coatings, and their use in a FLIPR assay.

Example 5A: Exemplary Work Flow Diagram

Figure 34E:
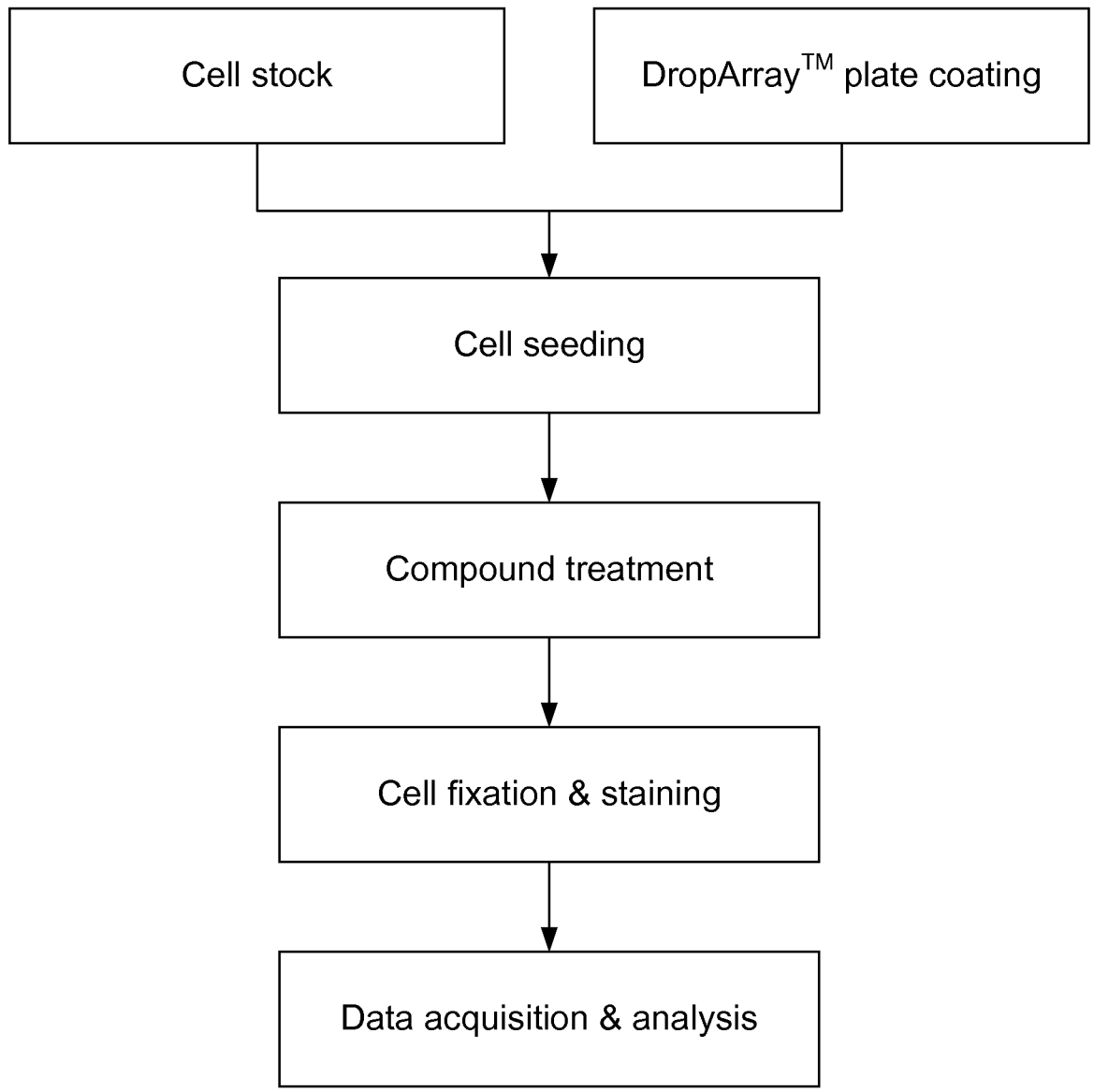
FIG. 34E is an exemplary work flow diagram for cardiomyocyte assays.

Please see FIG. 34E.

Example 5B: Exemplary Procedures for PDL Coating

1) Prepare PDL Coating solution. Dissolve 5 mg poly-D-lysine (Sigma # P6407 5 mg) in 50 ml COLD 0.1M Borate Buffer, pH 8.5.
2) Rocking for 1 hour at room temperature to dissolve.
3) Filter with 0.2 micron filter to sterilize.
4) Dispense 30 µl/well using automatic dispenser(s).
5) Overlay with 2 ml Rinsing fluid.
6) Incubate the plate with lid for 2 hour at room temperature, or at 37° C. incubator.
7) Wash with 2×ddH$_2$O or medium using Curiox HT washing station or manually.
8) For manual washing, tap out any excess aqueous drops that may be retained on the plate. Aggregation of cells is common if incomplete removal of coating solution.
9) Use the plate immediately, or air dry the plates overnight and store the coated plate at 2-8° C.
The coated plates can be stable for at least two weeks when stored at 2 to 8° C. and kept in an air-tight environment.

Example 5C: Exemplary Procedures for Cell Seeding

1) Thaw the cell stock at 37° C. water bath.
2) Seed cells on coated DropArray™ 384-well cell plate at density of 1200-1500 living cells/well/20 using Multi-Drop combi at the dispensing speed 3 (fastest speed).
3) Overlay with 15 ml of sterile incubation fluid, dispense gently from the "P24" corner of plate.
4) Incubate cells for further treatment.

Example 6: Direct DNA/siRNA Transfection Guide for Drop Array™ 384-Well Plate DNA/siRNA Reverse Transfection is frequently used for functional analysis of multiple genes in parallel. This protocol provides a guide of DNA direct Transfection using DropArray™-based system.

Example 6A: Exemplary Procedures for Cell Preparation

This protocol is optimized for reverse transfection with the HEK 293T cells. Those of skill in the art will appreciate that further optimization of this protocol will be needed with other types of cells.
1) Culture cells in DMEM containing 10% FBS, 50 units/ml penicillin and 50 µg/ml streptomycin.
2) 24 hours before transfection, seed approximately 700 cell/3 µl/well on a DropArray™ 384-well plate (PDL) (Catalog #384-PT-PL-01). (Starting cell density range: 500-1000 cells/well for DropArray™ 384-well-plate). Or 2100 cell/8 µl/well on a DropArray™ 96-well plate (PDL) (Catalog #96-PT-PL-01).
3) Overlay with 14 ml of Incubation fluid and incubate at 37° C. overnight.

Example 6B: Exemplary Procedures for Transfection

1) Bring all reagents to room temperature.
2) Prepare transfection mixture:
   A) 2 µg DNA in 100 µl OPTI-MEM (GIBCO) medium
   B) 6 µl Lipofectamine (GIBCO) in 100 µl OPTI-MEM medium
   Mix two solutions gently and incubate at room temperature for 30 min to form the DNA-Liposome complex. Mix the DNA-Liposome complexes with 0.8 ml OPTI-MEM
3) Exchange Incubation fluid with Rinsing fluid on seeded DropArray™ plate.
4) Wash the plate using Curiox HT/LT washing machine with 1×PBS. Overlay with 2 ml of Rinsing fluid.
5) Add transfection mixture at 2 µl/well on a DropArray™ 384-well plate (8 µl/well on a DropArray™ 96-well plate).
6) Incubate cells for 6 hours at 37° C. and 5% CO$_2$ incubator.
7) Wash the plate using Curiox HT/LT washing machine with 1×PBS. Overlay with 2 ml of Rinsing fluid.
8) Dispense fresh medium at 3 µl/well on a DropArray™ 384-well plate (12 µl/well on a DropArray™ 96-well plate.)
9) Overlay with 14 ml Incubation fluid and incubate at 37° C.
10) At desired time, perform image acquisition and data analysis.

Figure 8:
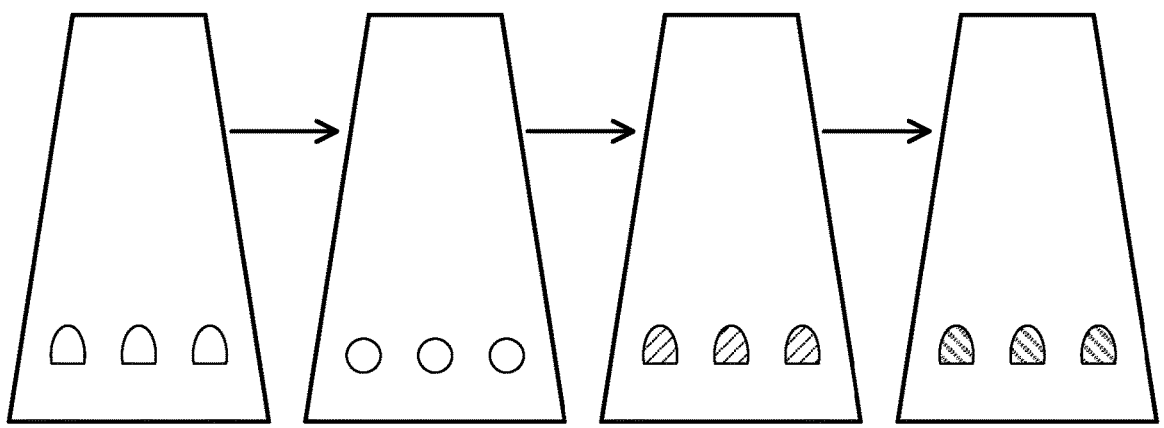
FIG. 8 depicts the steps in an exemplary method of generating reverse transfected cell microarrays as described in Example 7. Plasmid DNA dissolved in an aqueous gelatin solution is dispensed on a DropArray™ plate. The plate is dried and covered with a lipid-based transfection reagent. Cells are then prepared in medium and added directly unto the transfection mix. The transfected cell microarray forms in 1-2 days and is then ready for downstream assays. The method illustrated is the "gelatin-DNA" method of the reverse transfection approach.
Figure 9:
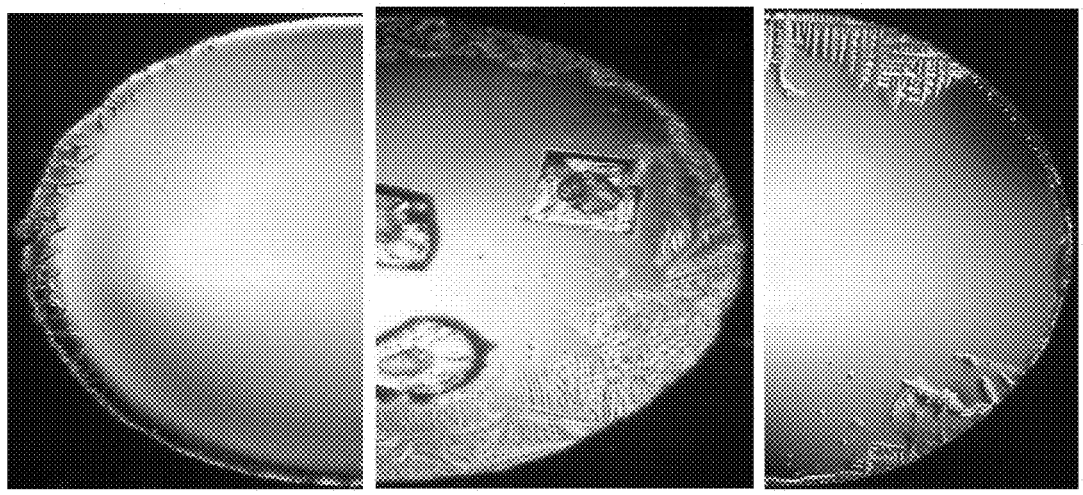
FIG. 9 shows microscopic images of (A) dried DNA-Gelatin, (B) DNA-PBS, and (C) DNA-Water on a DropArray™ plate prepared according to the procedures of Example 7.
Figure 10:
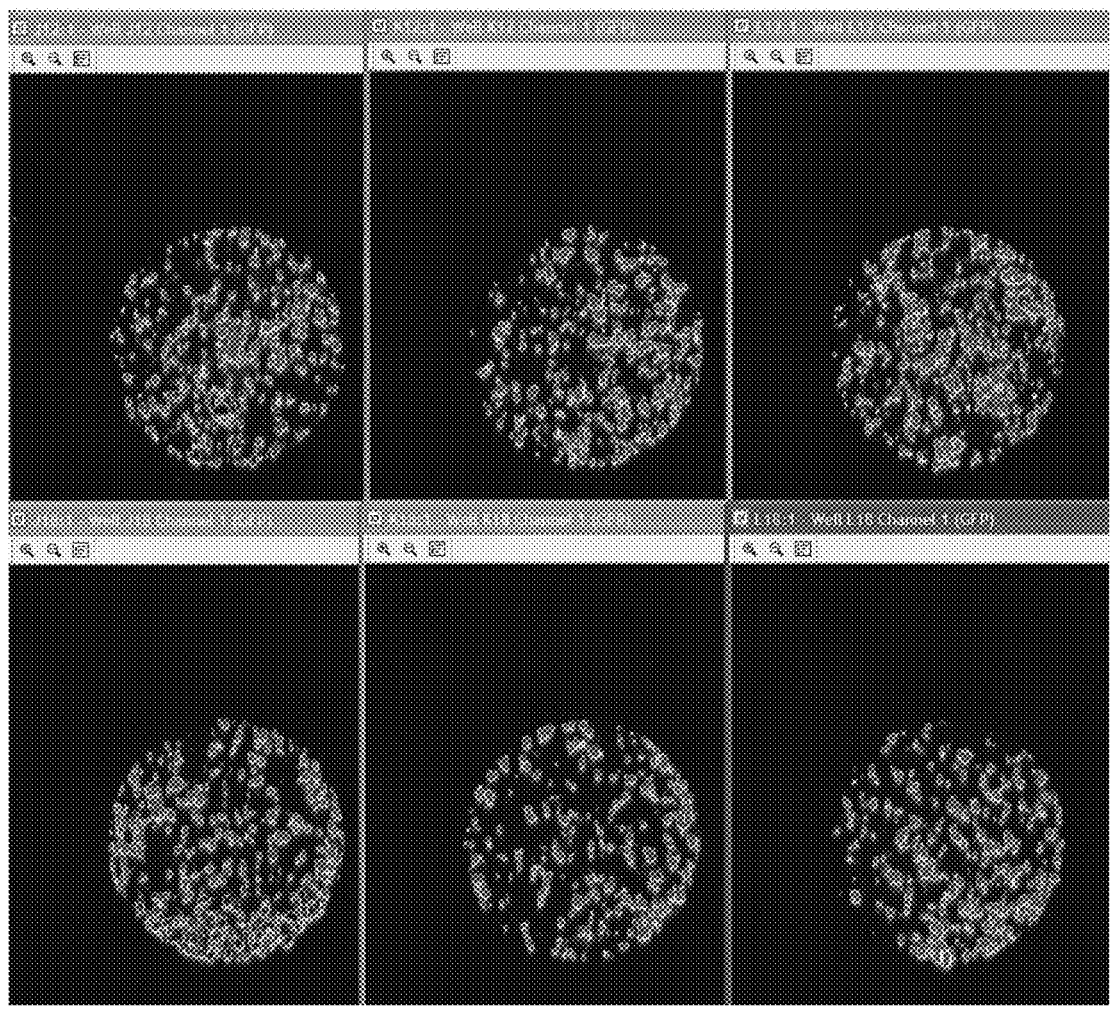
FIG. 10 shows images of cells in six different wells of a DropArray™ plate for a transfection assay performed with Fugene® 6 reagents and GFP-encoding DNA according to the procedures of Example 7E. The images demonstrate >80% transfection efficiency condition of 550,000 cells/ml with DNA concentration of 24 ng/well. Images were generated using IsoCyte™ (Blueshift Biotechnologies).
Figure 12A:
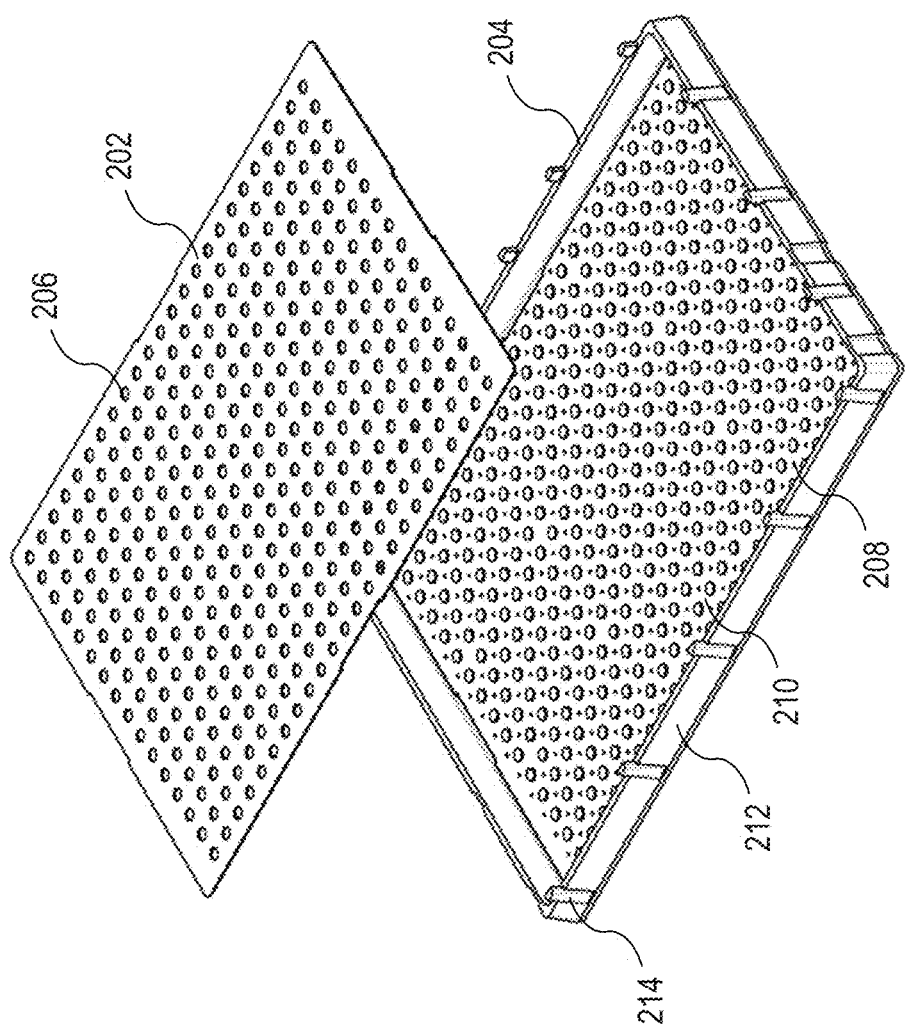
FIG. 12A is an exploded view of an exemplary combination of a first structure and a second structure in accordance with some embodiments.
Figure 12B:
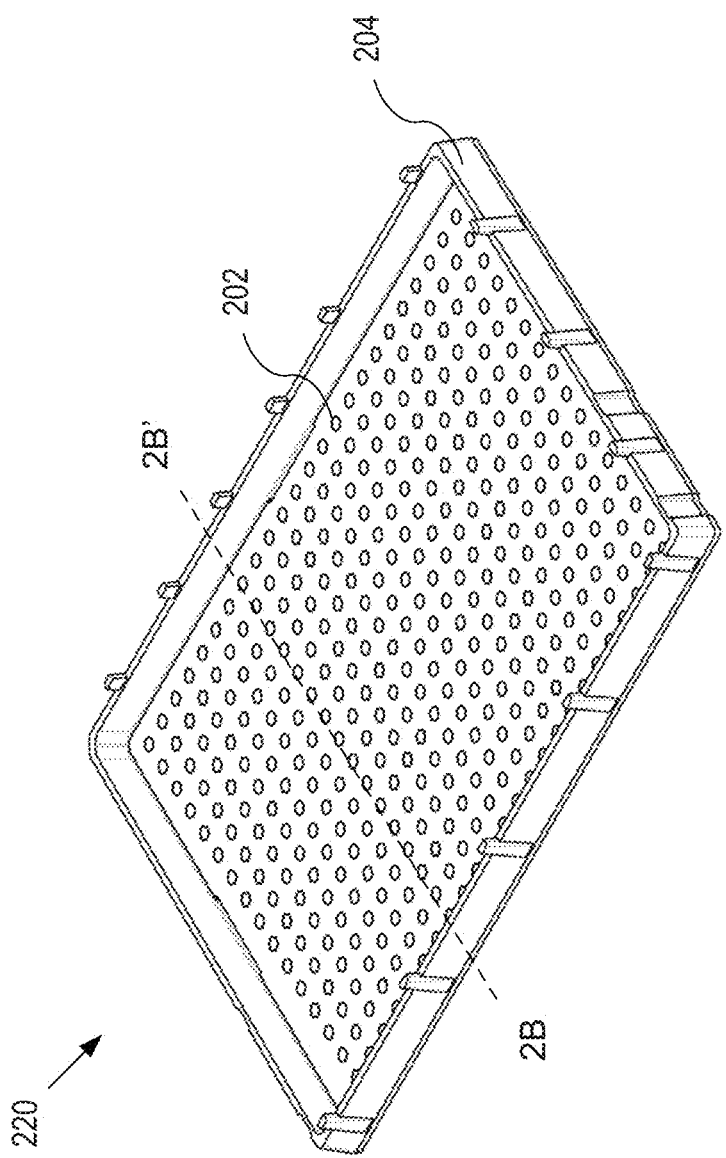
FIG. 12B is a perspective view of the exemplary combination of the first structure and the second structure in accordance with some embodiments.
Figure 12C:
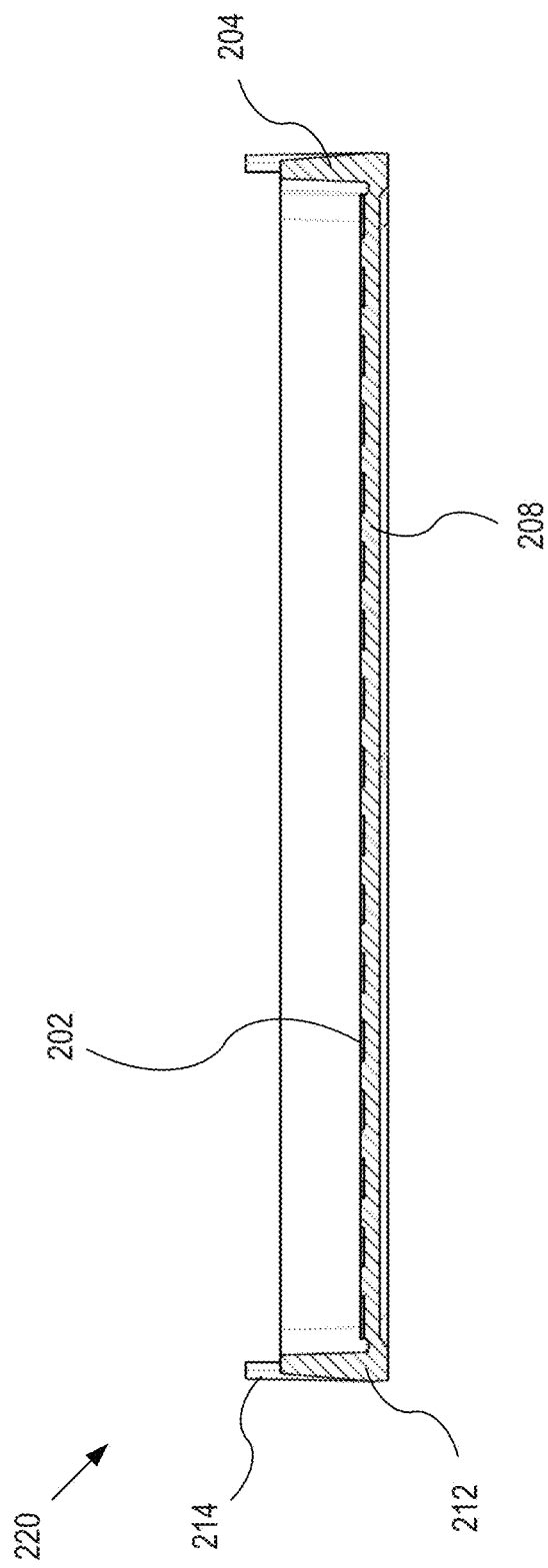
FIG. 12C is a cross-sectional view of the exemplary combination of the first structure and the second structure in accordance with some embodiments.
Figure 12D:
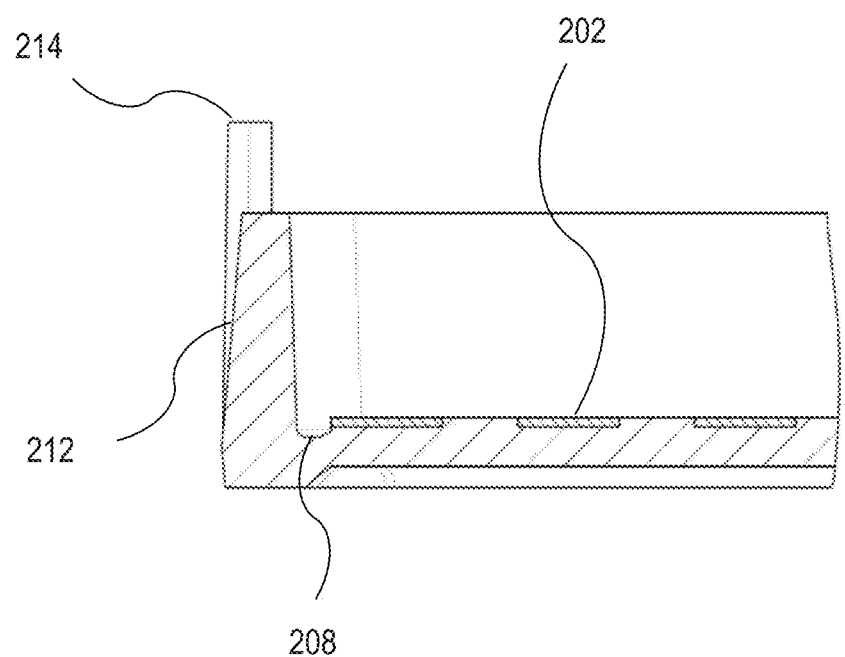
FIG. 12D is a partial sectional view of the exemplary combination illustrated in FIG. 13C in accordance with some embodiments.
Figure 12E:
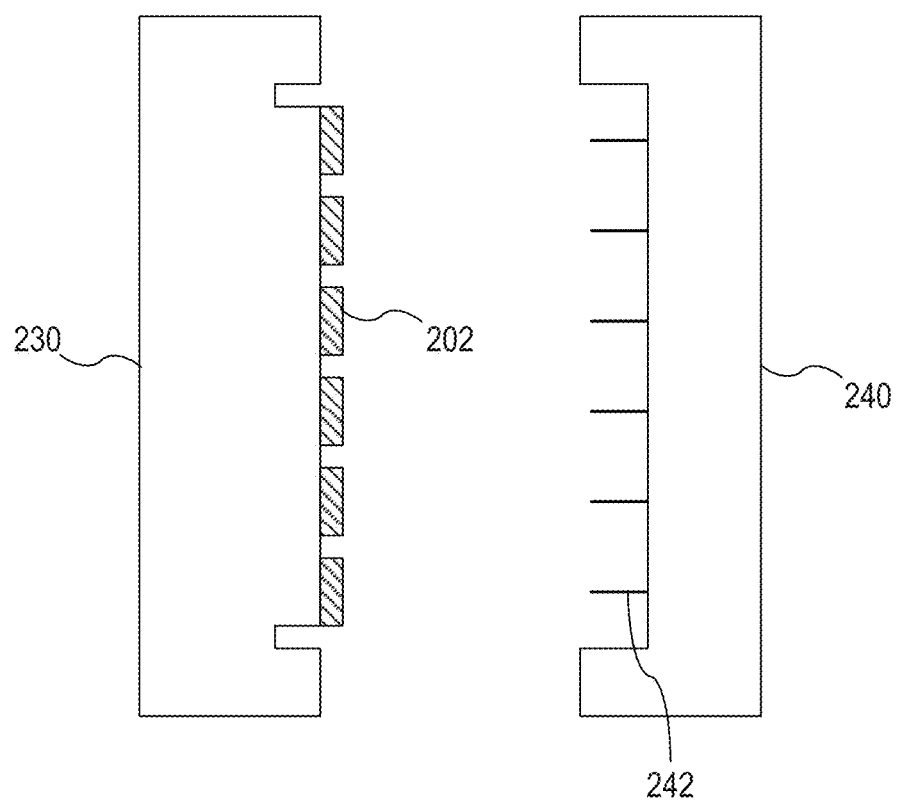
FIGS. 12E-12H are schematic diagrams illustrating selected steps for manufacturing an exemplary combination of a first structure and a second structure in accordance with some embodiments.
Figure 12F:
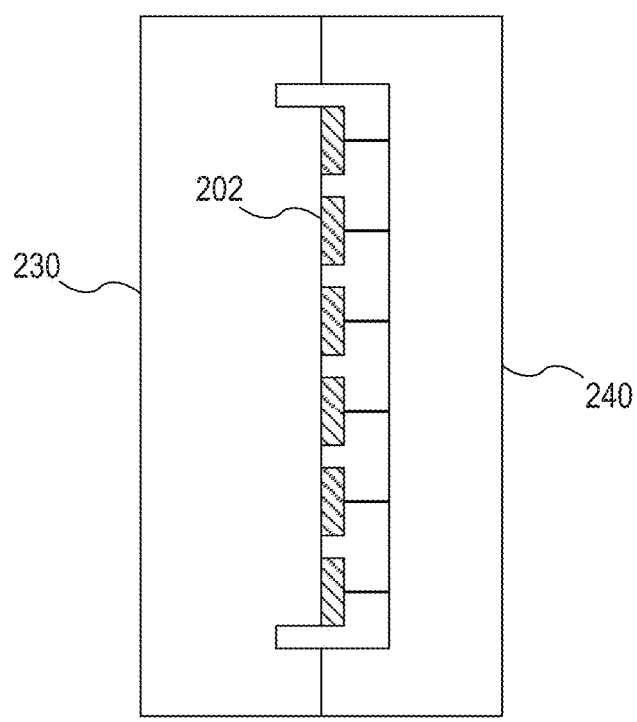
Figure 12G:
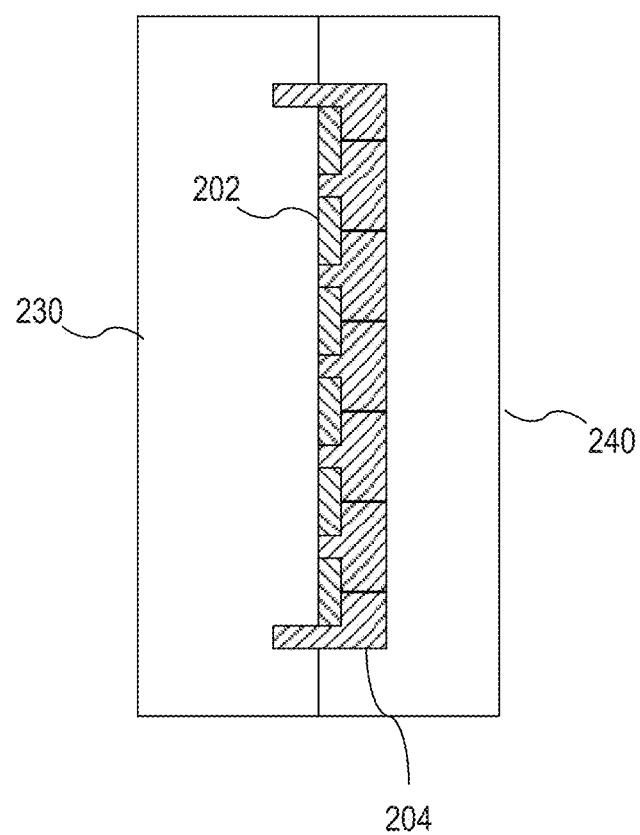
Figure 12H:
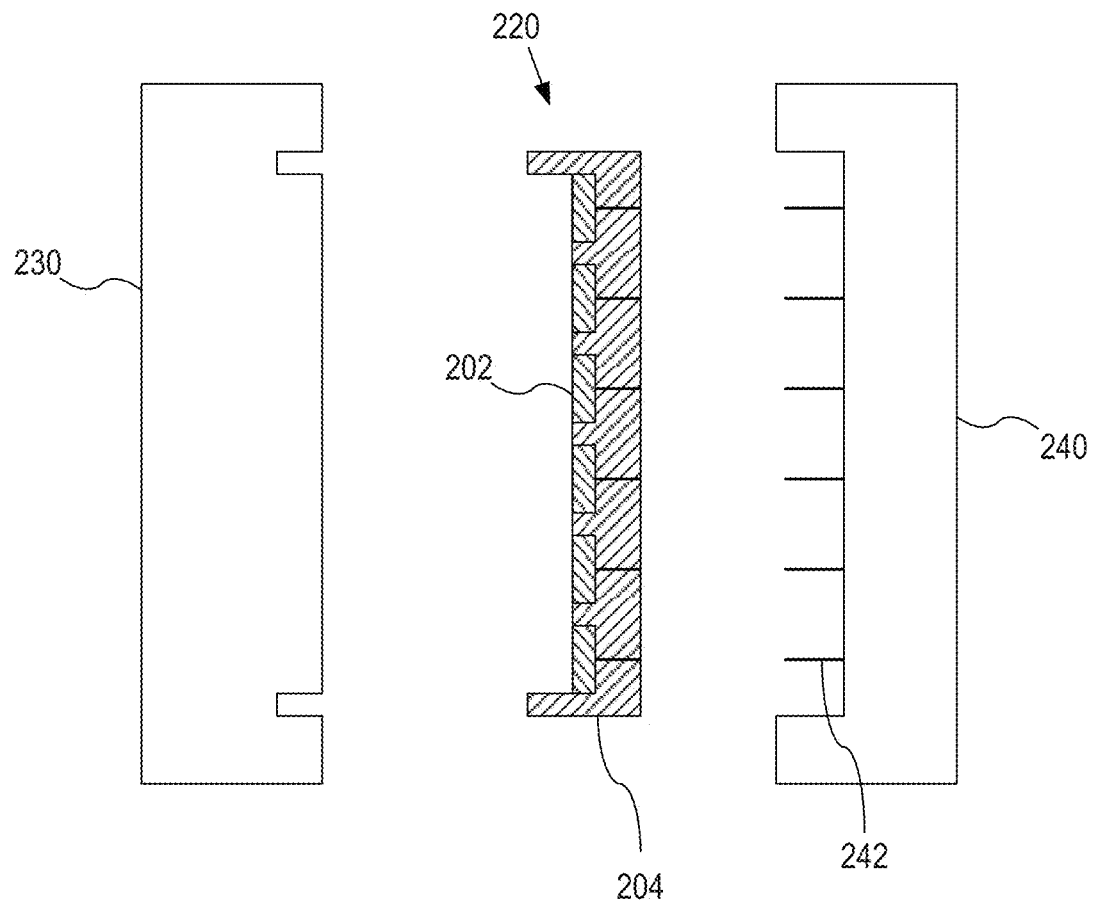

Example 7: Reverse DNA/siRNA Transfection Guide for Drop Array™ 384-Well Plate DNA/siRNA Reverse Transfection is frequently used for functional analysis of multiple genes in parallel. This protocol provides a guide of DNA Reverse Transfection using the DropArray™-based system. Cells are cultured on a DropArray™ plate printed in defined locations with solutions containing different DNAs. Cells growing on the printed areas then take up the DNA, creating spots of localized transfection (FIG. 8). This DNA reverse transfection can be done with or without gelatin coating. Those of skill in the art will appreciate that this protocol can also be adapted to siRNA reverse transfection.

By printing sets of complementary DNAs (cDNAs) cloned in expression vectors, these "transfected cell microarrays" should be of broad utility for the high-throughput expression cloning of genes, particularly in areas such as signal transduction and drug discovery. The scheme (FIG. 8) depicts the steps of an exemplary method of making transfected cell microarrays. Plasmid DNA dissolved in an aqueous gelatin solution is dispensed on a DropArray™ plate. The plate is dried and covered with a lipid-based transfection reagent. Cells are prepared in medium and added directly unto the transfection mix. The transfected cell microarray forms in 1-2 days and is then ready for downstream assays. The method illustrated is the "gelatin-DNA" method of the reverse transfection approach.

Example 7A: Exemplary Procedures for Gelatin Preparation

1) Dissolve gelatin powder in sterile MilliQ water by gently swirling mixture for 15 minutes in a 60° C. water bath.
2) Cool the 0.2% gelatin solution at room temperature, and, while still warm (~37-40° C.), filter it through a 0.45 μm cellular acetate membrane.

In preferred embodiments, a microwave is not used to dissolve the gelatin in water, so as to reduce variability in the resulting solutions. Gelatin dissolved by heating the gelatin-water mix at 60° C. for 15 minutes in a water bath has been found to give the most consistent results. The temperature of the gelatin should be monitored as gelatin would be more susceptible to degradation and contamination if kept at room temperature. It has been found that gelatin solutions do not deteriorate for at least 1 month when stored at 4° C. Examples of suitable gelatins include those from ICN (cat. #901771) and from Sigma (cat # G-9391).

Example 7B: Exemplary Procedures for DNA-Gelatin Preparation

1) DNA is purified via any method that gives supercoiled plasmid DNA with a 260/280 absorbance ratio greater than 1.7. DNA of equivalent or better quality can be obtained using DNA purification known to those of skill in the art. High purity of DNA is ideal for successful transfection and minimal cell cytotoxicity. In preferred embodiments, DNA with a 260/280 absorbance ratio greater than 1.7 is used. DNA of lower ratios may result in greater cytotoxicity.
2) Purified DNA is then mixed with 0.2% gelatin to a final DNA concentration of 4-25 ug/ml (or in water, for example GFP: 30 ng per well). In preferred embodiments, the final gelatin concentration should be 0.17% or greater.

Example 7C: Exemplary Procedures for DropArray™ Printing

1) Dispense the DNA-Gelatin mixture on to DropArray™ 384 well plate, 2 μl/well; (for DropArray™ 96 well plate, 8 μl/well.)
2) Dry the DNA in reduced light environment and vacuum dessicator.

One hour after printing, the plates are ready to use or, alternatively, can be stored at 4° C. or at room temperature (~20-25° C.) in a vacuum desiccator containing anhydrous calcium sulfate pellets. No detectable deterioration in performance after storage was observed for up to 1 month.

Example 7D: Exemplary Procedures for Cell Preparation

This protocol is optimized for reverse transfection with the HEK 293T cells. Other types of cells need further optimization.

1) Culture cells in DMEM containing 10% FBS, 50 units/ml penicillin and 50 μg/ml streptomycin.
2) 24 hours before needed, plate $10 \times 10^6$ cells in 10 ml media in a 10 cm dish. Alternatively, $5 \times 10^6$ cells can be cultured for 2 days before transfection. In both cases, cells are still actively growing when harvested.
3) Immediately before reverse-transfection, in a tissue culture hood, harvest cells.
4) Aliquot $10 \times 10^6$ cells into a sterile 50 ml conical tube.
   a) Add warmed full medium to bring volume to 25 ml.
   b) Close tube and mix by inverting 3-4 times.

Example 7E: Exemplary Procedures for Reverse Transfection of DropArray™ Plate Printed with Gelatin-DNA 1) In a 1.5 ml micro-centrifuge tube, add 16 μl Enhancer to 150 μl EC Buffer.
2) Mix and incubate for 5 minutes at room temperature.
3) Add 25 μl Transfection Reagent and mix by lightly vortexing for 3-4 seconds.
4) Dispense 1.5 μl/well of Transfection Mix unto pre-dried DNA-gelatin DropArray™ 384 well plate (for DropArray™ 96 well plate, 6 μl/well.)
5) Dispense cells at 1.5 μl/well unto DropArray™ 384 well plate (for DropArray™ 96 well plate, 6 μl/well). Overlay with 14 ml of Incubation Fluid.
6) Incubate the DropArray™ plate in a 37° C., 5% $CO_2$ humidified incubator for ~40 hours.
7) Image acquisition and data analysis.

Example 8: Suspension Cell on DropArray™ 96-Well Plate

When washing steps are required, cellular assays using suspension cells or loosely attached cells are not easy to work with. Extra care is required to retain the cells on plates. More often, it is not possible to perform multiple washes for these cells using conventional nozzle-based washers due to the strong shear force generated. The DropArray™ system provides a much gentle whole-plate based washing that enables these types of assays. This protocol describes typical cellular assays using suspension cells or loosely attached cells on DropArray™ 96 well plate.

Example 8A: Exemplary Work Flow Diagram for Suspension Cell Assays

Figure 34F:
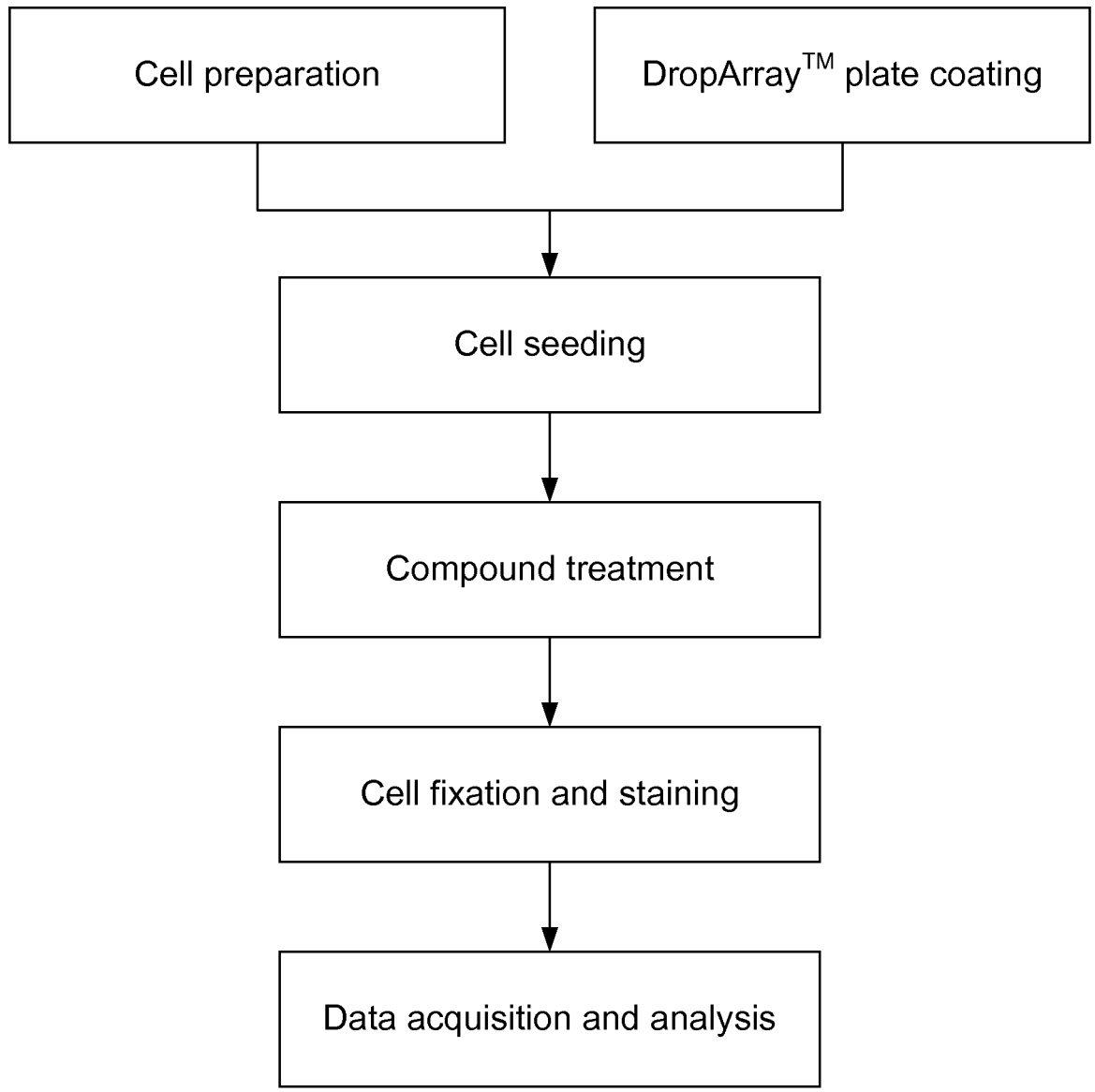
FIG. 34F is an exemplary work flow diagram for suspension cell assays.

Please see FIG. 34F.

Example 8B: Coating Material Preparation

Coating is frequently used for culturing primary and other types of cells. To reduce the assay variations and increase the retention rate, we recommend coat DropArray plate for assays using suspension cells and loosely attached cells. Contact Curiox if coating-ready plates are preferred.

Different types of cells or cell lines prefer different coatings. The below is the general guideline for various coatings. Optimal conditions for attachment must be determined for each cell line and application.

In general, coating DropArray plate is similar to coating regular microtiter plate, except that the amount of coating should be adjusted based on the surface area of DropArray™ 96 well plate (diameter 3.5 mm).

Collagen:

Collagen Type I
  Add collagen to 0.1 M acetic acid to obtain 1 mg/ml collagen solution. Stir at room temperature 1-3 hours until dissolved. Then dilute collagen solution to obtain a working concentration of 50-100 µg/ml.

Collagen Type II and IV
  Collagen Types II and IV may be reconstituted to concentration of 0.5-2.0 mg/ml in 0.25% acetic acid. Dissolve for several hours at 2-8° C., occasionally swirling.

Gelatin:
  3) Dissolve gelatin powder in sterile MilliQ water (0.1%) by gently swirling mixture for 15 minutes in a 60° C. water bath. In some embodiments, a microwave is not used to dissolve gelatin in water as the resulting solutions may vary widely in behavior.
  4) Cool the gelatin solution at room temperature, and, while still warm (~37-40° C.), filter it through a 0.45 µm cellular acetate membrane (CA). The gelatin solutions do not deteriorate for at least 1 month when stored at 4° C. When ready for coating, warm for 30 minutes in a 40° C. water bath.

PDL
  4) Prepare PDL Coating solution.
    Dissolve 5 mg poly-D-lysine (Sigma # P6407 5 mg) in 50 ml COLD 0.1M Borate Buffer, pH 8.5.
  5) Rocking for 1 hour at room temperature to dissolve.
  6) Filter with 0.2 micron filter to sterilize.

PDL/Laminin
  5) Prepare coating solution
    a. 5 mg poly-D-lysine (Sigma # P6407 5 mg)
    b. 50 ml COLD 0.1M Borate Buffer, pH 8.5
    c. Natural Mouse Laminin (Invitrogen #23017-015 1 mg/ml)
  6) Dissolve 5 mg PDL in 50 ml cold 0.1 M Borate buffer. Rocking for 1 hour at room temperature to dissolve.
  7) Filter with 0.2 micron filter to sterilize.
  8) Add 25 µl Laminin into 10 ml PDL-Borate buffer, mix well.

Cell-Tak (BD Catalog No. 354240, 354241):
  1) Prepare 0.1 M sodium bicarbonate, pH8.0. Filter-sterilize the buffer.
  2) Calculate the amount of Cell-Tak needed and dilute the stock solution to working concentration 40 µg/ml. (The recommended coating is 3.5 µg/cm$^2$)

Fibronectin:
  1) Calculate the amount of Fibronectin needed.
  2) Dilute the stock solution to working concentration 50 µg/ml in Ca, Mg free PBS or ddH$_2$O.

Example 8C: Exemplary Coating Procedures

1) Dispense 8 µl/well.
2) Overlay with 4 ml Sealing Fluid.
3) Incubate the plate with lid for 1 hour at room temperature, or at 37° C. incubator.
4) Wash with 2×ddH$_2$O or medium using Curiox HT washing station or manually. (Keep in mind that DropArray Washing station provides evenly washing result across the wells and consistent results between plates.)
5) For manual washing, tap out any excess aqueous drops that may be retained on the plate.
6) Use the plate immediately, or air dry the plates overnight and store the coated plate at 2-8° C.

The coated plates can maintain stability for at least two weeks when stored at 2° C. to 8° C. in an air-tight environment. As those of skill in the art would appreciate, care should be taken to avoid drying out of the coated surface. Optionally, dried coated dishes can be sterilized by exposure to UV light in a sterile culture hood or by rinsing with 70% ethanol.

Example 8D: Exemplary Cell Preparation Procedures

1) Prepare primary cells in appropriate medium and cell concentration.
2) Seed cells on coated DropArray™ 96-well cell plate at density of 250-2500 cells/well/10 µl.
3) Overlay with 15 ml of sterile Sealing Fluid, dispense gently from the "H12" corner of plate.
4) Incubate cells for further treatment.

Example 8E: Exemplary Cell Fixation Procedures

1) Dummy wash 1× with 1×PBS using the Curiox HT/LT washing station.
2) Prepare 4% formaldehyde fresh from 37% stock in 1×PBS, pre-warmed at 37° C. water bath for 15-30 minutes in dark.
3) Drain Sealing Fluid for 5 seconds by holding plate more than 120°.
4) Flood plate with 25-30 ml of 4% pre-warmed formaldehyde; or wash assay plate 3× with 1×PBS and then dispense 10 µl of 4% pre-warmed formaldehyde, then top-up Sealing Fluid 5 ml to cover the drops; or simply add 5 µl of 12% pre-warmed formaldehyde
5) Incubate at room temperature for 15 minutes. Alternatively, concentrated fixing solution can be dispensed to the droplet directly.
6) Wash assay plate 3× with 1×PBS using the Curiox HT/LT washing station. Add 3 ml of Sealing Fluid immediately.

Example 8F: Exemplary Cell Permeabilization Procedures

1) Dispense 10 µl of 1× permeabilization buffer into each well.
2) Top-up Sealing Fluid 5 ml to cover the drops.
3) Incubate at room temperature for 15 minutes.
4) Wash assay plate 2× with 1×PBS using the Curiox HT HT/LT washing.

Example 8G: Antibody and Nuclear Staining

1) Dispense 10 µl of diluted primary antibody into each well.
2) Top-up Sealing Fluid 5 ml to cover the drops.
3) Incubate at room temperature for 1 hour.
4) Wash assay plate 2× with 1×DPBS using the HT Curiox HT/LT washing station. After wash, add 3 ml of Sealing Fluid immediately.
5) Dispense 10 µl of diluted secondary antibody & Hoechst 33342 nuclear stain into each well.
6) Top-up Sealing Fluid 5 ml to cover the drops.
7) Incubate at room temperature for 1 hour in dark.
8) Wash assay plate 2× with 1×DPBS using the HT Curiox HT/LT washing station. After wash, add 5 ml of Sealing Fluid immediately.
9) Seal plate with aluminum seals.

10) Follow appropriate scanning procedure compatible to the corresponding imager.
11) Store plate at 4° C. if plate is not sent for scanning immediately.

Example 9: PBMCs Labeled with MitoTracker Green and Hoechst on Curiox 96 Well Plate

Example 9A: Exemplary Plate Preparation Procedures and Map

A Curiox 96 well plate was divided into quadrants as shown below. CellTak was added per manufacturer's instructions to half of the Curiox plate. The other half was treated with buffer. The plate was incubated for 48 hrs at 4 C. The plate was then washed 3× with PBS.

| No Coating | CellTak |
|---|---|
| 5K cells/well | 5K cells/well |
| No Coating | Cell Tak |
| 10K cells/well | 10K cells/well |

Read 1: Cells reconstituted from frozen stock in media (w/o serum)+labeling reagents; cells kept in suspension for 30 min at 37 C; Cells were then spun down and reconstituted in media (with 10% FBS) and plated at 5K cells/well and 10K cells/well (500K/ml and 1 million cells/ml). Total volume=10 ul. Cells were allowed to settle for 10 min before imaged on IN Cell 2000 at 40×, 1 field/well.

Read 2: The plate was incubated at 37 C for 2 hrs and then washed 3× with PBS (using Curiox platform). Fresh media was then added back to the cells. The plate was re-imaged using the same parameters as Read 1.

Read 3: Following Read 2, the plate was immediately fixed for 20 min with 4% PFA (direct addition of 10 ul of 8% PFA to media drop). The plate was washed 3× using Curiox platform. 10 ul of PBS was added to wells. Plate was imaged using the same parameters as in Reads 1 and 2.

Example 9B: Data and Conclusion

Figure 17D:
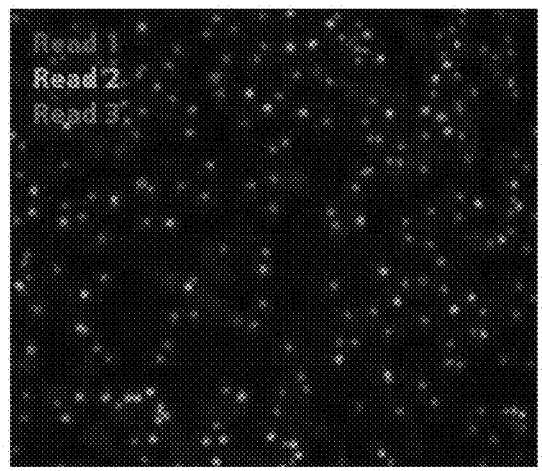
Figure 18A:
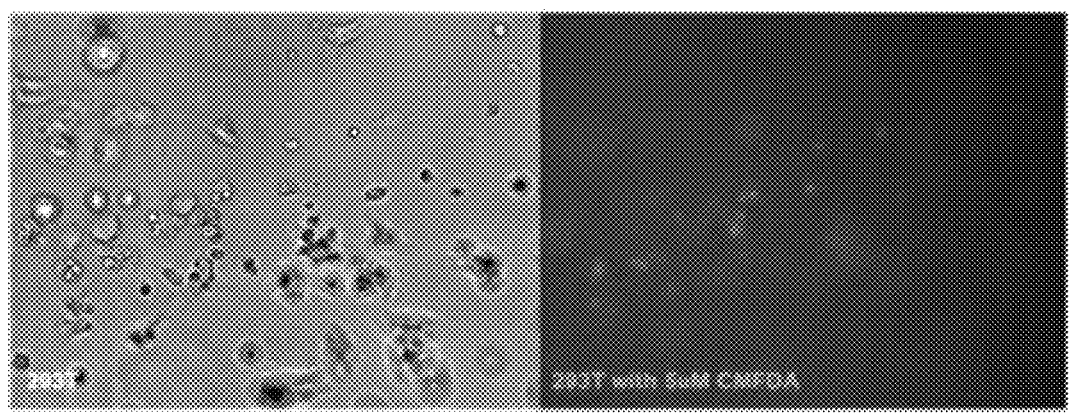
FIG. 18A provides live cell images of HEK293T cells after 4 days of incubation on Geltrex™ coated DropArray™ plates according to the thin gel method (non-gelling) described in Example 12. The image in the right panel was produced using CMFDA Green fluorescence microscopy on the GE InCell 2000.
Figure 18B:
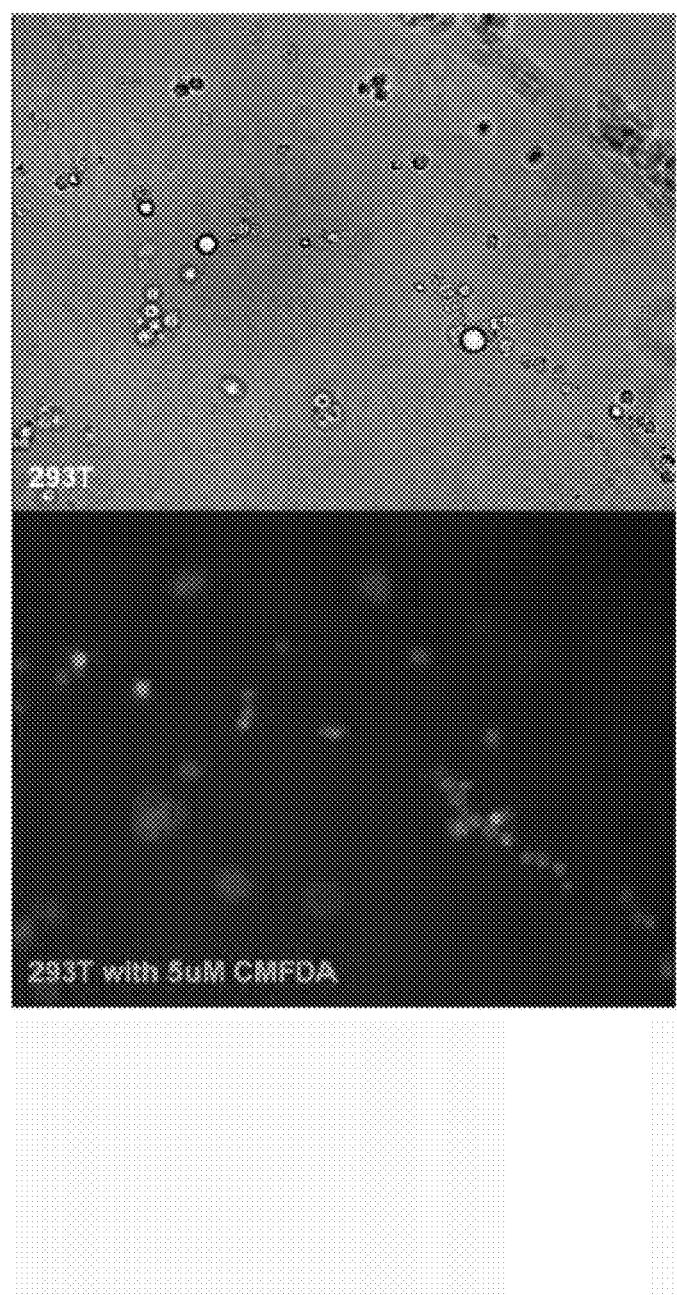
FIG. 18B provides live cell images of HEK293T cells after 4 days of incubation on Geltrex™ coated DropArray™ plates according to the 3-D culture method described in Example 12. The image in the lower panel was produced using CMFDA Green fluorescence microscopy on the GE InCell 2000.

Data obtained for the cell count, MitoTracker Signal, and three sample images from the quadrant having 5K cells/well with CellTak are shown in FIGS. 17A, 17B, and 17C, respectively. FIG. 17D provides the composite image generated by the superimposition of sample images from Read 1, Read 2 and Read 3. As supported by the data, cell loss was minimized in the quadrant having 5K cells/well with Cell-Tak. The MitoTracker signal was also reduced upon fixation but remained robust enough for imaging and analysis. Cells shift was observed between washes.

Example 10: Hepatocyte Toxicity Studies

Hepatocytes are routinely used for toxicity evaluations. However, cost of these cells, especially primary hepatocytes, and detection reagents constrains their broad use in drug discovery or tests. DropArray™ plate provides dramatic reduction of cell and reagents consumption with minimal cell loss during washing. This protocol describes culture of HepG2 hepatocytes using DropArray™ 384 well plate with collagen coating. Various quantitative assays have been tested using the protocol.

Example 10A: Exemplary Work Flow Diagram for the Hepatocyte Study

Figure 34G:
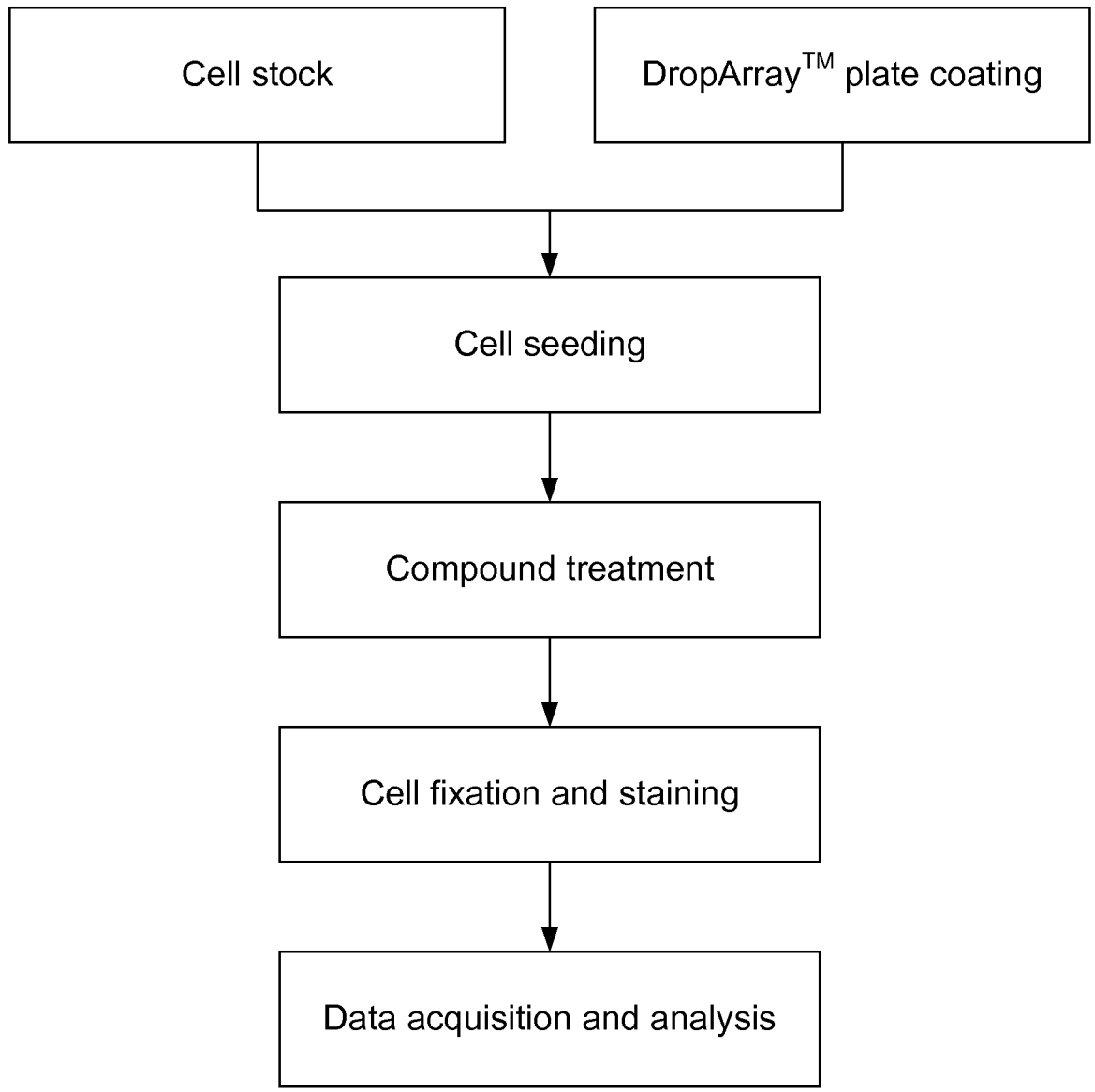
FIG. 34G is an exemplary work flow diagram for hepatocyte studies.

Please see FIG. 34G.

Example 10B: Exemplary Collagen Coating Procedures

1) Prepare Collagen solution.
Add type I collagen to 0.1 M acetic acid to obtain 1 mg/ml collagen solution. Stir at room temperature 1-3 hours until dissovled. Then dilute collagen solution to a working concentration of 50 μg/ml.
2) Filter with 0.2 micron filter to sterilize.
3) Dispense 2 μl/well using automatic dispenser(s).
4) Overlay with 2 ml Sealing Fluid.
5) Incubate the plate with lid for 2 hour at room temperature, or at 37° C. incubator.
6) Wash with 2×ddH$_2$O or medium using Curiox HT washing station or manually. (Keep in mind that DropArray Washing station provides evenly washing result across the wells and consistent results between plates.)
7) For manual washing, tap out any excess aqueous drops that may be retained on the plate.
8) Use the plate immediately, or air dry the plates overnight and store the coated plate at 2-8° C.

The coated plates can maintain stability for at least two weeks when stored at 2° C. to 8° C. in an air-tight environment. As those of skill in the art would appreciate, care should be taken to avoid drying out of the coated surface.

Example 10C: Exemplary Cell Seeding Procedures

1) Prepare hepatocytes in medium with concentration of 600-900 live cells/μl.
2) Seed cells on coated DropArray™ 384-well cell plate at density of 1200-1800 live cells/well/2 μl using automatic dispenser(s).
3) Overlay with 15 ml of sterile Sealing Fluid, dispense gently from the "P24" corner of plate.
4) Incubate cells for 24-48 hrs at 37° C. incubator before further treatment.

Example 11: Medium-Change-Free Long-term Cell Culture on DropArray™ Plate

Frequent medium change is not desirable but necessary in some long-term cell cultures. Researchers sometimes are concerned about sustaining cell growth of DropArray™ 384 well plate small volume (2-3 μl) medium. One of the advantages of the DropArray™ plate is its whole plate-based format. This allows filling the whole plate with 25-30 ml of medium to provide nutrients to sustain cell growth to a very long period of time. This protocol describes culturing cells on DropArray™ 384 well plate with filling the plate with medium and washing procedures to preserve the hydrophobic property of DropArray™ plate. It can be applied to DropArray™ 96 well plate as well.

Example 11A: Exemplary Cell Seeding and Culturing Procedures

1. Dispense 2-3 μl of cells in media to DropArray™ 384-well plate.
2. Overlay with 12 ml of sterile Sealing Fluid (or slightly more if necessary, to ensure the 2-3 μl droplets are covered), dispense by pipetting gently from the "P1" corner of plate, or dispense by Curiox HT washing station.
3. Incubate in a cell culture incubator for 1-24 hours or till the cells settled down on plate.
4. Drain off Sealing Fluid and allow aeration under Culture Hood for 30-60 seconds.
5. Dispense 25 ml (max. holding volume 40 ml) of cell culture media at P1 corner of DropArray™ 384-well plate.
6. Allow long-term incubation (>48 hours).

Example 11B: Exemplary Washing Procedures

1. Take out the cell culture plate from incubator. Drain off cell culture media from the plate.
2. Disable Sealing Fluid Evaporation Time if using Curiox HT washing station.
3. Prime Curiox HT/LT washing station with serum free medium.
4. Wash with 3× serum free medium using Curiox HT/LT washing station.
5. Add 3 ml of Sealing Fluid.
6. Proceed with further steps.

Example 12: Gel Coating on DropArray™ Plates

The surface of the array plates described herein can be coated with basement membrane constituents in some assays. To explain, basement membranes are continuous sheets of specialized extracellular matrix that form an interface between endothelial, epithelial, muscle, or neuronal cells and their adjacent stroma. Basement membranes are degraded and regenerated during development and wound repair. They not only support cells and cell layers, but they also play an essential role in tissue organization that affects cell adhesion, migration, proliferation, and differentiation. Basement membranes provide major barriers to invasion by metastatic tumor cells. Basement Membrane Matrix is a soluble form of basement membrane purified from Engelbreth-Holm-Swarm (EHS) tumor. The extract gels at 37° C. from a reconstituted basement membrane. The major components of the Basement Membrane Matrix include laminin, collagen IV, entactin, and heparin sulfate proteoglycan. Basement Membrane Matrix can be used for promotion and maintenance of a differentiated phenotype in a variety of cell cultures including primary epithelial cells, endothelial cells, and smooth muscle cells. It has been employed in angiogenesis assays, neurite outgrowth assays, and tumor cell invasion assays. This protocol describes the culture of cells using DropArray™ plates with Geltrex™ coating according to the thin gel method and according to the 3-D culture method. The advantage of coating DropArray™ plates with gel is to avoid the meniscus problem, providing a flat and uniform layer of gel for greater ease of cell imaging as compared to gel films formed in conventional microtiter plate wells.

Example 12A: Materials

DropArray™ 384-TC glass plate (Curiox; Cat. #384-GL-TC-01)
DropArray™ 384-TC plastic plate (Curiox; Cat. #384-PT-TC-01)
DropArray™ Incubation Fluid (Curiox; Cat. AN-ST-01-01)
Geltrex™ Reduced Growth Factor Basement Membrane Matrix (without phenol red) (Gibco®; Cat. #12760-013)

Example 12B: Exemplary Procedures for Thin Gel Method (Non-Gelling) on DropArray™

1) Thaw Geltrex™ extract on ice.
2) Mix Geltrex™ by slowly pipetting solution up and down. Avoid creating bubbles.
3) Dilute 1 ml of Geltrex™ into 99 ml of pre-chilled (2 to 8° C.) DMEM/F-12 medium. Empirical determination of the optimal coating concentration of the particular application may be required and the volumes adjusted accordingly.
4) Cover the entire growth surface area (3 to 5 ul for DropArray™ 384-TC plate) with diluted Geltrex™ solution. The coated dish can be stable for at least two weeks when stored at 2° C. to 8° C. in an air-tight environment. As those of skill in the art would appreciate, care should be taken to avoid drying out of the coated surface and to maintain a storage temperature of 2° C. to 8° C. to avoid premature gelling.
5) Incubate coated plates at 37° C. for a minimum of 60 minutes.
6) At time of use, it is recommended to place plates at room temperature for an hour. Immediately place cells in pre-equilibrated cell culture medium.

Example 12C: Exemplary Procedures for 3-D Culture Method on DropArray™

1) Culture cells to establish a stable population at 37° C. in $CO_2$ incubator. Growth media, growth factors, serum requirements, and incubation period may vary by cell type.
2) Thaw Geltrex™ extract on ice.
3) Working on ice, add 2 ul of Geltrex™ to each well in a sterile DropArray™ 384-TC plate. Incubate the plate at 37° C. in the incubator for 30 minutes to promote gelling. The gelling will be reduced to 1 ul gel size.
4) Working on ice, add 0.5 ml of Geltrex™ to 24.5 ml of growth medium (final concentration of 2%) to a sterile container, label container "Assay Medium", and swirl to mix without creating bubbles. Any unused Geltrex™ can be stored at 2° C.-8° C. up to a week or stored in working aliquots at −20° C.
5) Incubate Assay Medium at 37° C. for 30 minutes in preparation for cell dilution.
6) Harvest cells and dilute in Assay Medium. As a general guide, cells are diluted between $5 \times 10^5$ to $7.5 \times 10^5$ cells/ml, depending on cell line and assay conditions. Further optimization may be done by one of skill in the art.
7) Add 2 ul of cell suspension to each well of the DropArray™ 384-TC plate containing Geltrex™. Test compounds (at 1 ul volumes) may also be added at this time.
8) Add 12 ml of Incubation Fluid to overlay above the gelling drops.
9) Incubate plate at 37° C. in humidified $CO_2$ incubator for 4 days.
10) On each day, observe cell growth and structure formation via inverted microscope.
11) On day 4, carefully drain off the Incubation Fluid and leave the plate open for 100 seconds of evaporation. Rinse the plate with 30 ml of medium. Replace with new Assay Medium and 12 ml of Incubation Fluid. Repeat on Day 8 and Day 12.

12) When structures have grown to desired size, prepare cells for analysis, and analyze structures. This step is dependent on cell line and growth conditions.

Example 13: cDNA Transfection Assays with Poorly Adherent Cells

Figures 19A, 19B:
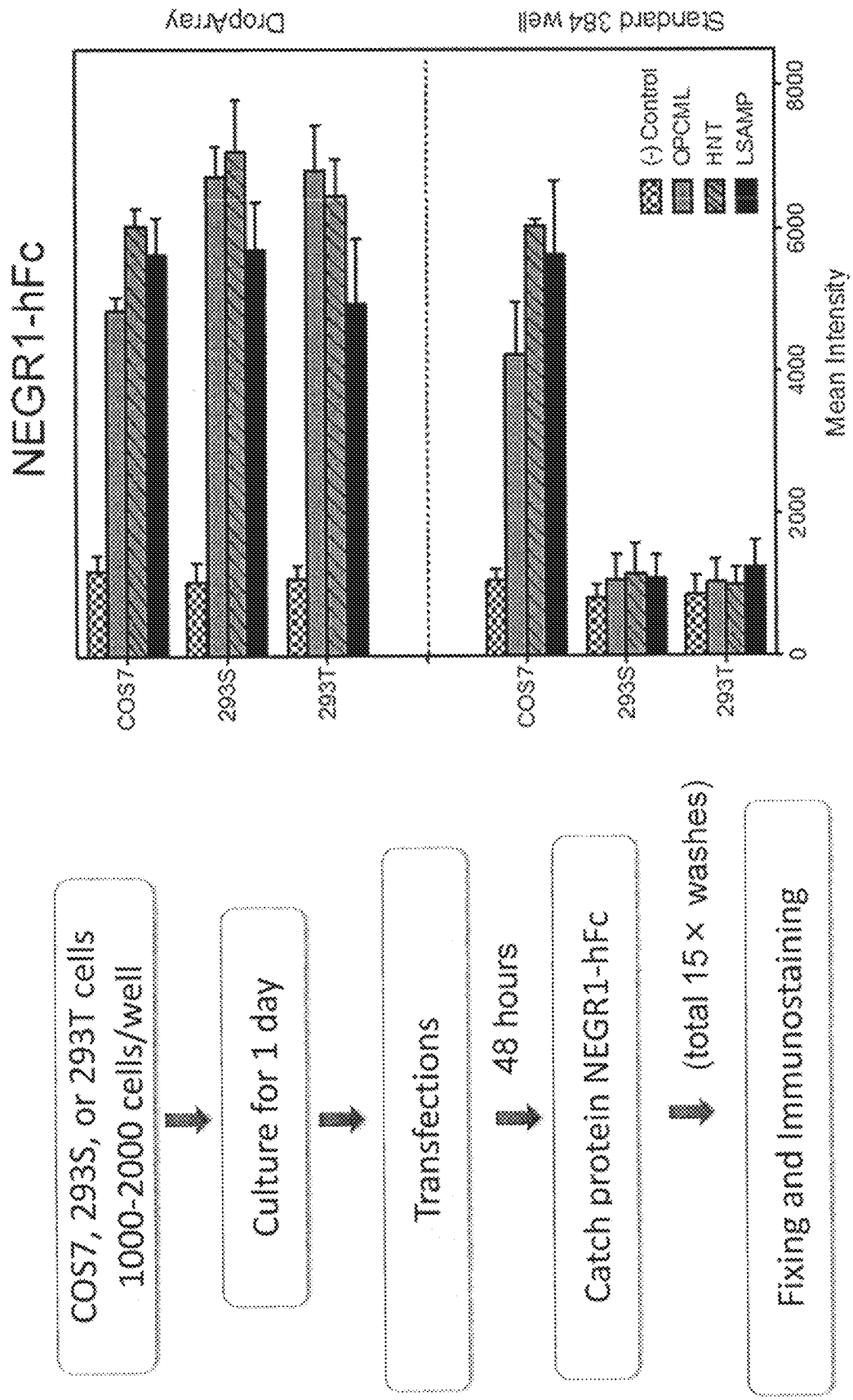
FIG. 19A provides an exemplary work flow diagram of a cDNA transfection assay using adherent (COST), semi-adherent (HEK293T), and suspension (HEK293S) cells. See Example 13.
FIG. 19B shows a comparison of the NEGR1-hFc binding for the respective cell types when the assay is performed on the array plates of the present invention as opposed to conventional 384-well plates.

Using the optimized washing conditions described previously, the DropArray technology was compared to conventional 384 well plate using regular automated washing procedure. Here, COS7 (adherent), HEK293T (semi-adherent) and HEK293S (suspension-adapted) were transiently transfected with LSAMP, HNT or OPCML constructs. See FIG. 19. No change in cell number or density was observed 48 hours after transfection with either of these constructs compared to non-transfected or mock-transfected controls. Cell expressing LSAMP, HNT or OPCML were then incubated with NEGR1-hFc bait protein. Subsequently, NEGR1-hFc binding was detected using an anti human AlexaFluor 488 antibody. As expected, COS7 cells expressing NEGR1 displayed specific binding to LSAMP (data not shown), HNT and OPCML, and binding was similarly detected using either plate format. Quantitation of the fluorescent signal results in at least a five fold increase in mean intensity in response to the specific binding of NEGR1-hFc to LSAMP, HNT or OPCML compared to the non-specific binding observed in non-transfected cells on either plate format. As expected, NEGR1-Fc binding to LSAMP, HNT or OPCML transfected HEK293T or S cells was not detected in conventional 384 well-plate since these semi-adherent and suspension-adapted cells, respectively, are washed out from the well during the washing procedure. However, with DropArray plates and optimized washing conditions, NEGR1-Fc binding to LSAMP, HNT or OPCML transfected HEK293T or S cells was perfectly detectable and the fluorescence mean intensity detected at least equivalent to the ones detected with COS7 cells. This experiment involves 15 cycles of washes. These results clearly demonstrate the ability of DropArray technology to perform multi-step experimental procedures with semi-adherent.

Example 14: Washing Based Assays for PBMCs

Figures 20A, 20B:
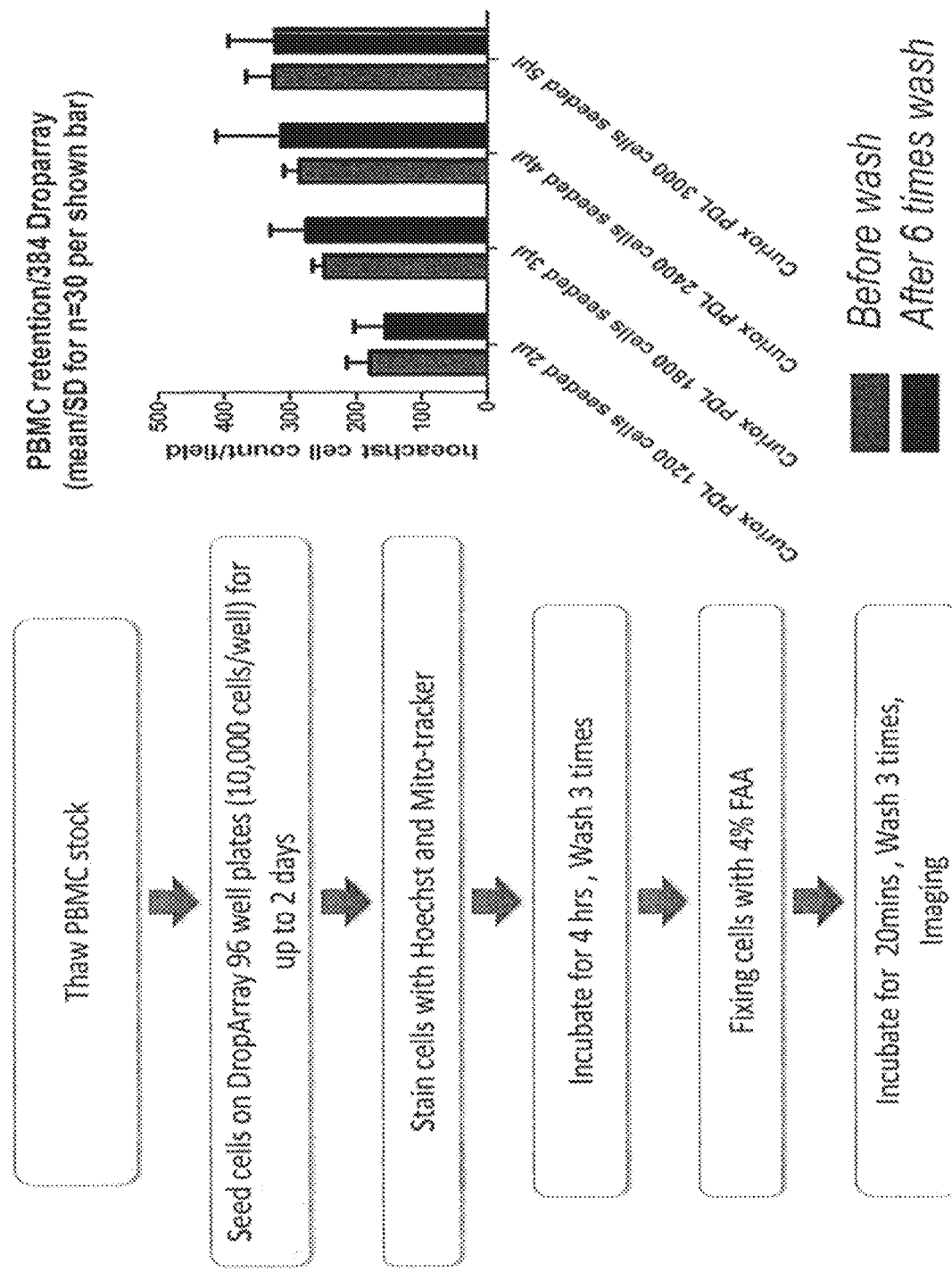
FIG. 20A provides an exemplary work flow diagram of washing-based assays for PBMCs.
FIG. 20B shows the level of PBMC cell retention after 6 washes using an array plate of the present invention (compatible with 384-well format).
Figure 22:
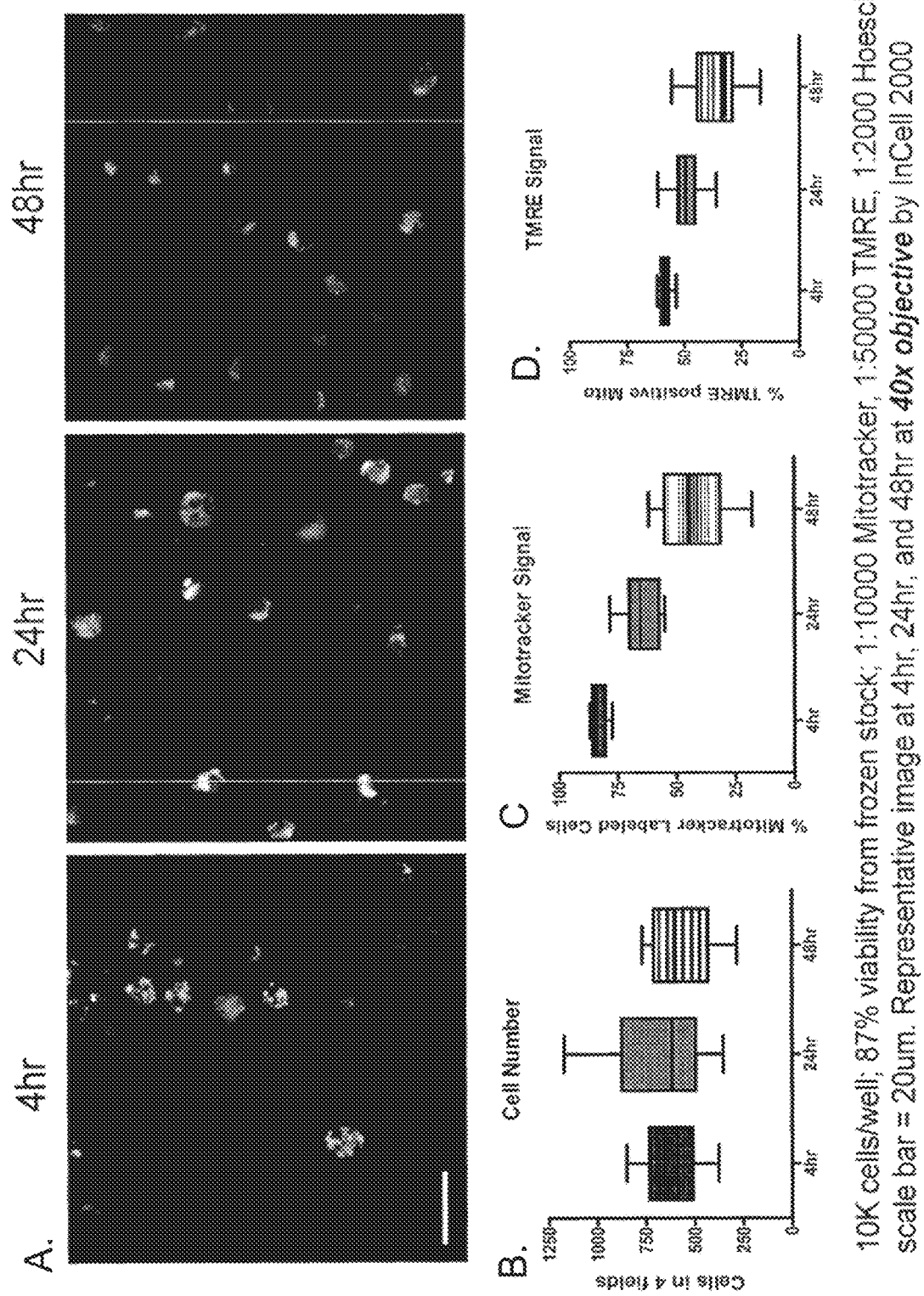
FIG. 22 provides exemplary results using PBMC cells: A provides representative images of PBMC cells at 4 h, 24 h, and 48 h at 40× objective. Data representing the middle 50% (n=32 of 64 wells labeled) of the analyzed data set at the 4 h, 24 h, and 48 h time points is shown in B. C and D provide the % of Mitotracker labeled cells and TMRE positive cells detected respectively at the 4 h, 24 h, and 48 h time points.
Figure 23:
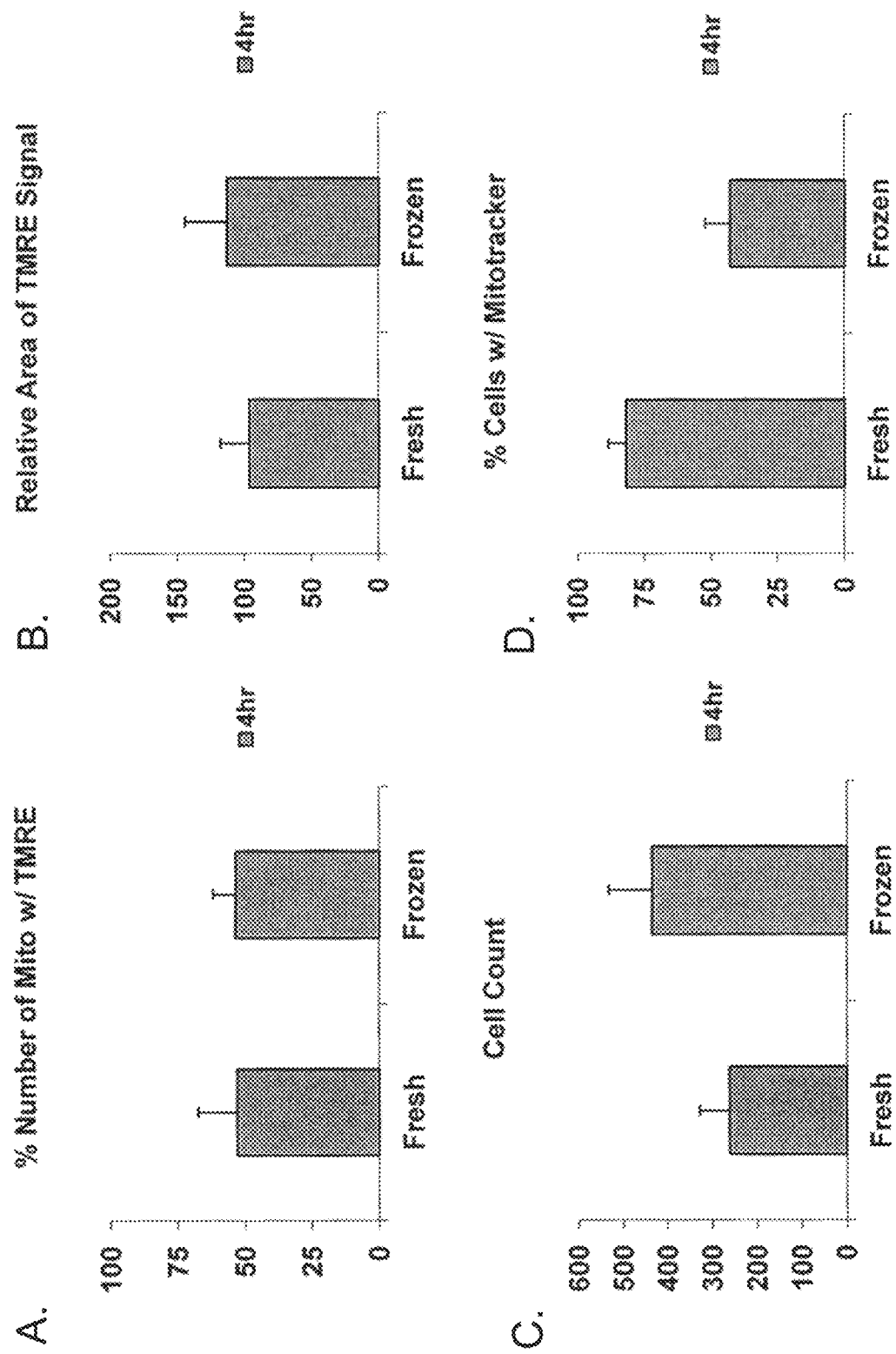
FIG. 23A-D provide a data comparison for fresh and frozen PBMCs at the 4 h time point. Data includes % number of Mito-labeled cells with TMRE signal, relative area of TMRE signal, cell count, and % of cells with Mitotracker signal.

A PBMC compound assay was performed at Harvard medical school, neurodiscovery center, using the array plate technology described herein. The protocol is described in FIG. 20. The suspension cells were found to not anchor to the surface of the array plate. A frozen PBMC experiment was performed and data is provided in FIGS. 21-23. Data in FIG. 22 represent the middle 50% (n=32 of 64 wells labeled) of the analyzed data set determined by Mitotracker green labeling. Hand pipetting into 384 well results in variable liquid dispensing. Mitotracker green was most susceptible to labeling variability; hence, Mitogreen was used to rank the data.

Figure 24:
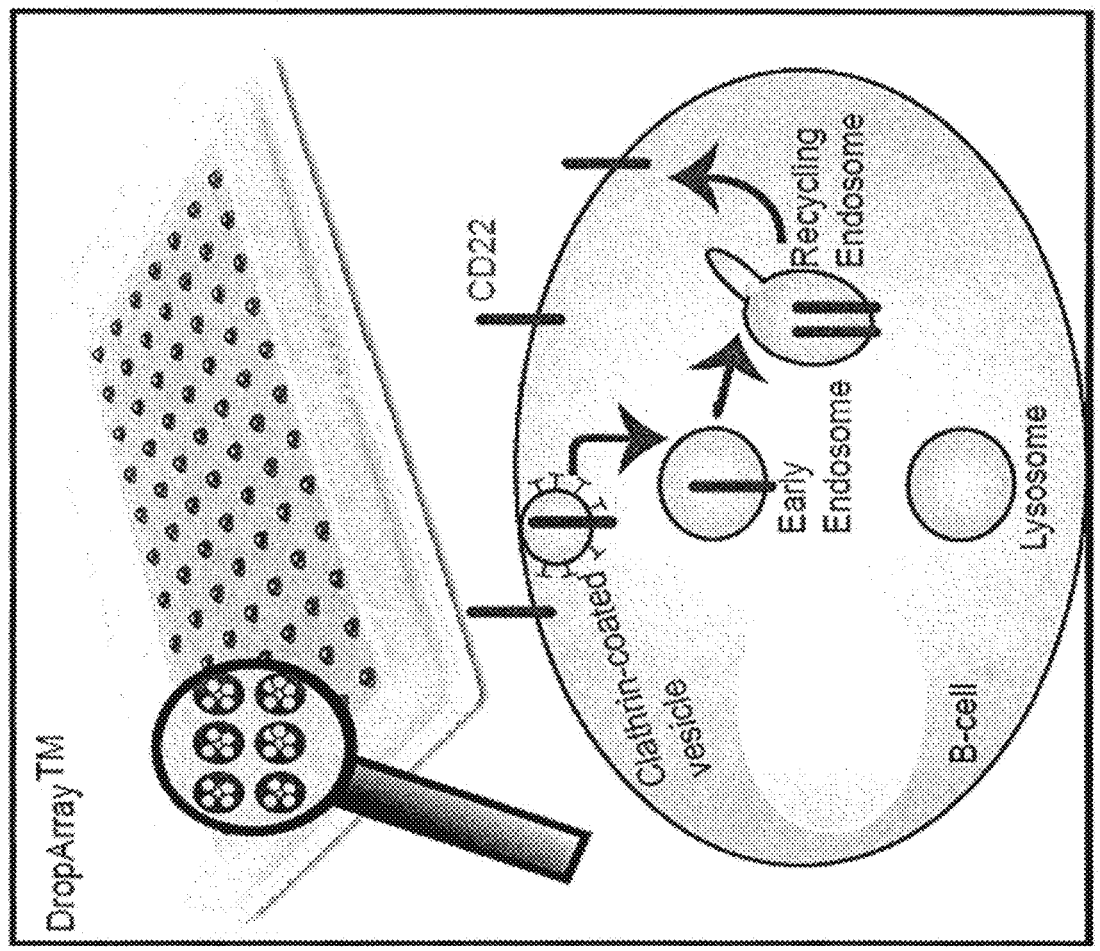
FIG. 24 is a diagram of CD22 antibody trafficking in a B cell. A trafficking and time course study of antibodies in suspension B cells was performed using an array plate of the present invention. The study revealed CD22 antibody trafficking pathway includes internalization in cells after about 5 min and usage of recycling endosome pathway and limited lysosomal pathway.
Figure 25:
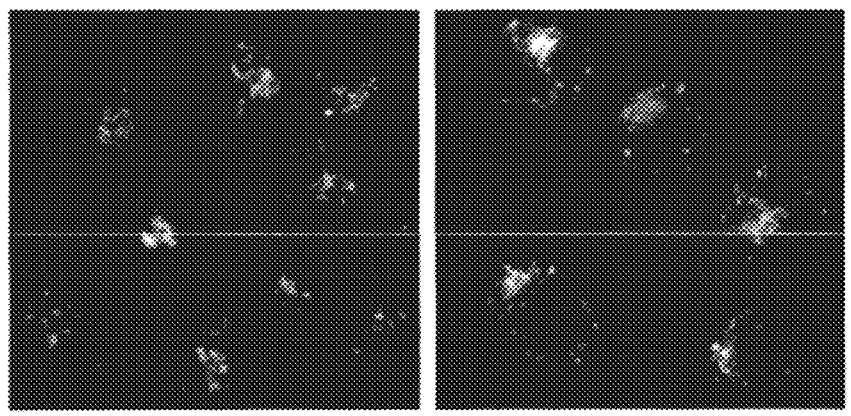
FIG. 25 provides a data and time comparison of an antibody internalization study performed with B cells as between the array plate of the present invention and immunofluorescence study eppendorf tubes. No centrifugation was needed for the array plate of the present invention, which also provides other benefits such as reduced time and reagents while delivering comparable data.
Figure 26:
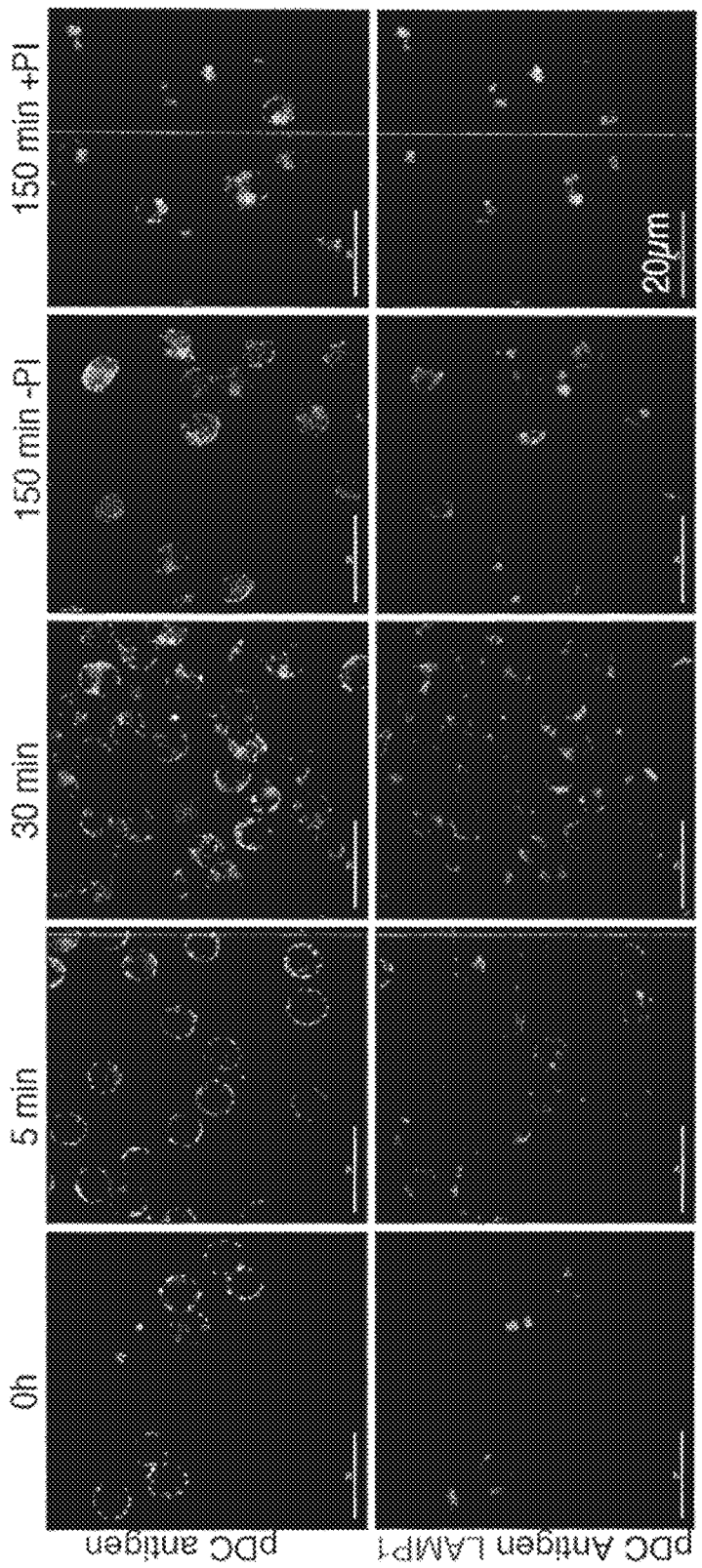
FIG. 26 shows the level of pDC (plasmactyoid dendritic cell) retention at 0 h, 5 min, 30 min, and 150 min time points in the course of an antibody internalization assay performed using an array plate of the present invention. Primary plasmacytoid dendritic cells (pDC) from blood are typically small size, almost 50-75% of B cells, and <0.4% of PBMC. Over 70+% retention of pDC cells was achieved when the assay was conducted using an array plate of the present invention and no centrifugation was needed.
Figures 27A, 27B:
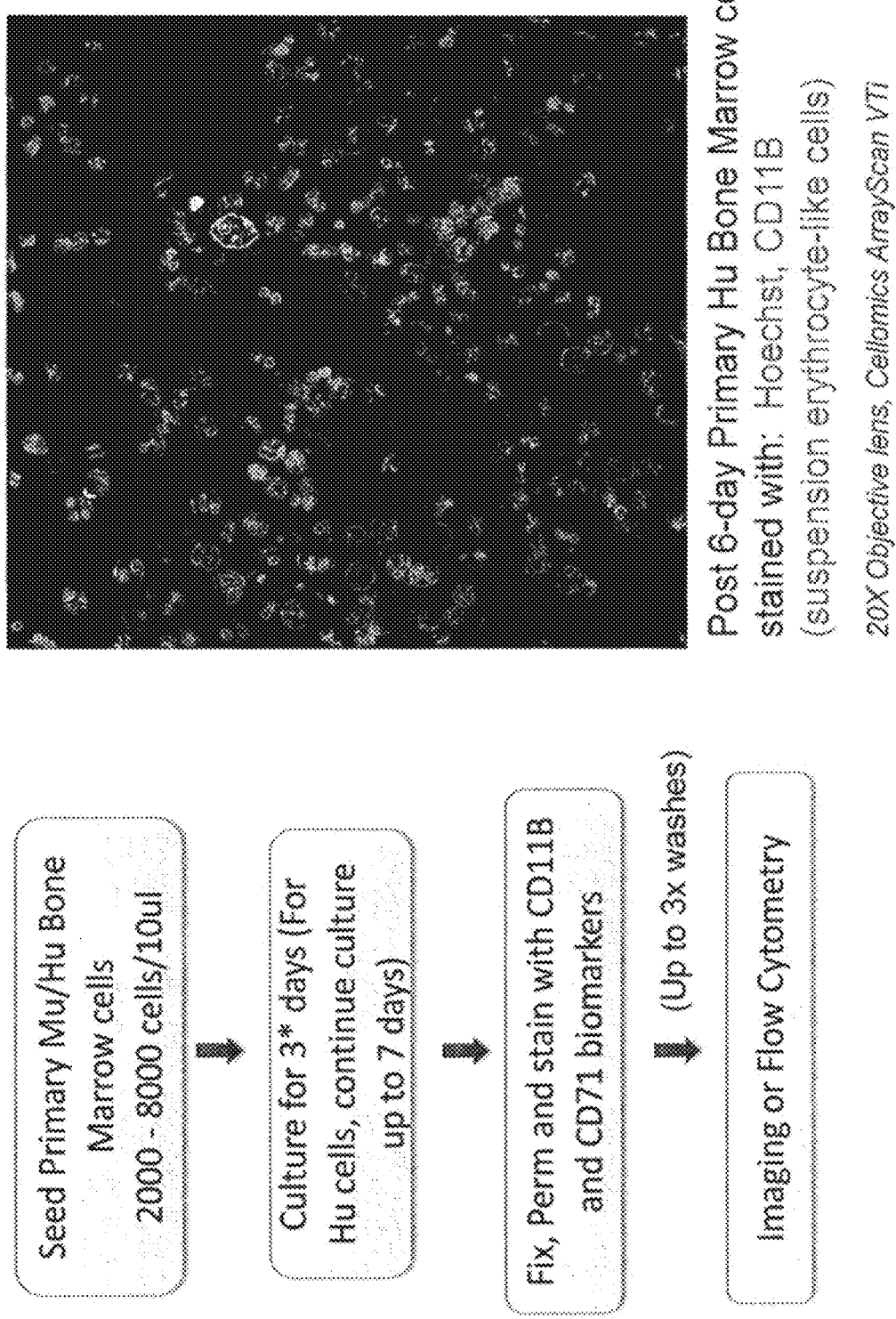
FIG. 27A provides an exemplary work flow diagram of long term culture and staining of suspension primary bone marrow cells.
FIG. 27B is an image at 20× objective of primary human bone marrow cells stained with CD11B at the 6-day time point.
Figure 28B:
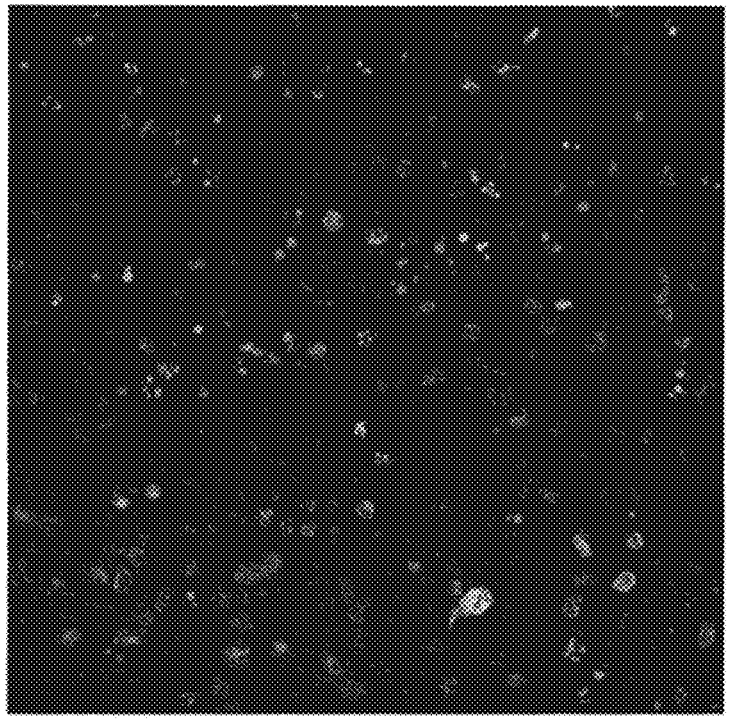
FIG. 28B is an image at 20× objective of primary human bone marrow cells stained with CD71 at the 6-day time point.
Figure 28A:
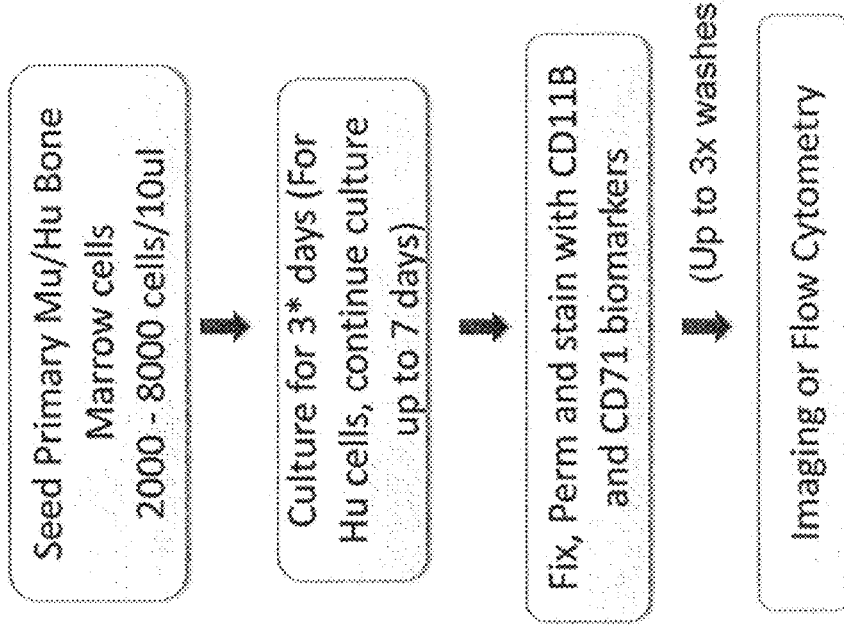
FIG. 28A provides an exemplary work flow diagram of long term culture and staining of suspension primary bone marrow cells.
Figure 29:
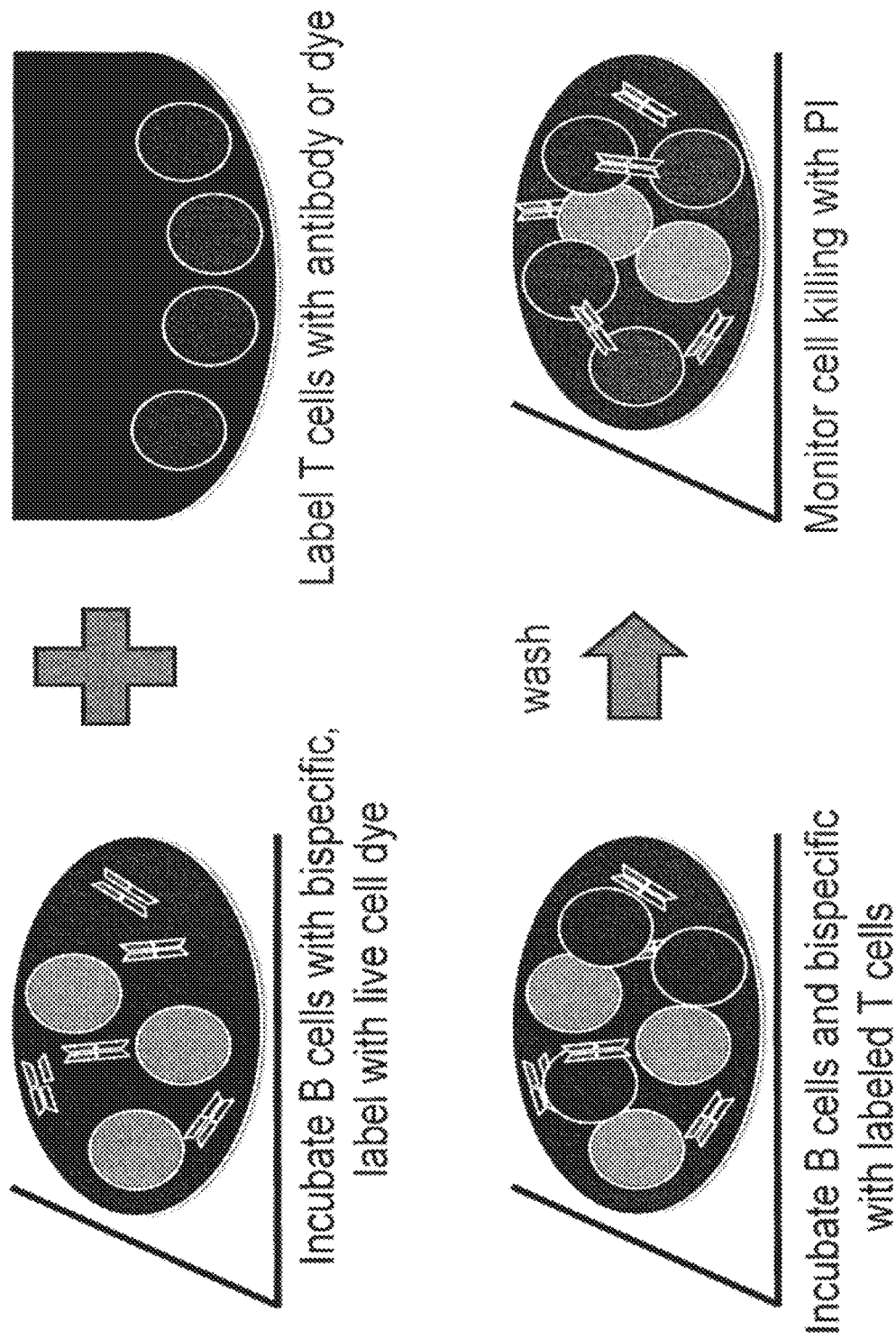
FIG. 29 provides an exemplary work flow diagram of a T-cell mediated lysis study using bispecific antibodies on an array plate of the present invention.
Figure 30:
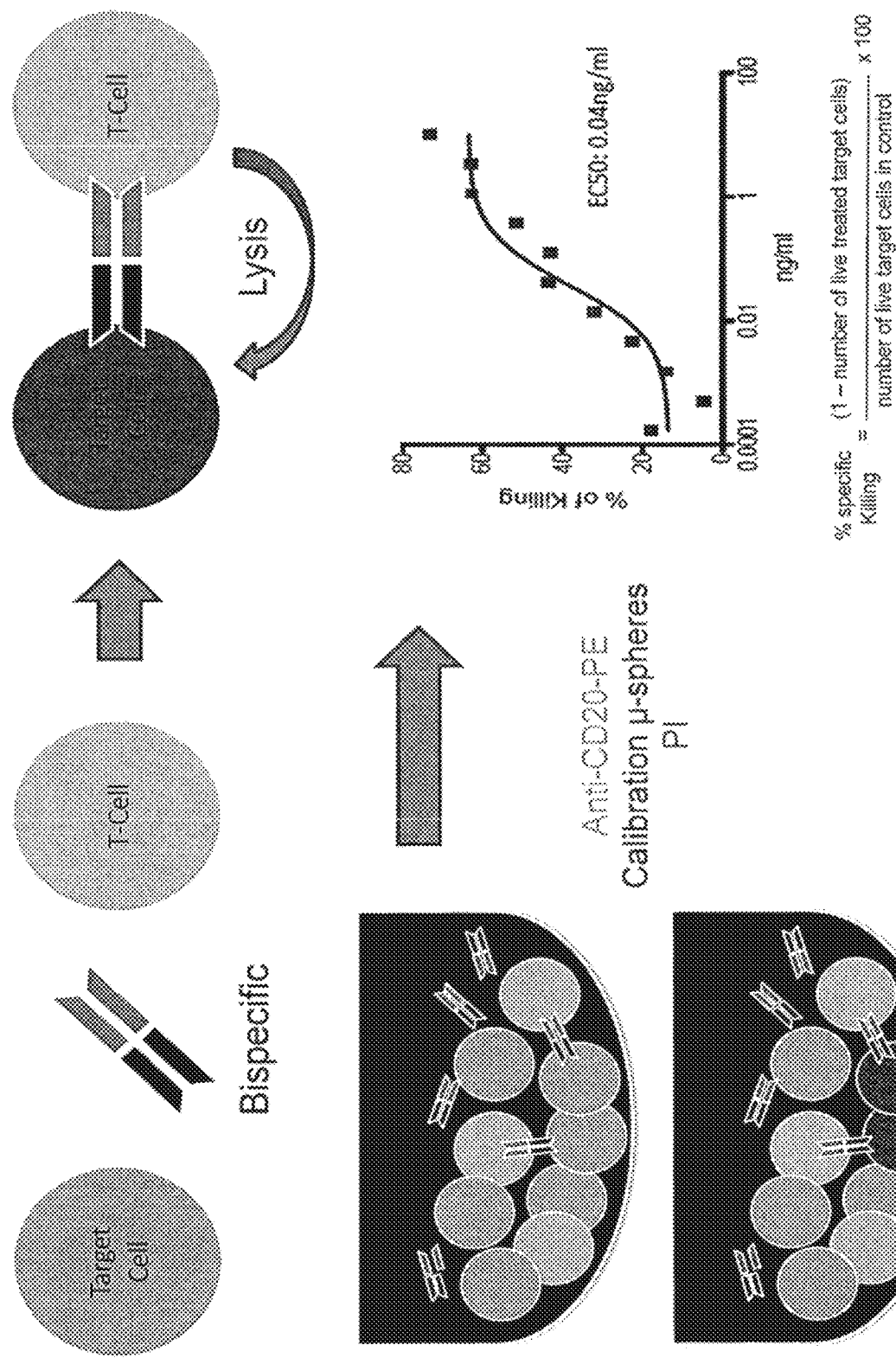
FIG. 30 provides an exemplary work flow diagram of a T-cell mediated lysis study using bispecific antibodies on an array plate of the present invention and the percentage of cells killed. T cells express CD3 (effector) whereas B cells express CD20 (target).
Figure 31:
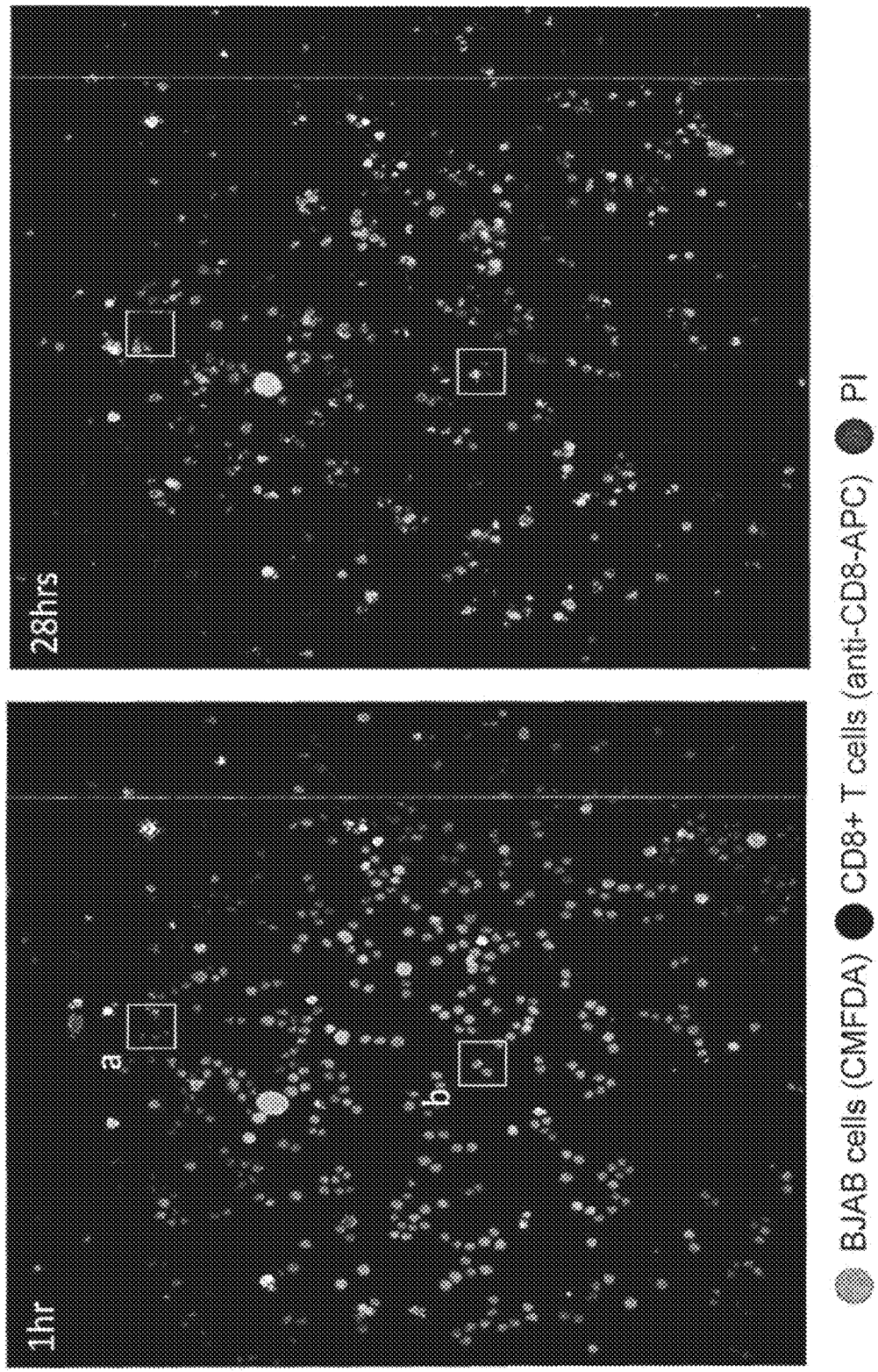
FIG. 31 are micrographs depicting BJAB, CD8+ T cells and PI-positive cells at the 1 h and 28 h time points in the T-cell mediated lysis study described in Example 17.
Figure 32:
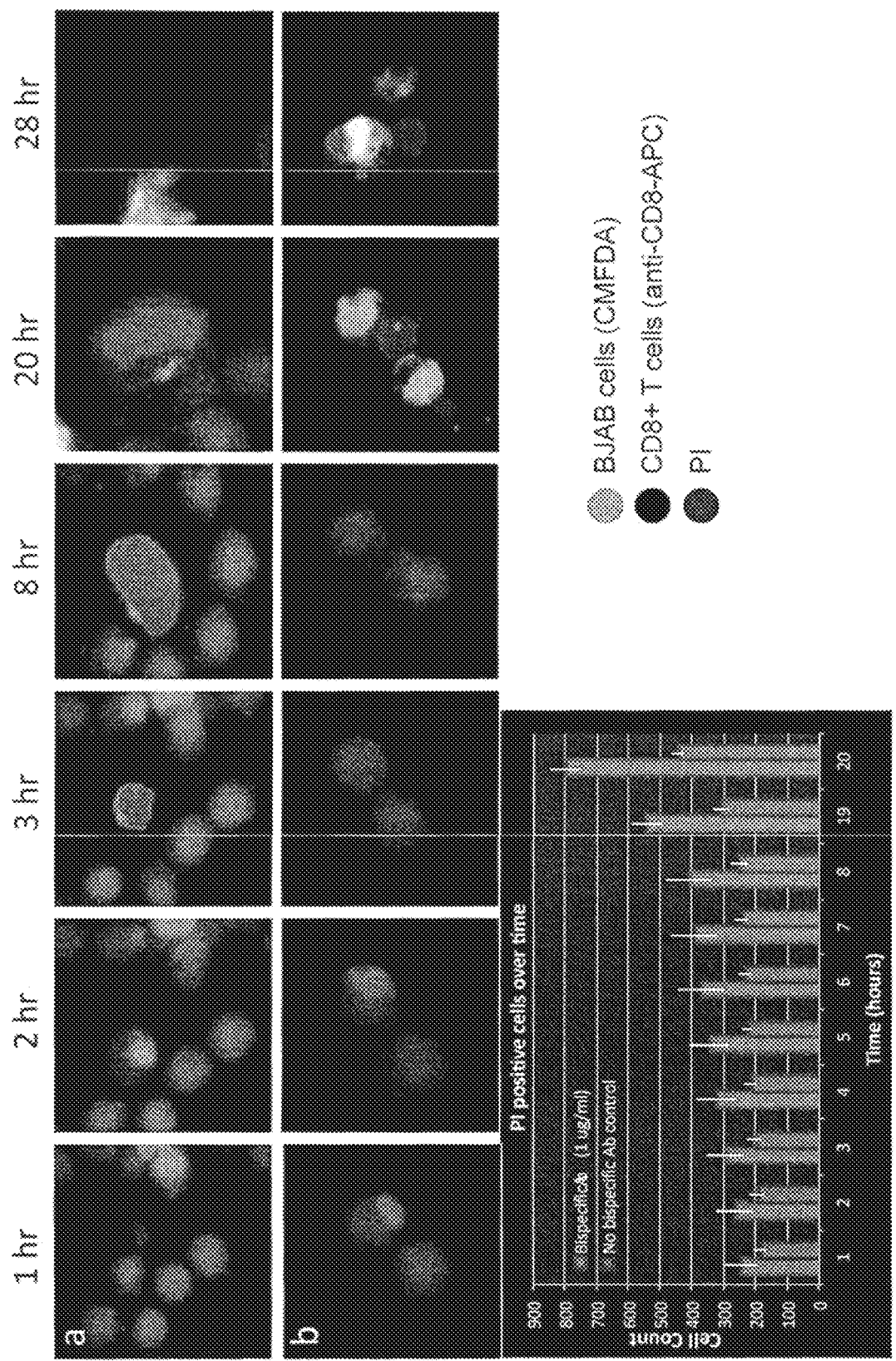
FIG. 32 are micrographs depicting BJAB, CD8+ T cells and PI-positive cells at the 1 h, 2 h, 3 h, 8 h, 20 h, and 28 h time points of a BiTE assay and a graph of the PI-positive cells over a 20 h period. In conventional methods, cells concentrate at the bottom of the well, creating an artificially skewed reading and it is not possible to distinguish between T-cell mediated killing and cell death by other means. Real-time imaging of the BiTE assay permits the visualization of T-cell mediated killing as distinguished from general apoptosis and necrosis.

Example 15: Trafficking and Time Course Study of Antibodies in Suspension B Cells with DropArray DropArray was validated extensively with 6 different B cell lines using 5 CD22 Abs by comparing traditional centrifuge method and DA method in Ab internalization study. See FIGS. 24-26. Amongst the 6 B cell lines employed was pDC (plasmactyoid dendritic cell), which is a rare and small cell derived found in the blood. The array plate of the present invention achieved a 70+% retention through an extensive immunostaining process without the need of centrifugation.

Example 16: Trafficking and Time Course Study of Antibodies in Suspension B Cells with DropArray Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims

What is claimed:

1. A method of culturing cells, comprising:
providing a processing compartment comprising a reservoir with a base surface, the processing compartment including a hydrophobic material and a hydrophilic material that is distinct from the hydrophobic material, said base surface having a hydrophobic solid surface defined by the hydrophobic material and an array of hydrophilic areas, each of said hydrophilic areas defined by the hydrophilic material and surrounded by the hydrophobic solid surface, only the hydrophobic solid surface being further covered with an immiscible hydrophobic liquid that is distinct from the hydrophobic material, and a plurality of said hydrophilic areas collectively having sample droplets disposed thereon, the sample droplets comprising cells;
incubating said base surface at a temperature suitable for cell culture;
flooding the reservoir with a wash fluid so that the wash fluid is concurrently in contact with the plurality of said hydrophilic areas;
draining the wash fluid from the reservoir;
filling said reservoir with an immiscible hydrophobic liquid;
tilting said processing compartment to remove all but a thin layer of said immiscible hydrophobic liquid that is retained on said base surface;
adding a first reagent to said processing compartment; and
tilting said processing compartment to remove said first reagent.

2. The method of claim 1, wherein said cells are non-adherent cells.

3. The method of claim 1, wherein said cells are stem cells selected from embryonic stem cells and fetal stem cells.

4. The method of claim 1, wherein only said hydrophilic areas are functionalized with a biomaterial prior to addition of the cells.

5. The method of claim 4, wherein said biomaterial is selected from the group consisting of collagen I, collagen II, collagen IV, poly-D-lysine (PDL), gelatin, fibronectin, laminin, and combinations thereof.

6. The method of claim 1, wherein the plurality of said hydrophilic areas is coated or covalently linked with a biological moiety selected from a small molecule, lipid, peptide, oligonucleotide, or oligosaccharide.

7. The method of claim 1, further comprising filling the reservoir with a cell culture medium, thereby immersing said cells.

8. The method of claim 7, further comprises replacing said cell culture medium by draining said cell culture medium and replacing with fresh cell culture medium.

9. The method of claim 8, wherein said replacing is done using a pipette.

10. The method of claim 8, wherein said replacing is done by tilting said surface to drain said cell culture medium and adding new cell culture medium.

11. The method of claim 7, wherein the sample droplets are coated with the immiscible liquid, thereby encasing each of the sample droplets on the base surface.

12. The method of claim 1, further comprising adding a transfection nucleic acid to a plurality of said hydrophilic areas and incubating at a suitable temperature.

13. The method of claim 12, further comprising assaying said cells to determine whether transfection has occurred.

14. The method of claim 12, wherein said transfection nucleic acid is DNA or siRNA.

15. The method of claim 1, further comprising:
adding a compound to at least one of said hydrophilic areas;
incubating said surface at a temperature suitable for cell culture; and
detecting the effect of said compound on said cells.

16. The method of claim 1, wherein said immiscible liquid is selected from a group consisting of a mineral oil, a silicone oil, a hydrocarbon compound, a hydroperflurocarbon compound, a perfluorocarbon compound, and a mixture thereof.

17. The method of claim 1, wherein each sample droplet has a volume of no greater than 12 μl.

18. The method of claim 1, wherein the array of said hydrophilic areas has a surface roughness in the range of 0.1-1000 μm.

19. The method of claim 18, wherein the surface roughness of the array of said hydrophilic areas is in the range of 100-1000 μm.

20. The method of claim 1, wherein draining the wash fluid from the reservoir includes tilting the reservoir at 90 degree or higher angle so that the wash fluid is drained from the reservoir.

* * * * *